US010684284B2

(12) United States Patent
Mahler et al.

(10) Patent No.: US 10,684,284 B2
(45) Date of Patent: Jun. 16, 2020

(54) COMPOSITIONS AND METHODS FOR THE DIAGNOSIS OF RHEUMATOID ARTHRITIS

(71) Applicants: INOVA DIAGNOSTICS, INC., San Diego, CA (US); LEIDEN UNIVERSITY MEDICAL CENTER, Leiden (NL)

(72) Inventors: Michael Mahler, Bad Neuenahr (DE); Leendert A. Trouw, Leiden (NL); Jan Wouter Drijfhout, Leiden (NL); Tom Huizinga, Leiden (NL); René Toes, Leiden (NL); Peter Van Veelen, Leiden (NL)

(73) Assignees: Inova Diagnostics, Inc., San Diego, CA (US); Leiden University Medical Center, Leiden (NL)

( * ) Notice: Subject to any disclaimer, the term of this patent is extended or adjusted under 35 U.S.C. 154(b) by 100 days.

(21) Appl. No.: 15/791,354

(22) Filed: Oct. 23, 2017

(65) Prior Publication Data
US 2018/0038856 A1 Feb. 8, 2018

Related U.S. Application Data

(63) Continuation of application No. 14/806,515, filed on Jul. 22, 2015, now Pat. No. 9,829,489.

(60) Provisional application No. 62/028,270, filed on Jul. 23, 2014.

(51) Int. Cl.
*G01N 33/564* (2006.01)
*C07K 14/81* (2006.01)
*C07K 1/107* (2006.01)

(52) U.S. Cl.
CPC ......... *G01N 33/564* (2013.01); *C07K 1/1075* (2013.01); *C07K 14/8125* (2013.01); *G01N 2333/8125* (2013.01); *G01N 2440/00* (2013.01); *G01N 2800/102* (2013.01)

(58) Field of Classification Search
None
See application file for complete search history.

(56) References Cited

U.S. PATENT DOCUMENTS

2005/0048574 A1 3/2005 Kantor et al.
2013/0011398 A1 1/2013 Eckelman et al.
2014/0162297 A1 6/2014 Trouw et al.

FOREIGN PATENT DOCUMENTS

WO WO 2012/163768 A1 12/2012
WO WO 2013/003649 A2 1/2013

OTHER PUBLICATIONS

Shimura et al.,"Immunoassay of serum alpha1-antitrypsin by affinity-probe capillary isoelectric focusing using a fluorescence-labeled recombinant antibody fragment", Electrophoresis 23: 909-917 (2002) (Year: 2002).*
Agarwal et al., Expression and purification of recombinant human alpha1-proteinase inhibitor and its single amino acid substituted variants in *Escherichia coli* for enhanced stability and biological activity: Human alpha-1-antitrypsin, partil [synthetic construct]: GenBank Accession No. ABV21360.1; GI:157086955 (May 20, 2010).
Aletaha et al., "2010 Rheumatoid arthritis classification criteria: an American College of Rheumatology/European League Against Rheumatism collaborative initiative," Ann. Rheum. Dis. 69(9):1580-1588 (2010).
Coleman et al., "Effects of amino acid sequence changes on antibody-antigen interactions", Res Immunol., 145(1):33-36 (1994).
Extended European Search Reported in corresponding European Patent Application No. EP 15825438.3 dated Feb. 23, 2017 (7 pages).
Harlow et al., "Antibodies: A Laboratory Manual", Cold Spring Harbor Laboratory Press, Cold Spring Harbor NY, pp. 23-26.
Iwana et al., "Prospective study of the clinical value of determining circulating IgA-alpha 1-antitrypsin complex using a prototype ELISA kit in patients with rheumatoid arthritis", Ann Rheum Dis., 55(11):848-851 (1996).
Lederman et al., "A single amino acid substitution in a common African allele of the CD4 molecule ablates binding of the monoclonal antibody, OKT4", Mol Immunol., 28(11):1171-1181 (1991).
Office Action in corresponding Canadian Patent Application No. 2,926,231 dated Feb. 3, 2017. (7 pages).
PCT International Search Report for International Application No. PCT/US2015/041448, dated Jan. 8, 2016.
Qin et al., "Rates of carbamylation of specific lysyl residues in bovine alpha-crystallins," J. Biol. Chem. 267(36):26128-26133 (1992).
Scott et al., "Comparison of IgA-α1-antitrypsin levels in rheumatoid arthritis and seronegative oligoarthritis: complex formation is not associated with inflammation per se," Br. J. Rheumatol. 37(4):398-404 (1998).
Shimura et al., "Immunoassay of serum alpha(1)-antitrypsin by affinity-probe capillary isoelectric focusing using a fluorescence-labeled recombinant antibody fragment," Electrophoresis 23(6):909-917 (2002).
Stefănescu et al., "The presence and significance of some anti-enzyme antibodies (anti-plasminogen, anti-trypsin, anti-phospholipase C) in rheumatoid arthritis (RA) and reactive arthritis (rA)," Arch. Roum. Pathol. Exp. Microbiol. 48(1):47-53 (1989).
Steĕpán et al., "Antigenic spectrum of soluble serum glycoproteins in rheumatoid arthritis", Z Rheumatol, 36(9-10):332-336 (1977) Abstract Only, from PubMed, PMID:303851.
Tomasi and Hauptman, "The binding of α-1 antitrypsin to human IgA," J. Immunol. 112(6):2274-2277 (1974).
Written Opinion for International Application No. PCT/US2015/041448, dated Jan. 8, 2016.

* cited by examiner

*Primary Examiner* — Anand U Desai
(74) *Attorney, Agent, or Firm* — Jones Day

(57) ABSTRACT

The present disclosure relates to the field of molecular biology and more specifically to methods for detecting anti-carbamylated protein (anti-CarP) antibodies in the serum of rheumatoid arthritis (RA) patients.

19 Claims, 10 Drawing Sheets

Specification includes a Sequence Listing.

SEQUENCE LISTING

```
<160> NUMBER OF SEQ ID NOS: 203

<210> SEQ ID NO 1
<211> LENGTH: 394
<212> TYPE: PRT
<213> ORGANISM: Homo sapiens

<400> SEQUENCE: 1

Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30
```

Phe Ala Phe Ser Leu Tyr Arg Gln Leu Ala His Gln Ser Asn Ser Thr
            35                  40                  45

Asn Ile Phe Phe Ser Pro Val Ser Ile Ala Thr Ala Phe Ala Met Leu
 50                  55                  60

Ser Leu Gly Thr Lys Ala Asp Thr His Asp Glu Ile Leu Glu Gly Leu
 65                  70                  75                  80

Asn Phe Asn Leu Thr Glu Ile Pro Glu Ala Gln Ile His Glu Gly Phe
                 85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
            115                 120                 125

Lys Phe Leu Glu Asp Val Lys Lys Leu Tyr His Ser Glu Ala Phe Thr
130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
            180                 185                 190

Lys Trp Glu Arg Pro Phe Glu Val Lys Asp Thr Glu Glu Glu Asp Phe
            195                 200                 205

His Val Asp Gln Val Thr Thr Val Lys Val Pro Met Met Lys Arg Leu
210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255

Glu Gly Lys Leu Gln His Leu Glu Asn Glu Leu Thr His Asp Ile Ile
            260                 265                 270

Thr Lys Phe Leu Glu Asn Glu Asp Arg Arg Ser Ala Ser Leu His Leu
            275                 280                 285

Pro Lys Leu Ser Ile Thr Gly Thr Tyr Asp Leu Lys Ser Val Leu Gly
290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335

Val Leu Thr Ile Asp Glu Lys Gly Thr Glu Ala Ala Gly Ala Met Phe
            340                 345                 350

Leu Glu Ala Ile Pro Met Ser Ile Pro Pro Glu Val Lys Phe Asn Lys
            355                 360                 365

Pro Phe Val Phe Leu Met Ile Glu Gln Asn Thr Lys Ser Pro Leu Phe
370                 375                 380

Met Gly Lys Val Val Asn Pro Thr Gln Lys
385                 390

<210> SEQ ID NO 2
<211> LENGTH: 392
<212> TYPE: PRT
<213> ORGANISM: Bos taurus

<400> SEQUENCE: 2

Gly Val Leu Gln Gly His Ala Val Gln Glu Thr Asp Asp Thr Ser His
1               5                   10                  15

-continued

Gln Glu Ala Ala Cys His Lys Ile Ala Pro Asn Leu Ala Asn Phe Ala
            20                  25                  30

Phe Ser Ile Tyr His His Leu Ala His Gln Ser Asn Thr Ser Asn Ile
        35                  40                  45

Phe Phe Ser Pro Val Ser Ile Ala Ser Ala Phe Ala Met Leu Ser Leu
50                  55                  60

Gly Ala Lys Gly Asn Thr His Thr Glu Ile Leu Lys Gly Leu Gly Phe
65                  70                  75                  80

Asn Leu Thr Glu Leu Ala Glu Ala Gly Ile His Lys Gly Phe Gln His
                85                  90                  95

Leu Leu His Thr Leu Asn Gln Pro Asn His Gln Leu Gln Leu Thr Thr
            100                 105                 110

Gly Asn Gly Leu Phe Ile Asn Glu Ser Ala Lys Leu Val Asp Thr Phe
        115                 120                 125

Leu Glu Asp Val Lys Asn Leu Tyr His Ser Glu Ala Phe Ser Ile Asn
130                 135                 140

Phe Arg Asp Ala Glu Glu Ala Lys Lys Lys Ile Asn Asp Tyr Val Glu
145                 150                 155                 160

Lys Gly Ser His Gly Lys Ile Val Glu Leu Val Lys Val Leu Asp Pro
                165                 170                 175

Asn Thr Val Phe Ala Leu Val Asn Tyr Ile Ser Phe Lys Gly Lys Trp
            180                 185                 190

Glu Lys Pro Phe Glu Met Lys His Thr Thr Glu Arg Asp Phe His Val
        195                 200                 205

Asp Glu Gln Thr Thr Val Lys Val Pro Met Met Asn Arg Leu Gly Met
210                 215                 220

Phe Asp Leu His Tyr Cys Asp Lys Leu Ala Ser Trp Val Leu Leu Leu
225                 230                 235                 240

Asp Tyr Val Gly Asn Val Thr Ala Cys Phe Ile Leu Pro Asp Leu Gly
                245                 250                 255

Lys Leu Gln Gln Leu Glu Asp Lys Leu Asn Asn Glu Leu Leu Ala Lys
            260                 265                 270

Phe Leu Glu Lys Lys Tyr Ala Ser Ser Ala Asn Leu His Leu Pro Lys
        275                 280                 285

Leu Ser Ile Ser Glu Thr Tyr Asp Leu Lys Ser Val Leu Gly Asp Val
290                 295                 300

Gly Ile Thr Glu Val Phe Ser Asp Arg Ala Asp Leu Ser Gly Ile Thr
305                 310                 315                 320

Lys Glu Gln Pro Leu Lys Val Ser Lys Ala Leu His Lys Ala Ala Leu
                325                 330                 335

Thr Ile Asp Glu Lys Gly Thr Glu Ala Val Gly Ser Thr Phe Leu Glu
            340                 345                 350

Ala Ile Pro Met Ser Leu Pro Pro Asp Val Glu Phe Asn Arg Pro Phe
        355                 360                 365

Leu Cys Ile Leu Tyr Asp Arg Asn Thr Lys Ser Pro Leu Phe Val Gly
370                 375                 380

Lys Val Val Asn Pro Thr Gln Ala
385                 390

<210> SEQ ID NO 3
<211> LENGTH: 21
<212> TYPE: PRT
<213> ORGANISM: Homo sapiens

-continued

```
<400> SEQUENCE: 3

Ala Glu Asp Pro Gln Gly Asp Ala Ala Gln Lys Thr Asp Thr Ser His
1               5                   10                  15

His Asp Gln Asp His
            20

<210> SEQ ID NO 4
<211> LENGTH: 21
<212> TYPE: PRT
<213> ORGANISM: Homo sapiens

<400> SEQUENCE: 4

His His Asp Gln Asp His Pro Thr Phe Asn Lys Ile Thr Pro Asn Leu
1               5                   10                  15

Ala Glu Phe Ala Phe
            20

<210> SEQ ID NO 5
<211> LENGTH: 21
<212> TYPE: PRT
<213> ORGANISM: Homo sapiens

<400> SEQUENCE: 5

Thr Ala Phe Ala Met Leu Ser Leu Gly Thr Lys Ala Asp Thr His Asp
1               5                   10                  15

Glu Ile Leu Glu Gly
            20

<210> SEQ ID NO 6
<211> LENGTH: 20
<212> TYPE: PRT
<213> ORGANISM: Homo sapiens

<400> SEQUENCE: 6

Gly Asn Gly Leu Phe Leu Ser Glu Gly Leu Lys Leu Val Asp Lys Phe
1               5                   10                  15

Leu Glu Asp Val
            20

<210> SEQ ID NO 7
<211> LENGTH: 21
<212> TYPE: PRT
<213> ORGANISM: Homo sapiens

<400> SEQUENCE: 7

Phe Leu Ser Glu Gly Leu Lys Leu Val Asp Lys Phe Leu Glu Asp Val
1               5                   10                  15

Lys Lys Leu Tyr His
            20

<210> SEQ ID NO 8
<211> LENGTH: 21
<212> TYPE: PRT
<213> ORGANISM: Homo sapiens

<400> SEQUENCE: 8

Lys Leu Val Asp Lys Phe Leu Glu Asp Val Lys Lys Leu Tyr His Ser
1               5                   10                  15

Glu Ala Phe Thr Val
            20
```

```
<210> SEQ ID NO 9
<211> LENGTH: 21
<212> TYPE: PRT
<213> ORGANISM: Homo sapiens

<400> SEQUENCE: 9

Thr Val Asn Phe Gly Asp Thr Glu Glu Ala Lys Lys Gln Ile Asn Asp
1               5                   10                  15

Tyr Val Glu Lys Gly
            20

<210> SEQ ID NO 10
<211> LENGTH: 21
<212> TYPE: PRT
<213> ORGANISM: Homo sapiens

<400> SEQUENCE: 10

Ala Lys Lys Gln Ile Asn Asp Tyr Val Glu Lys Gly Thr Gln Gly Lys
1               5                   10                  15

Ile Val Asp Leu Val
            20

<210> SEQ ID NO 11
<211> LENGTH: 21
<212> TYPE: PRT
<213> ORGANISM: Homo sapiens

<400> SEQUENCE: 11

Asn Asp Tyr Val Glu Lys Gly Thr Gln Gly Lys Ile Val Asp Leu Val
1               5                   10                  15

Lys Glu Leu Asp Arg
            20

<210> SEQ ID NO 12
<211> LENGTH: 21
<212> TYPE: PRT
<213> ORGANISM: Homo sapiens

<400> SEQUENCE: 12

Gly Thr Gln Gly Lys Ile Val Asp Leu Val Lys Glu Leu Asp Arg Asp
1               5                   10                  15

Thr Val Phe Ala Leu
            20

<210> SEQ ID NO 13
<211> LENGTH: 21
<212> TYPE: PRT
<213> ORGANISM: Homo sapiens

<400> SEQUENCE: 13

Val Phe Ala Leu Val Asn Tyr Ile Phe Phe Lys Gly Lys Trp Glu Arg
1               5                   10                  15

Pro Phe Glu Val Lys
            20

<210> SEQ ID NO 14
<211> LENGTH: 21
<212> TYPE: PRT
<213> ORGANISM: Homo sapiens

<400> SEQUENCE: 14

Lys Gly Lys Trp Glu Arg Pro Phe Glu Val Lys Asp Thr Glu Glu Glu
1               5                   10                  15
```

Asp Phe His Val Asp
            20

<210> SEQ ID NO 15
<211> LENGTH: 21
<212> TYPE: PRT
<213> ORGANISM: Homo sapiens

<400> SEQUENCE: 15

Asp Phe His Val Asp Gln Val Thr Thr Val Lys Val Pro Met Met Lys
1               5                   10                  15

Arg Leu Gly Met Phe
            20

<210> SEQ ID NO 16
<211> LENGTH: 21
<212> TYPE: PRT
<213> ORGANISM: Homo sapiens

<400> SEQUENCE: 16

Gln Val Thr Thr Val Lys Val Pro Met Met Lys Arg Leu Gly Met Phe
1               5                   10                  15

Asn Ile Gln His Cys
            20

<210> SEQ ID NO 17
<211> LENGTH: 21
<212> TYPE: PRT
<213> ORGANISM: Homo sapiens

<400> SEQUENCE: 17

Arg Leu Gly Met Phe Asn Ile Gln His Cys Lys Lys Leu Ser Ser Trp
1               5                   10                  15

Val Leu Leu Met Lys
            20

<210> SEQ ID NO 18
<211> LENGTH: 21
<212> TYPE: PRT
<213> ORGANISM: Homo sapiens

<400> SEQUENCE: 18

Lys Lys Leu Ser Ser Trp Val Leu Leu Met Lys Tyr Leu Gly Asn Ala
1               5                   10                  15

Thr Ala Ile Phe Phe
            20

<210> SEQ ID NO 19
<211> LENGTH: 21
<212> TYPE: PRT
<213> ORGANISM: Homo sapiens

<400> SEQUENCE: 19

Thr Ala Ile Phe Phe Leu Pro Asp Glu Gly Lys Leu Gln His Leu Glu
1               5                   10                  15

Asn Glu Leu Thr His
            20

<210> SEQ ID NO 20
<211> LENGTH: 21
<212> TYPE: PRT
<213> ORGANISM: Homo sapiens

```
<400> SEQUENCE: 20

Glu Asn Glu Leu Thr His Asp Ile Ile Thr Lys Phe Leu Glu Asn Glu
1               5                   10                  15

Asp Arg Arg Ser Ala
            20

<210> SEQ ID NO 21
<211> LENGTH: 21
<212> TYPE: PRT
<213> ORGANISM: Homo sapiens

<400> SEQUENCE: 21

Asp Arg Arg Ser Ala Ser Leu His Leu Pro Lys Leu Ser Ile Thr Gly
1               5                   10                  15

Thr Tyr Asp Leu Lys
            20

<210> SEQ ID NO 22
<211> LENGTH: 21
<212> TYPE: PRT
<213> ORGANISM: Homo sapiens

<400> SEQUENCE: 22

Lys Leu Ser Ile Thr Gly Thr Tyr Asp Leu Lys Ser Val Leu Gly Gln
1               5                   10                  15

Leu Gly Ile Thr Lys
            20

<210> SEQ ID NO 23
<211> LENGTH: 21
<212> TYPE: PRT
<213> ORGANISM: Homo sapiens

<400> SEQUENCE: 23

Lys Ser Val Leu Gly Gln Leu Gly Ile Thr Lys Val Phe Ser Asn Gly
1               5                   10                  15

Ala Asp Leu Ser Gly
            20

<210> SEQ ID NO 24
<211> LENGTH: 21
<212> TYPE: PRT
<213> ORGANISM: Homo sapiens

<400> SEQUENCE: 24

Leu Ser Gly Val Thr Glu Glu Ala Pro Leu Lys Leu Ser Lys Ala Val
1               5                   10                  15

His Lys Ala Val Leu
            20

<210> SEQ ID NO 25
<211> LENGTH: 21
<212> TYPE: PRT
<213> ORGANISM: Homo sapiens

<400> SEQUENCE: 25

Val Thr Glu Glu Ala Pro Leu Lys Leu Ser Lys Ala Val His Lys Ala
1               5                   10                  15

Val Leu Thr Ile Asp
            20
```

```
<210> SEQ ID NO 26
<211> LENGTH: 21
<212> TYPE: PRT
<213> ORGANISM: Homo sapiens

<400> SEQUENCE: 26

Ala Pro Leu Lys Leu Ser Lys Ala Val His Lys Ala Val Leu Thr Ile
1               5                   10                  15

Asp Glu Lys Gly Thr
            20

<210> SEQ ID NO 27
<211> LENGTH: 21
<212> TYPE: PRT
<213> ORGANISM: Homo sapiens

<400> SEQUENCE: 27

Val His Lys Ala Val Leu Thr Ile Asp Glu Lys Gly Thr Glu Ala Ala
1               5                   10                  15

Gly Ala Met Phe Leu
            20

<210> SEQ ID NO 28
<211> LENGTH: 21
<212> TYPE: PRT
<213> ORGANISM: Homo sapiens

<400> SEQUENCE: 28

Ala Ile Pro Met Ser Ile Pro Pro Glu Val Lys Phe Asn Lys Pro Phe
1               5                   10                  15

Val Phe Leu Met Ile
            20

<210> SEQ ID NO 29
<211> LENGTH: 21
<212> TYPE: PRT
<213> ORGANISM: Homo sapiens

<400> SEQUENCE: 29

Met Ser Ile Pro Pro Glu Val Lys Phe Asn Lys Pro Phe Val Phe Leu
1               5                   10                  15

Met Ile Glu Gln Asn
            20

<210> SEQ ID NO 30
<211> LENGTH: 21
<212> TYPE: PRT
<213> ORGANISM: Homo sapiens

<400> SEQUENCE: 30

Phe Val Phe Leu Met Ile Glu Gln Asn Thr Lys Ser Pro Leu Phe Met
1               5                   10                  15

Gly Lys Val Val Asn
            20

<210> SEQ ID NO 31
<211> LENGTH: 21
<212> TYPE: PRT
<213> ORGANISM: Homo sapiens

<400> SEQUENCE: 31

Glu Gln Asn Thr Lys Ser Pro Leu Phe Met Gly Lys Val Val Asn Pro
```

```
1               5                   10                  15

Thr Gln Lys Ala Ala
            20

<210> SEQ ID NO 32
<211> LENGTH: 21
<212> TYPE: PRT
<213> ORGANISM: Homo sapiens

<400> SEQUENCE: 32

Ala Leu Val Asn Tyr Ile Phe Phe Lys Gly Lys Trp Glu Arg Pro Phe
1               5                   10                  15

Glu Val Lys Asp Thr
            20

<210> SEQ ID NO 33
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Lys(Car)

<400> SEQUENCE: 33

Ala Glu Asp Pro Gln Gly Asp Ala Ala Gln Lys Thr Asp Thr Ser His
1               5                   10                  15

His Asp Gln Asp His
            20

<210> SEQ ID NO 34
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Lys(Car)

<400> SEQUENCE: 34

His His Asp Gln Asp His Pro Thr Phe Asn Lys Ile Thr Pro Asn Leu
1               5                   10                  15

Ala Glu Phe Ala Phe
            20

<210> SEQ ID NO 35
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Lys(Car)

<400> SEQUENCE: 35

Thr Ala Phe Ala Met Leu Ser Leu Gly Thr Lys Ala Asp Thr His Asp
1               5                   10                  15
```

```
Glu Ile Leu Glu Gly
            20

<210> SEQ ID NO 36
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Lys(Car)

<400> SEQUENCE: 36

Gly Asn Gly Leu Phe Leu Ser Glu Gly Leu Lys Leu Val Asp Lys Phe
1               5                   10                  15

Leu Glu Asp Val
            20

<210> SEQ ID NO 37
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Lys(Car)

<400> SEQUENCE: 37

Gly Asn Gly Leu Phe Leu Ser Glu Gly Leu Lys Leu Val Asp Lys Phe
1               5                   10                  15

Leu Glu Asp Val
            20

<210> SEQ ID NO 38
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Lys(Car)
<220> FEATURE:
<221> NAME/KEY: MOD_RES
<222> LOCATION: (15)..(15)
<223> OTHER INFORMATION: Lys(Car)

<400> SEQUENCE: 38

Gly Asn Gly Leu Phe Leu Ser Glu Gly Leu Lys Leu Val Asp Lys Phe
1               5                   10                  15

Leu Glu Asp Val
            20

<210> SEQ ID NO 39
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (7)..(7)
<223> OTHER INFORMATION: Lys(Car)

<400> SEQUENCE: 39

Phe Leu Ser Glu Gly Leu Lys Leu Val Asp Lys Phe Leu Glu Asp Val
1               5                   10                  15

Lys Lys Leu Tyr His
            20

<210> SEQ ID NO 40
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Lys(Car)

<400> SEQUENCE: 40

Phe Leu Ser Glu Gly Leu Lys Leu Val Asp Lys Phe Leu Glu Asp Val
1               5                   10                  15

Lys Lys Leu Tyr His
            20

<210> SEQ ID NO 41
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: Lys(Car)

<400> SEQUENCE: 41

Phe Leu Ser Glu Gly Leu Lys Leu Val Asp Lys Phe Leu Glu Asp Val
1               5                   10                  15

Lys Lys Leu Tyr His
            20

<210> SEQ ID NO 42
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Lys(Car)

<400> SEQUENCE: 42

Phe Leu Ser Glu Gly Leu Lys Leu Val Asp Lys Phe Leu Glu Asp Val
1               5                   10                  15

Lys Lys Leu Tyr His
            20

<210> SEQ ID NO 43
<211> LENGTH: 21
<212> TYPE: PRT
```

<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Lys(Car)
<220> FEATURE:
<221> NAME/KEY: MOD_RES
<222> LOCATION: (11)..(11)
<223> OTHER INFORMATION: Lys(Car)

<400> SEQUENCE: 43

Phe Leu Ser Glu Gly Leu Lys Leu Val Asp Lys Phe Leu Glu Asp Val
1               5                   10                  15

Lys Lys Leu Tyr His
            20

<210> SEQ ID NO 44
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Lys(Car)
<220> FEATURE:
<221> NAME/KEY: MOD_RES
<222> LOCATION: (17)..(17)
<223> OTHER INFORMATION: Lys(Car)

<400> SEQUENCE: 44

Phe Leu Ser Glu Gly Leu Lys Leu Val Asp Lys Phe Leu Glu Asp Val
1               5                   10                  15

Lys Lys Leu Tyr His
            20

<210> SEQ ID NO 45
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Lys(Car)
<220> FEATURE:
<221> NAME/KEY: MOD_RES
<222> LOCATION: (18)..(18)
<223> OTHER INFORMATION: Lys(Car)

<400> SEQUENCE: 45

Phe Leu Ser Glu Gly Leu Lys Leu Val Asp Lys Phe Leu Glu Asp Val
1               5                   10                  15

Lys Lys Leu Tyr His
            20

<210> SEQ ID NO 46
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<221> NAME/KEY: MOD_RES
<222> LOCATION: (11)..(11)
<223> OTHER INFORMATION: Lys(Car)
<220> FEATURE:
<221> NAME/KEY: MOD_RES
<222> LOCATION: (17)..(17)
<223> OTHER INFORMATION: Lys(Car)

<400> SEQUENCE: 46

Phe Leu Ser Glu Gly Leu Lys Leu Val Asp Lys Phe Leu Glu Asp Val
1               5                   10                  15

Lys Lys Leu Tyr His
            20

<210> SEQ ID NO 47
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Lys(Car)
<220> FEATURE:
<221> NAME/KEY: MOD_RES
<222> LOCATION: (18)..(18)
<223> OTHER INFORMATION: Lys(Car)

<400> SEQUENCE: 47

Phe Leu Ser Glu Gly Leu Lys Leu Val Asp Lys Phe Leu Glu Asp Val
1               5                   10                  15

Lys Lys Leu Tyr His
            20

<210> SEQ ID NO 48
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(18)
<223> OTHER INFORMATION: Lys(Car)

<400> SEQUENCE: 48

Phe Leu Ser Glu Gly Leu Lys Leu Val Asp Lys Phe Leu Glu Asp Val
1               5                   10                  15

Lys Lys Leu Tyr His
            20

<210> SEQ ID NO 49
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Lys(Car)
<220> FEATURE:
<221> NAME/KEY: MOD_RES
<222> LOCATION: (11)..(11)
<223> OTHER INFORMATION: Lys(Car)
```

```
<220> FEATURE:
<221> NAME/KEY: MOD_RES
<222> LOCATION: (17)..(17)
<223> OTHER INFORMATION: Lys(Car)

<400> SEQUENCE: 49

Phe Leu Ser Glu Gly Leu Lys Leu Val Asp Lys Phe Leu Glu Asp Val
1               5                   10                  15

Lys Lys Leu Tyr His
            20

<210> SEQ ID NO 50
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Lys(Car)
<220> FEATURE:
<221> NAME/KEY: MOD_RES
<222> LOCATION: (11)..(11)
<223> OTHER INFORMATION: Lys(Car)
<220> FEATURE:
<221> NAME/KEY: MOD_RES
<222> LOCATION: (18)..(18)
<223> OTHER INFORMATION: Lys(Car)

<400> SEQUENCE: 50

Phe Leu Ser Glu Gly Leu Lys Leu Val Asp Lys Phe Leu Glu Asp Val
1               5                   10                  15

Lys Lys Leu Tyr His
            20

<210> SEQ ID NO 51
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Lys(Car)
<220> FEATURE:
<221> NAME/KEY: MOD_RES
<222> LOCATION: (17)..(18)
<223> OTHER INFORMATION: Lys(Car)

<400> SEQUENCE: 51

Phe Leu Ser Glu Gly Leu Lys Leu Val Asp Lys Phe Leu Glu Asp Val
1               5                   10                  15

Lys Lys Leu Tyr His
            20

<210> SEQ ID NO 52
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Lys(Car)
```

```
<220> FEATURE:
<221> NAME/KEY: MOD_RES
<222> LOCATION: (17)..(18)
<223> OTHER INFORMATION: Lys(Car)

<400> SEQUENCE: 52

Phe Leu Ser Glu Gly Leu Lys Leu Val Asp Lys Phe Leu Glu Asp Val
1               5                   10                  15

Lys Lys Leu Tyr His
            20

<210> SEQ ID NO 53
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Lys(Car)
<220> FEATURE:
<221> NAME/KEY: MOD_RES
<222> LOCATION: (11)..(11)
<223> OTHER INFORMATION: Lys(Car)
<220> FEATURE:
<221> NAME/KEY: MOD_RES
<222> LOCATION: (17)..(18)
<223> OTHER INFORMATION: Lys(Car)

<400> SEQUENCE: 53

Phe Leu Ser Glu Gly Leu Lys Leu Val Asp Lys Phe Leu Glu Asp Val
1               5                   10                  15

Lys Lys Leu Tyr His
            20

<210> SEQ ID NO 54
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(Car)

<400> SEQUENCE: 54

Lys Leu Val Asp Lys Phe Leu Glu Asp Val Lys Lys Leu Tyr His Ser
1               5                   10                  15

Glu Ala Phe Thr Val
            20

<210> SEQ ID NO 55
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Lys(Car)

<400> SEQUENCE: 55

Lys Leu Val Asp Lys Phe Leu Glu Asp Val Lys Lys Leu Tyr His Ser
```

```
1               5                   10                  15

Glu Ala Phe Thr Val
            20

<210> SEQ ID NO 56
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Lys(Car)

<400> SEQUENCE: 56

Lys Leu Val Asp Lys Phe Leu Glu Asp Val Lys Lys Leu Tyr His Ser
1               5                   10                  15

Glu Ala Phe Thr Val
            20

<210> SEQ ID NO 57
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Lys(Car)

<400> SEQUENCE: 57

Lys Leu Val Asp Lys Phe Leu Glu Asp Val Lys Lys Leu Tyr His Ser
1               5                   10                  15

Glu Ala Phe Thr Val
            20

<210> SEQ ID NO 58
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(Car)
<220> FEATURE:
<221> NAME/KEY: MOD_RES
<222> LOCATION: (5)..(5)
<223> OTHER INFORMATION: Lys(Car)

<400> SEQUENCE: 58

Lys Leu Val Asp Lys Phe Leu Glu Asp Val Lys Lys Leu Tyr His Ser
1               5                   10                  15

Glu Ala Phe Thr Val
            20

<210> SEQ ID NO 59
<211> LENGTH: 21
<212> TYPE: PRT
<213> ORGANISM: Artificial Sequence
<220> FEATURE:
<223> OTHER INFORMATION: Description of Artificial Sequence: Synthetic
```

-continued

```
        peptide
<220> FEATURE:
<221> NAME/KEY: MOD_RES
<222> LOCATION: (1)..(1)
<223> OTHER INFORMATION: Lys(Car)
<220> FEATURE:
<221> NAME/KEY: MOD_RES
<222> LOCATION: (11)..(11)
<223> OTHER INFORMATION: Lys(Car)

<400> SEQUENCE: 59

Lys Leu Val Asp Lys Phe Leu Glu Asp Val Lys Lys Leu Tyr His Ser
1               5                   10                  15

Glu Ala Phe Thr Val
            20

<210> SEQ ID NO 60
<211> LENGTH: 21
<212> TYPE: PRT
<213> ORGANISM: Artificial Sequence
<220> FEATURE:
<223> OTHER INFORMATION: Description of Artificial Sequence: Synthetic
        peptide
<220> FEATURE:
<221> NAME/KEY: MOD_RES
<222> LOCATION: (1)..(1)
<223> OTHER INFORMATION: Lys(Car)
<220> FEATURE:
<221> NAME/KEY: MOD_RES
<222> LOCATION: (12)..(12)
<223> OTHER INFORMATION: Lys(Car)

<400> SEQUENCE: 60

Lys Leu Val Asp Lys Phe Leu Glu Asp Val Lys Lys Leu Tyr His Ser
1               5                   10                  15

Glu Ala Phe Thr Val
            20

<210> SEQ ID NO 61
<211> LENGTH: 21
<212> TYPE: PRT
<213> ORGANISM: Artificial Sequence
<220> FEATURE:
<223> OTHER INFORMATION: Description of Artificial Sequence: Synthetic
        peptide
<220> FEATURE:
<221> NAME/KEY: MOD_RES
<222> LOCATION: (5)..(5)
<223> OTHER INFORMATION: Lys(Car)
<220> FEATURE:
<221> NAME/KEY: MOD_RES
<222> LOCATION: (11)..(11)
<223> OTHER INFORMATION: Lys(Car)

<400> SEQUENCE: 61

Lys Leu Val Asp Lys Phe Leu Glu Asp Val Lys Lys Leu Tyr His Ser
1               5                   10                  15

Glu Ala Phe Thr Val
            20

<210> SEQ ID NO 62
<211> LENGTH: 21
<212> TYPE: PRT
<213> ORGANISM: Artificial Sequence
<220> FEATURE:
<223> OTHER INFORMATION: Description of Artificial Sequence: Synthetic
        peptide
<220> FEATURE:
<221> NAME/KEY: MOD_RES
<222> LOCATION: (5)..(5)
```

<223> OTHER INFORMATION: Lys(Car)
<220> FEATURE:
<221> NAME/KEY: MOD_RES
<222> LOCATION: (12)..(12)
<223> OTHER INFORMATION: Lys(Car)

<400> SEQUENCE: 62

Lys Leu Val Asp Lys Phe Leu Glu Asp Val Lys Lys Leu Tyr His Ser
1               5                   10                  15

Glu Ala Phe Thr Val
            20

<210> SEQ ID NO 63
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(12)
<223> OTHER INFORMATION: Lys(Car)

<400> SEQUENCE: 63

Lys Leu Val Asp Lys Phe Leu Glu Asp Val Lys Lys Leu Tyr His Ser
1               5                   10                  15

Glu Ala Phe Thr Val
            20

<210> SEQ ID NO 64
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(Car)
<220> FEATURE:
<221> NAME/KEY: MOD_RES
<222> LOCATION: (5)..(5)
<223> OTHER INFORMATION: Lys(Car)
<220> FEATURE:
<221> NAME/KEY: MOD_RES
<222> LOCATION: (11)..(11)
<223> OTHER INFORMATION: Lys(Car)

<400> SEQUENCE: 64

Lys Leu Val Asp Lys Phe Leu Glu Asp Val Lys Lys Leu Tyr His Ser
1               5                   10                  15

Glu Ala Phe Thr Val
            20

<210> SEQ ID NO 65
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(Car)
<220> FEATURE:
<221> NAME/KEY: MOD_RES
<222> LOCATION: (5)..(5)

<223> OTHER INFORMATION: Lys(Car)
<220> FEATURE:
<221> NAME/KEY: MOD_RES
<222> LOCATION: (12)..(12)
<223> OTHER INFORMATION: Lys(Car)

<400> SEQUENCE: 65

Lys Leu Val Asp Lys Phe Leu Glu Asp Val Lys Lys Leu Tyr His Ser
1               5                   10                  15

Glu Ala Phe Thr Val
            20

<210> SEQ ID NO 66
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(Car)
<220> FEATURE:
<221> NAME/KEY: MOD_RES
<222> LOCATION: (11)..(12)
<223> OTHER INFORMATION: Lys(Car)

<400> SEQUENCE: 66

Lys Leu Val Asp Lys Phe Leu Glu Asp Val Lys Lys Leu Tyr His Ser
1               5                   10                  15

Glu Ala Phe Thr Val
            20

<210> SEQ ID NO 67
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Lys(Car)
<220> FEATURE:
<221> NAME/KEY: MOD_RES
<222> LOCATION: (11)..(12)
<223> OTHER INFORMATION: Lys(Car)

<400> SEQUENCE: 67

Lys Leu Val Asp Lys Phe Leu Glu Asp Val Lys Lys Leu Tyr His Ser
1               5                   10                  15

Glu Ala Phe Thr Val
            20

<210> SEQ ID NO 68
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(Car)
<220> FEATURE:
<221> NAME/KEY: MOD_RES
<222> LOCATION: (5)..(5)

```
<223> OTHER INFORMATION: Lys(Car)
<220> FEATURE:
<221> NAME/KEY: MOD_RES
<222> LOCATION: (11)..(12)
<223> OTHER INFORMATION: Lys(Car)

<400> SEQUENCE: 68

Lys Leu Val Asp Lys Phe Leu Glu Asp Val Lys Lys Leu Tyr His Ser
1               5                   10                  15

Glu Ala Phe Thr Val
            20

<210> SEQ ID NO 69
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Lys(Car)

<400> SEQUENCE: 69

Thr Val Asn Phe Gly Asp Thr Glu Glu Ala Lys Lys Gln Ile Asn Asp
1               5                   10                  15

Tyr Val Glu Lys Gly
            20

<210> SEQ ID NO 70
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Lys(Car)

<400> SEQUENCE: 70

Thr Val Asn Phe Gly Asp Thr Glu Glu Ala Lys Lys Gln Ile Asn Asp
1               5                   10                  15

Tyr Val Glu Lys Gly
            20

<210> SEQ ID NO 71
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (20)..(20)
<223> OTHER INFORMATION: Lys(Car)

<400> SEQUENCE: 71

Thr Val Asn Phe Gly Asp Thr Glu Glu Ala Lys Lys Gln Ile Asn Asp
1               5                   10                  15

Tyr Val Glu Lys Gly
            20

<210> SEQ ID NO 72
```

```
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(12)
<223> OTHER INFORMATION: Lys(Car)

<400> SEQUENCE: 72

Thr Val Asn Phe Gly Asp Thr Glu Glu Ala Lys Lys Gln Ile Asn Asp
1               5                   10                  15

Tyr Val Glu Lys Gly
            20

<210> SEQ ID NO 73
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Lys(Car)
<220> FEATURE:
<221> NAME/KEY: MOD_RES
<222> LOCATION: (20)..(20)
<223> OTHER INFORMATION: Lys(Car)

<400> SEQUENCE: 73

Thr Val Asn Phe Gly Asp Thr Glu Glu Ala Lys Lys Gln Ile Asn Asp
1               5                   10                  15

Tyr Val Glu Lys Gly
            20

<210> SEQ ID NO 74
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Lys(Car)
<220> FEATURE:
<221> NAME/KEY: MOD_RES
<222> LOCATION: (20)..(20)
<223> OTHER INFORMATION: Lys(Car)

<400> SEQUENCE: 74

Thr Val Asn Phe Gly Asp Thr Glu Glu Ala Lys Lys Gln Ile Asn Asp
1               5                   10                  15

Tyr Val Glu Lys Gly
            20

<210> SEQ ID NO 75
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (11)..(12)
<223> OTHER INFORMATION: Lys(Car)
<220> FEATURE:
<221> NAME/KEY: MOD_RES
<222> LOCATION: (20)..(20)
<223> OTHER INFORMATION: Lys(Car)

<400> SEQUENCE: 75

Thr Val Asn Phe Gly Asp Thr Glu Glu Ala Lys Lys Gln Ile Asn Asp
1               5                   10                  15

Tyr Val Glu Lys Gly
            20

<210> SEQ ID NO 76
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Lys(Car)

<400> SEQUENCE: 76

Ala Lys Lys Gln Ile Asn Asp Tyr Val Glu Lys Gly Thr Gln Gly Lys
1               5                   10                  15

Ile Val Asp Leu Val
            20

<210> SEQ ID NO 77
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Lys(Car)

<400> SEQUENCE: 77

Ala Lys Lys Gln Ile Asn Asp Tyr Val Glu Lys Gly Thr Gln Gly Lys
1               5                   10                  15

Ile Val Asp Leu Val
            20

<210> SEQ ID NO 78
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Lys(Car)

<400> SEQUENCE: 78

Ala Lys Lys Gln Ile Asn Asp Tyr Val Glu Lys Gly Thr Gln Gly Lys
1               5                   10                  15

Ile Val Asp Leu Val
            20
```

```
<210> SEQ ID NO 79
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Lys(Car)

<400> SEQUENCE: 79

Ala Lys Lys Gln Ile Asn Asp Tyr Val Glu Lys Gly Thr Gln Gly Lys
1               5                   10                  15

Ile Val Asp Leu Val
            20

<210> SEQ ID NO 80
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Lys(Car)

<400> SEQUENCE: 80

Ala Lys Lys Gln Ile Asn Asp Tyr Val Glu Lys Gly Thr Gln Gly Lys
1               5                   10                  15

Ile Val Asp Leu Val
            20

<210> SEQ ID NO 81
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Lys(Car)
<220> FEATURE:
<221> NAME/KEY: MOD_RES
<222> LOCATION: (11)..(11)
<223> OTHER INFORMATION: Lys(Car)

<400> SEQUENCE: 81

Ala Lys Lys Gln Ile Asn Asp Tyr Val Glu Lys Gly Thr Gln Gly Lys
1               5                   10                  15

Ile Val Asp Leu Val
            20

<210> SEQ ID NO 82
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Lys(Car)
<220> FEATURE:
```

```
<221> NAME/KEY: MOD_RES
<222> LOCATION: (16)..(16)
<223> OTHER INFORMATION: Lys(Car)

<400> SEQUENCE: 82

Ala Lys Lys Gln Ile Asn Asp Tyr Val Glu Lys Gly Thr Gln Gly Lys
1               5                   10                  15

Ile Val Asp Leu Val
            20

<210> SEQ ID NO 83
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Lys(Car)

<400> SEQUENCE: 83

Ala Lys Lys Gln Ile Asn Asp Tyr Val Glu Lys Gly Thr Gln Gly Lys
1               5                   10                  15

Ile Val Asp Leu Val
            20

<210> SEQ ID NO 84
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Lys(Car)

<400> SEQUENCE: 84

Ala Lys Lys Gln Ile Asn Asp Tyr Val Glu Lys Gly Thr Gln Gly Lys
1               5                   10                  15

Ile Val Asp Leu Val
            20

<210> SEQ ID NO 85
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Lys(Car)
<220> FEATURE:
<221> NAME/KEY: MOD_RES
<222> LOCATION: (16)..(16)
<223> OTHER INFORMATION: Lys(Car)

<400> SEQUENCE: 85

Ala Lys Lys Gln Ile Asn Asp Tyr Val Glu Lys Gly Thr Gln Gly Lys
1               5                   10                  15

Ile Val Asp Leu Val
            20
```

<210> SEQ ID NO 86
<211> LENGTH: 21
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (11)..(11)
<223> OTHER INFORMATION: Lys(Car)
<220> FEATURE:
<221> NAME/KEY: MOD_RES
<222> LOCATION: (16)..(16)
<223> OTHER INFORMATION: Lys(Car)

<400> SEQUENCE: 86

Ala Lys Lys Gln Ile Asn Asp Tyr Val Glu Lys Gly Thr Gln Gly Lys
1               5                   10                  15

Ile Val Asp Leu Val
            20

<210> SEQ ID NO 87
<211> LENGTH: 21
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (2)..(3)
<223> OTHER INFORMATION: Lys(Car)
<220> FEATURE:
<221> NAME/KEY: MOD_RES
<222> LOCATION: (11)..(11)
<223> OTHER INFORMATION: Lys(Car)

<400> SEQUENCE: 87

Ala Lys Lys Gln Ile Asn Asp Tyr Val Glu Lys Gly Thr Gln Gly Lys
1               5                   10                  15

Ile Val Asp Leu Val
            20

<210> SEQ ID NO 88
<211> LENGTH: 21
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (2)..(3)
<223> OTHER INFORMATION: Lys(Car)
<220> FEATURE:
<221> NAME/KEY: MOD_RES
<222> LOCATION: (16)..(16)
<223> OTHER INFORMATION: Lys(Car)

<400> SEQUENCE: 88

Ala Lys Lys Gln Ile Asn Asp Tyr Val Glu Lys Gly Thr Gln Gly Lys
1               5                   10                  15

Ile Val Asp Leu Val
            20

<210> SEQ ID NO 89
<211> LENGTH: 21
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Lys(Car)
<220> FEATURE:
<221> NAME/KEY: MOD_RES
<222> LOCATION: (11)..(11)
<223> OTHER INFORMATION: Lys(Car)
<220> FEATURE:
<221> NAME/KEY: MOD_RES
<222> LOCATION: (16)..(16)
<223> OTHER INFORMATION: Lys(Car)

<400> SEQUENCE: 89

Ala Lys Lys Gln Ile Asn Asp Tyr Val Glu Lys Gly Thr Gln Gly Lys
1               5                   10                  15

Ile Val Asp Leu Val
            20

<210> SEQ ID NO 90
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Lys(Car)
<220> FEATURE:
<221> NAME/KEY: MOD_RES
<222> LOCATION: (11)..(11)
<223> OTHER INFORMATION: Lys(Car)
<220> FEATURE:
<221> NAME/KEY: MOD_RES
<222> LOCATION: (16)..(16)
<223> OTHER INFORMATION: Lys(Car)

<400> SEQUENCE: 90

Ala Lys Lys Gln Ile Asn Asp Tyr Val Glu Lys Gly Thr Gln Gly Lys
1               5                   10                  15

Ile Val Asp Leu Val
            20

<210> SEQ ID NO 91
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Lys(Car)
<220> FEATURE:
<221> NAME/KEY: MOD_RES
<222> LOCATION: (11)..(11)
<223> OTHER INFORMATION: Lys(Car)
<220> FEATURE:
<221> NAME/KEY: MOD_RES
<222> LOCATION: (16)..(16)
<223> OTHER INFORMATION: Lys(Car)

<400> SEQUENCE: 91

Ala Lys Lys Gln Ile Asn Asp Tyr Val Glu Lys Gly Thr Gln Gly Lys
1               5                   10                  15
```

Ile Val Asp Leu Val
            20

<210> SEQ ID NO 92
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Lys(Car)

<400> SEQUENCE: 92

Asn Asp Tyr Val Glu Lys Gly Thr Gln Gly Lys Ile Val Asp Leu Val
1               5                   10                  15

Lys Glu Leu Asp Arg
            20

<210> SEQ ID NO 93
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Lys(Car)

<400> SEQUENCE: 93

Asn Asp Tyr Val Glu Lys Gly Thr Gln Gly Lys Ile Val Asp Leu Val
1               5                   10                  15

Lys Glu Leu Asp Arg
            20

<210> SEQ ID NO 94
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: Lys(Car)

<400> SEQUENCE: 94

Asn Asp Tyr Val Glu Lys Gly Thr Gln Gly Lys Ile Val Asp Leu Val
1               5                   10                  15

Lys Glu Leu Asp Arg
            20

<210> SEQ ID NO 95
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Lys(Car)

```
<220> FEATURE:
<221> NAME/KEY: MOD_RES
<222> LOCATION: (11)..(11)
<223> OTHER INFORMATION: Lys(Car)

<400> SEQUENCE: 95

Asn Asp Tyr Val Glu Lys Gly Thr Gln Gly Lys Ile Val Asp Leu Val
1               5                   10                  15

Lys Glu Leu Asp Arg
            20

<210> SEQ ID NO 96
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Lys(Car)
<220> FEATURE:
<221> NAME/KEY: MOD_RES
<222> LOCATION: (17)..(17)
<223> OTHER INFORMATION: Lys(Car)

<400> SEQUENCE: 96

Asn Asp Tyr Val Glu Lys Gly Thr Gln Gly Lys Ile Val Asp Leu Val
1               5                   10                  15

Lys Glu Leu Asp Arg
            20

<210> SEQ ID NO 97
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Lys(Car)
<220> FEATURE:
<221> NAME/KEY: MOD_RES
<222> LOCATION: (17)..(17)
<223> OTHER INFORMATION: Lys(Car)

<400> SEQUENCE: 97

Asn Asp Tyr Val Glu Lys Gly Thr Gln Gly Lys Ile Val Asp Leu Val
1               5                   10                  15

Lys Glu Leu Asp Arg
            20

<210> SEQ ID NO 98
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Lys(Car)
<220> FEATURE:
<221> NAME/KEY: MOD_RES
<222> LOCATION: (11)..(11)
<223> OTHER INFORMATION: Lys(Car)
```

```
<220> FEATURE:
<221> NAME/KEY: MOD_RES
<222> LOCATION: (17)..(17)
<223> OTHER INFORMATION: Lys(Car)

<400> SEQUENCE: 98

Asn Asp Tyr Val Glu Lys Gly Thr Gln Gly Lys Ile Val Asp Leu Val
1               5                   10                  15
Lys Glu Leu Asp Arg
            20

<210> SEQ ID NO 99
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Lys(Car)

<400> SEQUENCE: 99

Gly Thr Gln Gly Lys Ile Val Asp Leu Val Lys Glu Leu Asp Arg Asp
1               5                   10                  15
Thr Val Phe Ala Leu
            20

<210> SEQ ID NO 100
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Lys(Car)

<400> SEQUENCE: 100

Gly Thr Gln Gly Lys Ile Val Asp Leu Val Lys Glu Leu Asp Arg Asp
1               5                   10                  15
Thr Val Phe Ala Leu
            20

<210> SEQ ID NO 101
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Lys(Car)
<220> FEATURE:
<221> NAME/KEY: MOD_RES
<222> LOCATION: (11)..(11)
<223> OTHER INFORMATION: Lys(Car)

<400> SEQUENCE: 101

Gly Thr Gln Gly Lys Ile Val Asp Leu Val Lys Glu Leu Asp Arg Asp
1               5                   10                  15
Thr Val Phe Ala Leu
            20
```

```
<210> SEQ ID NO 102
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Lys(Car)

<400> SEQUENCE: 102

Val Phe Ala Leu Val Asn Tyr Ile Phe Phe Lys Gly Lys Trp Glu Arg
1               5                   10                  15

Pro Phe Glu Val Lys
            20

<210> SEQ ID NO 103
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Lys(Car)

<400> SEQUENCE: 103

Val Phe Ala Leu Val Asn Tyr Ile Phe Phe Lys Gly Lys Trp Glu Arg
1               5                   10                  15

Pro Phe Glu Val Lys
            20

<210> SEQ ID NO 104
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (21)..(21)
<223> OTHER INFORMATION: Lys(Car)

<400> SEQUENCE: 104

Val Phe Ala Leu Val Asn Tyr Ile Phe Phe Lys Gly Lys Trp Glu Arg
1               5                   10                  15

Pro Phe Glu Val Lys
            20

<210> SEQ ID NO 105
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Lys(Car)
<220> FEATURE:
<221> NAME/KEY: MOD_RES
<222> LOCATION: (13)..(13)
```

```
<223> OTHER INFORMATION: Lys(Car)

<400> SEQUENCE: 105

Val Phe Ala Leu Val Asn Tyr Ile Phe Phe Lys Gly Lys Trp Glu Arg
1               5                   10                  15

Pro Phe Glu Val Lys
            20

<210> SEQ ID NO 106
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Lys(Car)
<220> FEATURE:
<221> NAME/KEY: MOD_RES
<222> LOCATION: (21)..(21)
<223> OTHER INFORMATION: Lys(Car)

<400> SEQUENCE: 106

Val Phe Ala Leu Val Asn Tyr Ile Phe Phe Lys Gly Lys Trp Glu Arg
1               5                   10                  15

Pro Phe Glu Val Lys
            20

<210> SEQ ID NO 107
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Lys(Car)
<220> FEATURE:
<221> NAME/KEY: MOD_RES
<222> LOCATION: (21)..(21)
<223> OTHER INFORMATION: Lys(Car)

<400> SEQUENCE: 107

Val Phe Ala Leu Val Asn Tyr Ile Phe Phe Lys Gly Lys Trp Glu Arg
1               5                   10                  15

Pro Phe Glu Val Lys
            20

<210> SEQ ID NO 108
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Lys(Car)
<220> FEATURE:
<221> NAME/KEY: MOD_RES
<222> LOCATION: (13)..(13)
<223> OTHER INFORMATION: Lys(Car)
<220> FEATURE:
<221> NAME/KEY: MOD_RES
<222> LOCATION: (21)..(21)
```

```
<223> OTHER INFORMATION: Lys(Car)

<400> SEQUENCE: 108

Val Phe Ala Leu Val Asn Tyr Ile Phe Phe Lys Gly Lys Trp Glu Arg
1               5                   10                  15

Pro Phe Glu Val Lys
            20

<210> SEQ ID NO 109
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(Car)

<400> SEQUENCE: 109

Lys Gly Lys Trp Glu Arg Pro Phe Glu Val Lys Asp Thr Glu Glu Glu
1               5                   10                  15

Asp Phe His Val Asp
            20

<210> SEQ ID NO 110
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Lys(Car)

<400> SEQUENCE: 110

Lys Gly Lys Trp Glu Arg Pro Phe Glu Val Lys Asp Thr Glu Glu Glu
1               5                   10                  15

Asp Phe His Val Asp
            20

<210> SEQ ID NO 111
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Lys(Car)

<400> SEQUENCE: 111

Lys Gly Lys Trp Glu Arg Pro Phe Glu Val Lys Asp Thr Glu Glu Glu
1               5                   10                  15

Asp Phe His Val Asp
            20

<210> SEQ ID NO 112
<211> LENGTH: 21
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(Car)
<220> FEATURE:
<221> NAME/KEY: MOD_RES
<222> LOCATION: (3)..(3)
<223> OTHER INFORMATION: Lys(Car)

<400> SEQUENCE: 112

Lys Gly Lys Trp Glu Arg Pro Phe Glu Val Lys Asp Thr Glu Glu Glu
1               5                   10                  15

Asp Phe His Val Asp
            20

<210> SEQ ID NO 113
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(Car)
<220> FEATURE:
<221> NAME/KEY: MOD_RES
<222> LOCATION: (11)..(11)
<223> OTHER INFORMATION: Lys(Car)

<400> SEQUENCE: 113

Lys Gly Lys Trp Glu Arg Pro Phe Glu Val Lys Asp Thr Glu Glu Glu
1               5                   10                  15

Asp Phe His Val Asp
            20

<210> SEQ ID NO 114
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(Car)
<220> FEATURE:
<221> NAME/KEY: MOD_RES
<222> LOCATION: (3)..(3)
<223> OTHER INFORMATION: Lys(Car)
<220> FEATURE:
<221> NAME/KEY: MOD_RES
<222> LOCATION: (11)..(11)
<223> OTHER INFORMATION: Lys(Car)

<400> SEQUENCE: 114

Lys Gly Lys Trp Glu Arg Pro Phe Glu Val Lys Asp Thr Glu Glu Glu
1               5                   10                  15

Asp Phe His Val Asp
            20

<210> SEQ ID NO 115
<211> LENGTH: 21
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Lys(Car)

<400> SEQUENCE: 115

Asp Phe His Val Asp Gln Val Thr Thr Val Lys Val Pro Met Met Lys
1               5                   10                  15

Arg Leu Gly Met Phe
            20

<210> SEQ ID NO 116
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Lys(Car)

<400> SEQUENCE: 116

Asp Phe His Val Asp Gln Val Thr Thr Val Lys Val Pro Met Met Lys
1               5                   10                  15

Arg Leu Gly Met Phe
            20

<210> SEQ ID NO 117
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Lys(Car)
<220> FEATURE:
<221> NAME/KEY: MOD_RES
<222> LOCATION: (16)..(16)
<223> OTHER INFORMATION: Lys(Car)

<400> SEQUENCE: 117

Asp Phe His Val Asp Gln Val Thr Thr Val Lys Val Pro Met Met Lys
1               5                   10                  15

Arg Leu Gly Met Phe
            20

<210> SEQ ID NO 118
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Lys(Car)

<400> SEQUENCE: 118

Gln Val Thr Thr Val Lys Val Pro Met Met Lys Arg Leu Gly Met Phe
1               5                   10                  15
```

Asn Ile Gln His Cys
        20

<210> SEQ ID NO 119
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Lys(Car)

<400> SEQUENCE: 119

Gln Val Thr Thr Val Lys Val Pro Met Met Lys Arg Leu Gly Met Phe
1               5                   10                  15

Asn Ile Gln His Cys
        20

<210> SEQ ID NO 120
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Lys(Car)
<220> FEATURE:
<221> NAME/KEY: MOD_RES
<222> LOCATION: (11)..(11)
<223> OTHER INFORMATION: Lys(Car)

<400> SEQUENCE: 120

Gln Val Thr Thr Val Lys Val Pro Met Met Lys Arg Leu Gly Met Phe
1               5                   10                  15

Asn Ile Gln His Cys
        20

<210> SEQ ID NO 121
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Lys(Car)

<400> SEQUENCE: 121

Arg Leu Gly Met Phe Asn Ile Gln His Cys Lys Lys Leu Ser Ser Trp
1               5                   10                  15

Val Leu Leu Met Lys
        20

<210> SEQ ID NO 122
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:

```
<221> NAME/KEY: MOD_RES
<222> LOCATION: (12)..(12)
<223> OTHER INFORMATION: Lys(Car)

<400> SEQUENCE: 122

Arg Leu Gly Met Phe Asn Ile Gln His Cys Lys Lys Leu Ser Ser Trp
1               5                   10                  15

Val Leu Leu Met Lys
            20

<210> SEQ ID NO 123
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (21)..(21)
<223> OTHER INFORMATION: Lys(Car)

<400> SEQUENCE: 123

Arg Leu Gly Met Phe Asn Ile Gln His Cys Lys Lys Leu Ser Ser Trp
1               5                   10                  15

Val Leu Leu Met Lys
            20

<210> SEQ ID NO 124
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(12)
<223> OTHER INFORMATION: Lys(Car)

<400> SEQUENCE: 124

Arg Leu Gly Met Phe Asn Ile Gln His Cys Lys Lys Leu Ser Ser Trp
1               5                   10                  15

Val Leu Leu Met Lys
            20

<210> SEQ ID NO 125
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Lys(Car)
<220> FEATURE:
<221> NAME/KEY: MOD_RES
<222> LOCATION: (21)..(21)
<223> OTHER INFORMATION: Lys(Car)

<400> SEQUENCE: 125

Arg Leu Gly Met Phe Asn Ile Gln His Cys Lys Lys Leu Ser Ser Trp
1               5                   10                  15

Val Leu Leu Met Lys
            20
```

```
<210> SEQ ID NO 126
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Lys(Car)
<220> FEATURE:
<221> NAME/KEY: MOD_RES
<222> LOCATION: (21)..(21)
<223> OTHER INFORMATION: Lys(Car)

<400> SEQUENCE: 126

Arg Leu Gly Met Phe Asn Ile Gln His Cys Lys Lys Leu Ser Ser Trp
1               5                   10                  15

Val Leu Leu Met Lys
            20

<210> SEQ ID NO 127
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(12)
<223> OTHER INFORMATION: Lys(Car)
<220> FEATURE:
<221> NAME/KEY: MOD_RES
<222> LOCATION: (21)..(21)
<223> OTHER INFORMATION: Lys(Car)

<400> SEQUENCE: 127

Arg Leu Gly Met Phe Asn Ile Gln His Cys Lys Lys Leu Ser Ser Trp
1               5                   10                  15

Val Leu Leu Met Lys
            20

<210> SEQ ID NO 128
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(Car)

<400> SEQUENCE: 128

Lys Lys Leu Ser Ser Trp Val Leu Leu Met Lys Tyr Leu Gly Asn Ala
1               5                   10                  15

Thr Ala Ile Phe Phe
            20

<210> SEQ ID NO 129
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (2)..(2)
<223> OTHER INFORMATION: Lys(Car)

<400> SEQUENCE: 129

Lys Lys Leu Ser Ser Trp Val Leu Leu Met Lys Tyr Leu Gly Asn Ala
1               5                   10                  15

Thr Ala Ile Phe Phe
            20

<210> SEQ ID NO 130
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Lys(Car)

<400> SEQUENCE: 130

Lys Lys Leu Ser Ser Trp Val Leu Leu Met Lys Tyr Leu Gly Asn Ala
1               5                   10                  15

Thr Ala Ile Phe Phe
            20

<210> SEQ ID NO 131
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Lys(Car)

<400> SEQUENCE: 131

Lys Lys Leu Ser Ser Trp Val Leu Leu Met Lys Tyr Leu Gly Asn Ala
1               5                   10                  15

Thr Ala Ile Phe Phe
            20

<210> SEQ ID NO 132
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(Car)
<220> FEATURE:
<221> NAME/KEY: MOD_RES
<222> LOCATION: (11)..(11)
<223> OTHER INFORMATION: Lys(Car)

<400> SEQUENCE: 132

Lys Lys Leu Ser Ser Trp Val Leu Leu Met Lys Tyr Leu Gly Asn Ala
1               5                   10                  15

Thr Ala Ile Phe Phe
            20
```

<210> SEQ ID NO 133
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Lys(Car)
<220> FEATURE:
<221> NAME/KEY: MOD_RES
<222> LOCATION: (11)..(11)
<223> OTHER INFORMATION: Lys(Car)

<400> SEQUENCE: 133

Lys Lys Leu Ser Ser Trp Val Leu Leu Met Lys Tyr Leu Gly Asn Ala
1               5                   10                  15

Thr Ala Ile Phe Phe
            20

<210> SEQ ID NO 134
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Lys(Car)
<220> FEATURE:
<221> NAME/KEY: MOD_RES
<222> LOCATION: (11)..(11)
<223> OTHER INFORMATION: Lys(Car)

<400> SEQUENCE: 134

Lys Lys Leu Ser Ser Trp Val Leu Leu Met Lys Tyr Leu Gly Asn Ala
1               5                   10                  15

Thr Ala Ile Phe Phe
            20

<210> SEQ ID NO 135
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Lys(Car)

<400> SEQUENCE: 135

Thr Ala Ile Phe Phe Leu Pro Asp Glu Gly Lys Leu Gln His Leu Glu
1               5                   10                  15

Asn Glu Leu Thr His
            20

<210> SEQ ID NO 136
<211> LENGTH: 21
<212> TYPE: PRT
<213> ORGANISM: Artificial Sequence
<220> FEATURE:
<223> OTHER INFORMATION: Description of Artificial Sequence: Synthetic

```
                              peptide
<220> FEATURE:
<221> NAME/KEY: MOD_RES
<222> LOCATION: (11)..(11)
<223> OTHER INFORMATION: Lys(Car)

<400> SEQUENCE: 136

Glu Asn Glu Leu Thr His Asp Ile Ile Thr Lys Phe Leu Glu Asn Glu
1               5                   10                  15

Asp Arg Arg Ser Ala
            20

<210> SEQ ID NO 137
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Lys(Car)

<400> SEQUENCE: 137

Asp Arg Arg Ser Ala Ser Leu His Leu Pro Lys Leu Ser Ile Thr Gly
1               5                   10                  15

Thr Tyr Asp Leu Lys
            20

<210> SEQ ID NO 138
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (21)..(21)
<223> OTHER INFORMATION: Lys(Car)

<400> SEQUENCE: 138

Asp Arg Arg Ser Ala Ser Leu His Leu Pro Lys Leu Ser Ile Thr Gly
1               5                   10                  15

Thr Tyr Asp Leu Lys
            20

<210> SEQ ID NO 139
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Lys(Car)
<220> FEATURE:
<221> NAME/KEY: MOD_RES
<222> LOCATION: (21)..(21)
<223> OTHER INFORMATION: Lys(Car)

<400> SEQUENCE: 139

Asp Arg Arg Ser Ala Ser Leu His Leu Pro Lys Leu Ser Ile Thr Gly
1               5                   10                  15

Thr Tyr Asp Leu Lys
```

```
              20

<210> SEQ ID NO 140
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(Car)

<400> SEQUENCE: 140

Lys Leu Ser Ile Thr Gly Thr Tyr Asp Leu Lys Ser Val Leu Gly Gln
1               5                   10                  15

Leu Gly Ile Thr Lys
            20

<210> SEQ ID NO 141
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Lys(Car)

<400> SEQUENCE: 141

Lys Leu Ser Ile Thr Gly Thr Tyr Asp Leu Lys Ser Val Leu Gly Gln
1               5                   10                  15

Leu Gly Ile Thr Lys
            20

<210> SEQ ID NO 142
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (21)..(21)
<223> OTHER INFORMATION: Lys(Car)

<400> SEQUENCE: 142

Lys Leu Ser Ile Thr Gly Thr Tyr Asp Leu Lys Ser Val Leu Gly Gln
1               5                   10                  15

Leu Gly Ile Thr Lys
            20

<210> SEQ ID NO 143
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(Car)
<220> FEATURE:
<221> NAME/KEY: MOD_RES
```

```
<222> LOCATION: (11)..(11)
<223> OTHER INFORMATION: Lys(Car)

<400> SEQUENCE: 143

Lys Leu Ser Ile Thr Gly Thr Tyr Asp Leu Lys Ser Val Leu Gly Gln
1               5                   10                  15

Leu Gly Ile Thr Lys
            20

<210> SEQ ID NO 144
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(Car)
<220> FEATURE:
<221> NAME/KEY: MOD_RES
<222> LOCATION: (21)..(21)
<223> OTHER INFORMATION: Lys(Car)

<400> SEQUENCE: 144

Lys Leu Ser Ile Thr Gly Thr Tyr Asp Leu Lys Ser Val Leu Gly Gln
1               5                   10                  15

Leu Gly Ile Thr Lys
            20

<210> SEQ ID NO 145
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Lys(Car)
<220> FEATURE:
<221> NAME/KEY: MOD_RES
<222> LOCATION: (21)..(21)
<223> OTHER INFORMATION: Lys(Car)

<400> SEQUENCE: 145

Lys Leu Ser Ile Thr Gly Thr Tyr Asp Leu Lys Ser Val Leu Gly Gln
1               5                   10                  15

Leu Gly Ile Thr Lys
            20

<210> SEQ ID NO 146
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(Car)
<220> FEATURE:
<221> NAME/KEY: MOD_RES
<222> LOCATION: (11)..(11)
<223> OTHER INFORMATION: Lys(Car)
<220> FEATURE:
<221> NAME/KEY: MOD_RES
```

```
<222> LOCATION: (21)..(21)
<223> OTHER INFORMATION: Lys(Car)

<400> SEQUENCE: 146

Lys Leu Ser Ile Thr Gly Thr Tyr Asp Leu Lys Ser Val Leu Gly Gln
1               5                   10                  15

Leu Gly Ile Thr Lys
            20

<210> SEQ ID NO 147
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(Car)

<400> SEQUENCE: 147

Lys Ser Val Leu Gly Gln Leu Gly Ile Thr Lys Val Phe Ser Asn Gly
1               5                   10                  15

Ala Asp Leu Ser Gly
            20

<210> SEQ ID NO 148
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Lys(Car)

<400> SEQUENCE: 148

Lys Ser Val Leu Gly Gln Leu Gly Ile Thr Lys Val Phe Ser Asn Gly
1               5                   10                  15

Ala Asp Leu Ser Gly
            20

<210> SEQ ID NO 149
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(Car)
<220> FEATURE:
<221> NAME/KEY: MOD_RES
<222> LOCATION: (11)..(11)
<223> OTHER INFORMATION: Lys(Car)

<400> SEQUENCE: 149

Lys Ser Val Leu Gly Gln Leu Gly Ile Thr Lys Val Phe Ser Asn Gly
1               5                   10                  15

Ala Asp Leu Ser Gly
            20
```

<210> SEQ ID NO 150
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Lys(Car)

<400> SEQUENCE: 150

Leu Ser Gly Val Thr Glu Glu Ala Pro Leu Lys Leu Ser Lys Ala Val
1               5                   10                  15

His Lys Ala Val Leu
            20

<210> SEQ ID NO 151
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Lys(Car)

<400> SEQUENCE: 151

Leu Ser Gly Val Thr Glu Glu Ala Pro Leu Lys Leu Ser Lys Ala Val
1               5                   10                  15

His Lys Ala Val Leu
            20

<210> SEQ ID NO 152
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Lys(Car)

<400> SEQUENCE: 152

Leu Ser Gly Val Thr Glu Glu Ala Pro Leu Lys Leu Ser Lys Ala Val
1               5                   10                  15

His Lys Ala Val Leu
            20

<210> SEQ ID NO 153
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Lys(Car)
<220> FEATURE:
<221> NAME/KEY: MOD_RES
<222> LOCATION: (14)..(14)
<223> OTHER INFORMATION: Lys(Car)

```
<400> SEQUENCE: 153

Leu Ser Gly Val Thr Glu Glu Ala Pro Leu Lys Leu Ser Lys Ala Val
1               5                   10                  15

His Lys Ala Val Leu
            20

<210> SEQ ID NO 154
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Lys(Car)
<220> FEATURE:
<221> NAME/KEY: MOD_RES
<222> LOCATION: (18)..(18)
<223> OTHER INFORMATION: Lys(Car)

<400> SEQUENCE: 154

Leu Ser Gly Val Thr Glu Glu Ala Pro Leu Lys Leu Ser Lys Ala Val
1               5                   10                  15

His Lys Ala Val Leu
            20

<210> SEQ ID NO 155
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Lys(Car)
<220> FEATURE:
<221> NAME/KEY: MOD_RES
<222> LOCATION: (18)..(18)
<223> OTHER INFORMATION: Lys(Car)

<400> SEQUENCE: 155

Leu Ser Gly Val Thr Glu Glu Ala Pro Leu Lys Leu Ser Lys Ala Val
1               5                   10                  15

His Lys Ala Val Leu
            20

<210> SEQ ID NO 156
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Lys(Car)
<220> FEATURE:
<221> NAME/KEY: MOD_RES
<222> LOCATION: (14)..(14)
<223> OTHER INFORMATION: Lys(Car)
<220> FEATURE:
<221> NAME/KEY: MOD_RES
<222> LOCATION: (18)..(18)
<223> OTHER INFORMATION: Lys(Car)
```

```
<400> SEQUENCE: 156

Leu Ser Gly Val Thr Glu Glu Ala Pro Leu Lys Leu Ser Lys Ala Val
1               5                   10                  15

His Lys Ala Val Leu
            20

<210> SEQ ID NO 157
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Lys(Car)

<400> SEQUENCE: 157

Val Thr Glu Glu Ala Pro Leu Lys Leu Ser Lys Ala Val His Lys Ala
1               5                   10                  15

Val Leu Thr Ile Asp
            20

<210> SEQ ID NO 158
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Lys(Car)

<400> SEQUENCE: 158

Val Thr Glu Glu Ala Pro Leu Lys Leu Ser Lys Ala Val His Lys Ala
1               5                   10                  15

Val Leu Thr Ile Asp
            20

<210> SEQ ID NO 159
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Lys(Car)

<400> SEQUENCE: 159

Val Thr Glu Glu Ala Pro Leu Lys Leu Ser Lys Ala Val His Lys Ala
1               5                   10                  15

Val Leu Thr Ile Asp
            20

<210> SEQ ID NO 160
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (8)..(8)
<223> OTHER INFORMATION: Lys(Car)
<220> FEATURE:
<221> NAME/KEY: MOD_RES
<222> LOCATION: (11)..(11)
<223> OTHER INFORMATION: Lys(Car)

<400> SEQUENCE: 160

Val Thr Glu Glu Ala Pro Leu Lys Leu Ser Lys Ala Val His Lys Ala
1               5                   10                  15

Val Leu Thr Ile Asp
            20

<210> SEQ ID NO 161
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Lys(Car)
<220> FEATURE:
<221> NAME/KEY: MOD_RES
<222> LOCATION: (15)..(15)
<223> OTHER INFORMATION: Lys(Car)

<400> SEQUENCE: 161

Val Thr Glu Glu Ala Pro Leu Lys Leu Ser Lys Ala Val His Lys Ala
1               5                   10                  15

Val Leu Thr Ile Asp
            20

<210> SEQ ID NO 162
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Lys(Car)
<220> FEATURE:
<221> NAME/KEY: MOD_RES
<222> LOCATION: (15)..(15)
<223> OTHER INFORMATION: Lys(Car)

<400> SEQUENCE: 162

Val Thr Glu Glu Ala Pro Leu Lys Leu Ser Lys Ala Val His Lys Ala
1               5                   10                  15

Val Leu Thr Ile Asp
            20

<210> SEQ ID NO 163
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Lys(Car)
```

```
<220> FEATURE:
<221> NAME/KEY: MOD_RES
<222> LOCATION: (11)..(11)
<223> OTHER INFORMATION: Lys(Car)
<220> FEATURE:
<221> NAME/KEY: MOD_RES
<222> LOCATION: (15)..(15)
<223> OTHER INFORMATION: Lys(Car)

<400> SEQUENCE: 163

Val Thr Glu Glu Ala Pro Leu Lys Leu Ser Lys Ala Val His Lys Ala
1               5                   10                  15

Val Leu Thr Ile Asp
            20

<210> SEQ ID NO 164
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Lys(Car)

<400> SEQUENCE: 164

Ala Pro Leu Lys Leu Ser Lys Ala Val His Lys Ala Val Leu Thr Ile
1               5                   10                  15

Asp Glu Lys Gly Thr
            20

<210> SEQ ID NO 165
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Lys(Car)

<400> SEQUENCE: 165

Ala Pro Leu Lys Leu Ser Lys Ala Val His Lys Ala Val Leu Thr Ile
1               5                   10                  15

Asp Glu Lys Gly Thr
            20

<210> SEQ ID NO 166
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Lys(Car)

<400> SEQUENCE: 166

Ala Pro Leu Lys Leu Ser Lys Ala Val His Lys Ala Val Leu Thr Ile
1               5                   10                  15

Asp Glu Lys Gly Thr
            20
```

```
<210> SEQ ID NO 167
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Lys(Car)

<400> SEQUENCE: 167

Ala Pro Leu Lys Leu Ser Lys Ala Val His Lys Ala Val Leu Thr Ile
1               5                   10                  15

Asp Glu Lys Gly Thr
            20

<210> SEQ ID NO 168
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Lys(Car)
<220> FEATURE:
<221> NAME/KEY: MOD_RES
<222> LOCATION: (7)..(7)
<223> OTHER INFORMATION: Lys(Car)

<400> SEQUENCE: 168

Ala Pro Leu Lys Leu Ser Lys Ala Val His Lys Ala Val Leu Thr Ile
1               5                   10                  15

Asp Glu Lys Gly Thr
            20

<210> SEQ ID NO 169
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Lys(Car)
<220> FEATURE:
<221> NAME/KEY: MOD_RES
<222> LOCATION: (11)..(11)
<223> OTHER INFORMATION: Lys(Car)

<400> SEQUENCE: 169

Ala Pro Leu Lys Leu Ser Lys Ala Val His Lys Ala Val Leu Thr Ile
1               5                   10                  15

Asp Glu Lys Gly Thr
            20

<210> SEQ ID NO 170
<211> LENGTH: 21
<212> TYPE: PRT
<213> ORGANISM: Artificial Sequence
<220> FEATURE:
<223> OTHER INFORMATION: Description of Artificial Sequence: Synthetic
```

```
            peptide
<220> FEATURE:
<221> NAME/KEY: MOD_RES
<222> LOCATION: (4)..(4)
<223> OTHER INFORMATION: Lys(Car)
<220> FEATURE:
<221> NAME/KEY: MOD_RES
<222> LOCATION: (7)..(7)
<223> OTHER INFORMATION: Lys(Car)

<400> SEQUENCE: 170

Ala Pro Leu Lys Leu Ser Lys Ala Val His Lys Ala Val Leu Thr Ile
1               5                   10                  15

Asp Glu Lys Gly Thr
            20

<210> SEQ ID NO 171
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Lys(Car)
<220> FEATURE:
<221> NAME/KEY: MOD_RES
<222> LOCATION: (19)..(19)
<223> OTHER INFORMATION: Lys(Car)

<400> SEQUENCE: 171

Ala Pro Leu Lys Leu Ser Lys Ala Val His Lys Ala Val Leu Thr Ile
1               5                   10                  15

Asp Glu Lys Gly Thr
            20

<210> SEQ ID NO 172
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Lys(Car)
<220> FEATURE:
<221> NAME/KEY: MOD_RES
<222> LOCATION: (19)..(19)
<223> OTHER INFORMATION: Lys(Car)

<400> SEQUENCE: 172

Ala Pro Leu Lys Leu Ser Lys Ala Val His Lys Ala Val Leu Thr Ile
1               5                   10                  15

Asp Glu Lys Gly Thr
            20

<210> SEQ ID NO 173
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
```

```
<223> OTHER INFORMATION: Lys(Car)
<220> FEATURE:
<221> NAME/KEY: MOD_RES
<222> LOCATION: (7)..(7)
<223> OTHER INFORMATION: Lys(Car)
<220> FEATURE:
<221> NAME/KEY: MOD_RES
<222> LOCATION: (11)..(11)
<223> OTHER INFORMATION: Lys(Car)

<400> SEQUENCE: 173

Ala Pro Leu Lys Leu Ser Lys Ala Val His Lys Ala Val Leu Thr Ile
1               5                   10                  15

Asp Glu Lys Gly Thr
            20

<210> SEQ ID NO 174
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Lys(Car)
<220> FEATURE:
<221> NAME/KEY: MOD_RES
<222> LOCATION: (7)..(7)
<223> OTHER INFORMATION: Lys(Car)
<220> FEATURE:
<221> NAME/KEY: MOD_RES
<222> LOCATION: (19)..(19)
<223> OTHER INFORMATION: Lys(Car)

<400> SEQUENCE: 174

Ala Pro Leu Lys Leu Ser Lys Ala Val His Lys Ala Val Leu Thr Ile
1               5                   10                  15

Asp Glu Lys Gly Thr
            20

<210> SEQ ID NO 175
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Lys(Car)
<220> FEATURE:
<221> NAME/KEY: MOD_RES
<222> LOCATION: (11)..(11)
<223> OTHER INFORMATION: Lys(Car)
<220> FEATURE:
<221> NAME/KEY: MOD_RES
<222> LOCATION: (19)..(19)
<223> OTHER INFORMATION: Lys(Car)

<400> SEQUENCE: 175

Ala Pro Leu Lys Leu Ser Lys Ala Val His Lys Ala Val Leu Thr Ile
1               5                   10                  15

Asp Glu Lys Gly Thr
            20

<210> SEQ ID NO 176
<211> LENGTH: 21
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Lys(Car)
<220> FEATURE:
<221> NAME/KEY: MOD_RES
<222> LOCATION: (11)..(11)
<223> OTHER INFORMATION: Lys(Car)
<220> FEATURE:
<221> NAME/KEY: MOD_RES
<222> LOCATION: (19)..(19)
<223> OTHER INFORMATION: Lys(Car)

<400> SEQUENCE: 176

Ala Pro Leu Lys Leu Ser Lys Ala Val His Lys Ala Val Leu Thr Ile
1               5                   10                  15

Asp Glu Lys Gly Thr
            20

<210> SEQ ID NO 177
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Lys(Car)
<220> FEATURE:
<221> NAME/KEY: MOD_RES
<222> LOCATION: (7)..(7)
<223> OTHER INFORMATION: Lys(Car)
<220> FEATURE:
<221> NAME/KEY: MOD_RES
<222> LOCATION: (11)..(11)
<223> OTHER INFORMATION: Lys(Car)
<220> FEATURE:
<221> NAME/KEY: MOD_RES
<222> LOCATION: (19)..(19)
<223> OTHER INFORMATION: Lys(Car)

<400> SEQUENCE: 177

Ala Pro Leu Lys Leu Ser Lys Ala Val His Lys Ala Val Leu Thr Ile
1               5                   10                  15

Asp Glu Lys Gly Thr
            20

<210> SEQ ID NO 178
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Lys(Car)

<400> SEQUENCE: 178

Val His Lys Ala Val Leu Thr Ile Asp Glu Lys Gly Thr Glu Ala Ala
1               5                   10                  15

Gly Ala Met Phe Leu
            20
```

```
<210> SEQ ID NO 179
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Lys(Car)

<400> SEQUENCE: 179

Val His Lys Ala Val Leu Thr Ile Asp Glu Lys Gly Thr Glu Ala Ala
1               5                   10                  15

Gly Ala Met Phe Leu
            20

<210> SEQ ID NO 180
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Lys(Car)
<220> FEATURE:
<221> NAME/KEY: MOD_RES
<222> LOCATION: (11)..(11)
<223> OTHER INFORMATION: Lys(Car)

<400> SEQUENCE: 180

Val His Lys Ala Val Leu Thr Ile Asp Glu Lys Gly Thr Glu Ala Ala
1               5                   10                  15

Gly Ala Met Phe Leu
            20

<210> SEQ ID NO 181
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Lys(Car)

<400> SEQUENCE: 181

Ala Ile Pro Met Ser Ile Pro Pro Glu Val Lys Phe Asn Lys Pro Phe
1               5                   10                  15

Val Phe Leu Met Ile
            20

<210> SEQ ID NO 182
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
```

<223> OTHER INFORMATION: Lys(Car)

<400> SEQUENCE: 182

Ala Ile Pro Met Ser Ile Pro Pro Glu Val Lys Phe Asn Lys Pro Phe
1               5                   10                  15

Val Phe Leu Met Ile
            20

<210> SEQ ID NO 183
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Lys(Car)
<220> FEATURE:
<221> NAME/KEY: MOD_RES
<222> LOCATION: (14)..(14)
<223> OTHER INFORMATION: Lys(Car)

<400> SEQUENCE: 183

Ala Ile Pro Met Ser Ile Pro Pro Glu Val Lys Phe Asn Lys Pro Phe
1               5                   10                  15

Val Phe Leu Met Ile
            20

<210> SEQ ID NO 184
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Lys(Car)

<400> SEQUENCE: 184

Met Ser Ile Pro Pro Glu Val Lys Phe Asn Lys Pro Phe Val Phe Leu
1               5                   10                  15

Met Ile Glu Gln Asn
            20

<210> SEQ ID NO 185
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Lys(Car)

<400> SEQUENCE: 185

Met Ser Ile Pro Pro Glu Val Lys Phe Asn Lys Pro Phe Val Phe Leu
1               5                   10                  15

Met Ile Glu Gln Asn
            20

<210> SEQ ID NO 186

```
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Lys(Car)
<220> FEATURE:
<221> NAME/KEY: MOD_RES
<222> LOCATION: (11)..(11)
<223> OTHER INFORMATION: Lys(Car)

<400> SEQUENCE: 186

Met Ser Ile Pro Pro Glu Val Lys Phe Asn Lys Pro Phe Val Phe Leu
1               5                   10                  15

Met Ile Glu Gln Asn
            20

<210> SEQ ID NO 187
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Lys(Car)

<400> SEQUENCE: 187

Phe Val Phe Leu Met Ile Glu Gln Asn Thr Lys Ser Pro Leu Phe Met
1               5                   10                  15

Gly Lys Val Val Asn
            20

<210> SEQ ID NO 188
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Lys(Car)

<400> SEQUENCE: 188

Phe Val Phe Leu Met Ile Glu Gln Asn Thr Lys Ser Pro Leu Phe Met
1               5                   10                  15

Gly Lys Val Val Asn
            20

<210> SEQ ID NO 189
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Lys(Car)
<220> FEATURE:
<221> NAME/KEY: MOD_RES
```

```
<222> LOCATION: (18)..(18)
<223> OTHER INFORMATION: Lys(Car)

<400> SEQUENCE: 189

Phe Val Phe Leu Met Ile Glu Gln Asn Thr Lys Ser Pro Leu Phe Met
1               5                   10                  15

Gly Lys Val Val Asn
            20

<210> SEQ ID NO 190
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Lys(Car)

<400> SEQUENCE: 190

Glu Gln Asn Thr Lys Ser Pro Leu Phe Met Gly Lys Val Val Asn Pro
1               5                   10                  15

Thr Gln Lys Ala Ala
            20

<210> SEQ ID NO 191
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Lys(Car)

<400> SEQUENCE: 191

Glu Gln Asn Thr Lys Ser Pro Leu Phe Met Gly Lys Val Val Asn Pro
1               5                   10                  15

Thr Gln Lys Ala Ala
            20

<210> SEQ ID NO 192
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Lys(Car)

<400> SEQUENCE: 192

Glu Gln Asn Thr Lys Ser Pro Leu Phe Met Gly Lys Val Val Asn Pro
1               5                   10                  15

Thr Gln Lys Ala Ala
            20

<210> SEQ ID NO 193
<211> LENGTH: 21
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Lys(Car)
<220> FEATURE:
<221> NAME/KEY: MOD_RES
<222> LOCATION: (12)..(12)
<223> OTHER INFORMATION: Lys(Car)

<400> SEQUENCE: 193

Glu Gln Asn Thr Lys Ser Pro Leu Phe Met Gly Lys Val Val Asn Pro
1               5                   10                  15

Thr Gln Lys Ala Ala
            20

<210> SEQ ID NO 194
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Lys(Car)
<220> FEATURE:
<221> NAME/KEY: MOD_RES
<222> LOCATION: (19)..(19)
<223> OTHER INFORMATION: Lys(Car)

<400> SEQUENCE: 194

Glu Gln Asn Thr Lys Ser Pro Leu Phe Met Gly Lys Val Val Asn Pro
1               5                   10                  15

Thr Gln Lys Ala Ala
            20

<210> SEQ ID NO 195
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Lys(Car)
<220> FEATURE:
<221> NAME/KEY: MOD_RES
<222> LOCATION: (19)..(19)
<223> OTHER INFORMATION: Lys(Car)

<400> SEQUENCE: 195

Glu Gln Asn Thr Lys Ser Pro Leu Phe Met Gly Lys Val Val Asn Pro
1               5                   10                  15

Thr Gln Lys Ala Ala
            20

<210> SEQ ID NO 196
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (5)..(5)
<223> OTHER INFORMATION: Lys(Car)
<220> FEATURE:
<221> NAME/KEY: MOD_RES
<222> LOCATION: (12)..(12)
<223> OTHER INFORMATION: Lys(Car)
<220> FEATURE:
<221> NAME/KEY: MOD_RES
<222> LOCATION: (19)..(19)
<223> OTHER INFORMATION: Lys(Car)

<400> SEQUENCE: 196

Glu Gln Asn Thr Lys Ser Pro Leu Phe Met Gly Lys Val Val Asn Pro
1               5                   10                  15

Thr Gln Lys Ala Ala
            20

<210> SEQ ID NO 197
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Lys(Car)

<400> SEQUENCE: 197

Ala Leu Val Asn Tyr Ile Phe Phe Lys Gly Lys Trp Glu Arg Pro Phe
1               5                   10                  15

Glu Val Lys Asp Thr
            20

<210> SEQ ID NO 198
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Lys(Car)

<400> SEQUENCE: 198

Ala Leu Val Asn Tyr Ile Phe Phe Lys Gly Lys Trp Glu Arg Pro Phe
1               5                   10                  15

Glu Val Lys Asp Thr
            20

<210> SEQ ID NO 199
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Lys(Car)

<400> SEQUENCE: 199

Ala Leu Val Asn Tyr Ile Phe Phe Lys Gly Lys Trp Glu Arg Pro Phe
1               5                   10                  15
```

Glu Val Lys Asp Thr
            20

<210> SEQ ID NO 200
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Lys(Car)
<220> FEATURE:
<221> NAME/KEY: MOD_RES
<222> LOCATION: (11)..(11)
<223> OTHER INFORMATION: Lys(Car)

<400> SEQUENCE: 200

Ala Leu Val Asn Tyr Ile Phe Phe Lys Gly Lys Trp Glu Arg Pro Phe
1               5                   10                  15

Glu Val Lys Asp Thr
            20

<210> SEQ ID NO 201
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Lys(Car)
<220> FEATURE:
<221> NAME/KEY: MOD_RES
<222> LOCATION: (19)..(19)
<223> OTHER INFORMATION: Lys(Car)

<400> SEQUENCE: 201

Ala Leu Val Asn Tyr Ile Phe Phe Lys Gly Lys Trp Glu Arg Pro Phe
1               5                   10                  15

Glu Val Lys Asp Thr
            20

<210> SEQ ID NO 202
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Lys(Car)
<220> FEATURE:
<221> NAME/KEY: MOD_RES
<222> LOCATION: (19)..(19)
<223> OTHER INFORMATION: Lys(Car)

<400> SEQUENCE: 202

Ala Leu Val Asn Tyr Ile Phe Phe Lys Gly Lys Trp Glu Arg Pro Phe
1               5                   10                  15

Glu Val Lys Asp Thr
            20

```
<210> SEQ ID NO 203
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Lys(Car)
<220> FEATURE:
<221> NAME/KEY: MOD_RES
<222> LOCATION: (11)..(11)
<223> OTHER INFORMATION: Lys(Car)
<220> FEATURE:
<221> NAME/KEY: MOD_RES
<222> LOCATION: (19)..(19)
<223> OTHER INFORMATION: Lys(Car)

<400> SEQUENCE: 203

Ala Leu Val Asn Tyr Ile Phe Phe Lys Gly Lys Trp Glu Arg Pro Phe
1               5                   10                  15

Glu Val Lys Asp Thr
            20
```

COMPOSITIONS AND METHODS FOR THE DIAGNOSIS OF RHEUMATOID ARTHRITIS

CROSS-REFERENCE TO RELATED APPLICATIONS

This application is a continuation of U.S. application Ser. No. 14/806,515, filed Jul. 22, 2015, which claims the benefit of and priority to U.S. Provisional Application No. 62/028,270 filed Jul. 23, 2014, the entire contents of each of which are incorporated herein by reference in their entireties.

The content of the following submission on ASCII text file is incorporated herein by reference in its entirety: a computer readable form (CRF) of the Sequence Listing, entitled 13510-027-999_SEQ_LISTING.txt, of file size 87,946 bytes, created on Sep. 1, 2017.

FIELD

The present disclosure relates to the field of molecular biology and more specifically to methods for detecting anti-carbamylated protein (anti-CarP) antibodies in the serum of rheumatoid arthritis (RA) patients.

BACKGROUND

Rheumatoid arthritis (RA) is an autoimmune disease that primarily attacks synovial joints. Recent research has shown that the RA patient population is heterogeneous and that certain autoantibodies can be used as biomarkers to classify subgroups of RA patients and predict different courses of disease progression for different patient subgroups.

Autoantibodies directed against citrullinated proteins (ACPAs) are established biomarkers in RA and are, e.g., included in the 2010 American College of Rheumatology/European League Against Rheumatism criteria for RA (see, e.g., Aletaha D. et al., 2010, *Rheumatoid arthritis classification criteria: an American College of Rheumatology/European League Against Rheumatism collaborative initiative*. Ann. Rheum. Dis. 2010, 69, 1580-1588). RA patients forming ACPAs generally experience a more severe disease course, have a lower chance to enter drug-free remission and are subject to a different set of environmental and genetic risk factors than RA patients not forming ACPAs.

Recently, a second class of autoantibody biomarkers for RA has been discovered that complements the diagnostic and prognostic information provided by ACPAs. Research has shown that a more severe disease course can be predicted in ACPA-negative RA patients based on the detection of autoantibodies directed against carbamylated proteins (anti-CarP antibodies). The presence of anti-CarP antibodies is associated with more radiological progression of RA and with the conversion of non-inflammatory joint pain (arthralgia) to clinically manifested RA, which can ultimately result in a chronic, systemic inflammatory disorder.

Anti-CarP antibodies can be detected in serum samples many years prior to the onset of clinical symptoms of RA. Early detection of anti-CarP antibodies can enable at-risk RA candidates or early-stage RA patients to take preventative measures to ameliorate, delay or avert the onset of RA. However, the further development of anti-CarP antibodies as diagnostic and prognostic biomarkers in RA is hindered by the limitations of existing anti-CarP antibody assays.

Thus there is a need for new methods to detect anti-CarP antibodies. The present disclosure addresses this need by providing new compositions and methods for the development of anti-CarP antibody assays and provides related advantages as well.

SUMMARY

The present disclosure provides compositions and methods for the diagnosis and prognosis of rheumatoid arthritis.

In one aspect, the disclosure provides purified polypeptides including an in vitro carbamylated human alpha 1 antitrypsin (hA1AT), or a fragment thereof.

In some embodiments, the purified polypeptide is a purified recombinant polypeptide encoded by cDNA.

In some embodiments, the purified polypeptide is hA1AT, or a fragment thereof, purified from blood, serum, plasma, urine, or synovial fluid.

In some embodiments, the hA1AT, or fragment thereof, includes the amino acid sequence of SEQ ID NO:1.

In some embodiments, the hA1AT, or fragment thereof, has greater than 70%, greater than 75%, greater than 80%, greater than 85%, greater than 90%, greater than 95%, greater than 96%, greater than 97%, greater than 98%, or greater than 99% sequence identity to SEQ ID NO:1.

In some embodiments, the hA1AT, or fragment thereof, includes a fragment of 8 or more contiguous amino acids of SEQ ID NO:1.

In some embodiments, the hA1AT, or fragment thereof, includes a fragment of 8 or more contiguous amino acids with greater than 80%, greater than 85%, greater than 90%, greater than 95%, greater than 96%, greater than 97%, greater than 98%, or greater than 99% sequence identity to SEQ ID NO:1.

In some embodiments, the hA1AT, or fragment thereof, includes the amino acid sequence of any one of SEQ ID NOs:3-32.

In some embodiments, the in vitro carbamylated hA1AT, or fragment thereof, includes the amino acid sequence of any one of SEQ ID NO:33-203.

In some embodiments, more than 10%, more than 20%, more than 30%, more than 40%, more than 50%, more than 60%, more than 70%, more than 80%, more than 90%, more than 95%, or more than 99% of lysine residues in the hA1AT, or fragment thereof, are carbamylated.

In some embodiments, the purified polypeptide is a plurality of purified polypeptides. In some embodiments, more than 10%, more than 20%, more than 30%, more than 40%, more than 50%, more than 60%, more than 70%, more than 80%, more than 90%, more than 95%, or more than 99% of lysine residues are carbamylated in the hA1AT, or fragment thereof, of more than 10%, more than 20%, more than 30%, more than 40%, more than 50%, more than 60%, more than 70%, more than 80%, more than 90%, more than 95%, or more than 99% of purified polypeptides in the plurality of purified polypeptides.

In some embodiments, the hA1AT, or fragment thereof, includes one or more anti-carbamylated protein (anti-CarP) antibody binding sites, each of which can independently be in a carbamylated state or uncarbamylated state and wherein an anti-CarP antibody from a human rheumatoid arthritis (RA) patient binds to the anti-CarP antibody binding sites in their carbamylated states, but not their uncarbamylated states, to form purified polypeptide-anti-CarP antibody complexes. In some embodiments, the anti-CarP antibody is a plurality of anti-CarP antibodies.

In some embodiments, more than 10%, more than 20%, more than 30%, more than 40%, more than 50%, more than 60%, more than 70%, more than 80%, or more than 90% of anti-CarP antibody binding sites are in their carbamylated states.

In some embodiments, the purified polypeptide is a plurality of purified polypeptides. In some embodiments, more than 10%, more than 20%, more than 30%, more than 40%, more than 50%, more than 60%, more than 70%, more than 80%, or more than 90% of anti-CarP antibody binding sites are in their carbamylated state in more than 10%, more than 20%, more than 30%, more than 40%, more than 50%, more than 60%, more than 70%, more than 80%, more than 90%, more than 95% or more than 99% of the purified polypeptides in the plurality of purified polypeptides.

In another aspect this disclosure provides complexes including a purified polypeptide of this disclosure and one or more anti-CarP antibodies. In some embodiments, the complex is in solution. In some embodiments, the complex is immobilized on a surface.

In another aspect this disclosure provides methods for preparing a purified polypeptide including an in vitro carbamylated hA1AT, or fragment thereof, the method including (a) purifying a polypeptide including the hA1AT, or fragment thereof, and (b) in vitro carbamylating the hA1AT, or fragment thereof. In some embodiments, the purified polypeptide is a plurality of purified polypeptides.

In some embodiments, the polypeptide including the hA1AT, or fragment thereof, is purified before the hA1AT, or fragment thereof, is in vitro carbamylated.

In some embodiments, the hA1AT, or fragment thereof, is in vitro carbamylated before the polypeptide including the in vitro carbamylated hA1AT, or fragment thereof, is purified.

In another aspect this disclosure provides methods for detecting anti-CarP antibodies in a subject, including a) contacting a sample from the subject with a purified polypeptide including an in vitro carbamylated hA1AT, or fragment thereof, to form a complex between an anti-CarP antibody of the sample and the purified polypeptide; and b) detecting the presence or absence of the anti-CarP antibody-purified polypeptide complex.

In some embodiments, the presence or absence of the anti-CarP antibody-purified polypeptide complex is detected by an assay such as an enzyme-linked immunosorbent assay (ELISA), a fluorescent immunosorbent assay (FIA), a chemiluminescence immuno assay (CIA), a radioimmunoassay (RIA), an enzyme multiplied immunoassay, a solid phase radioimmunoassay (SPROA), a fluorescence polarization (FP) assay, a fluorescence resonance energy transfer (FRET) assay, a time-resolved fluorescence resonance energy transfer (TR-FRET) assay, a surface plasmon resonance (SPR) assay, or a Dot-Blot assay.

In some embodiments, the subject is suspected of having RA.

In some embodiments, the subject is negative for anti-citrullinated protein antibodies (ACPA⁻).

In some embodiments, the detecting the presence or absence of the anti-CarP antibody-purified polypeptide complex includes establishing a level of the anti-CarP antibody in the sample.

In some embodiments, detecting the presence or absence of the anti-CarP antibody-polypeptide complex includes comparing the level of the anti-CarP antibody in the sample from the subject to a control level of anti-CarP antibody in a sample from a healthy control individual, wherein an increase in the anti-CarP-antibody level in the sample compared to the control level indicates that the subject has RA.

In another aspect, this disclosure provides kits for detecting an anti-CarP antibody, for diagnosing, monitoring or prognosticating RA, or for determining the efficacy of an RA treatment in a subject, the kits including a purified polypeptide including an in vitro carbamylated hA1AT, or fragment thereof, and an ancillary reagent.

In some embodiments, the kit includes a packaging having a label indicating the kit is used for diagnosis, prognosis or monitoring of RA or a RA subtype. In some embodiments, the label is approved by the United States Food and Drug Administration (FDA) or by the European Medicines Agency (EMA). In some embodiments, the kit is labeled for use as an In Vitro Diagnostic (IVD) companion diagnostic device.

In another aspect, this disclosure provides methods of diagnosing RA in a subject suspected of having RA, including a) contacting a sample from the subject with a purified polypeptide including an in vitro carbamylated hA1AT, or fragment thereof, to form a complex between an anti-CarP antibody of the sample and the purified polypeptide, and b) detecting the presence or absence of the anti-CarP antibody-purified polypeptide complex, wherein the presence of the anti-CarP antibody-purified polypeptide complex indicates that the subject has RA.

In another aspect, this disclosure provides methods of determining the prognosis of rheumatoid arthritis (RA) in a human subject, including a) contacting a sample from the subject with a purified polypeptide including an in vitro carbamylated hA1AT, or fragment thereof, to form a complex between an anti-CarP antibody from the sample and the purified polypeptide, and b) detecting the presence or absence of the anti-CarP antibody-purified polypeptide complex, wherein the presence of the anti-CarP antibody-purified polypeptide complex predicts the course of RA progression in the human subject.

In some embodiments, the human subject is an asymptomatic subject suspected to be at risk of developing RA. In some embodiments, the presence of the anti-CarP antibody-purified polypeptide complex indicates that the patient is at a greater risk of developing RA than the absence of the anti-CarP antibody-purified polypeptide complex.

In some embodiments, the human subject is a RA patient having a clinical symptom of RA. In some embodiments, the presence of the anti-CarP antibody-purified polypeptide complex in the sample predicts a more severe clinical course of RA disease progression than the absence of the anti-CarP antibody-purified polypeptide complex.

In some embodiments, the subject is an arthralgia patient. In some embodiments, the presence of the anti-CarP antibody-purified polypeptide complex indicates an about 10-20% greater risk that the arthralgia patient will develop RA within five years from determining the presence of the anti-CarP antibody-purified polypeptide complex than the absence of the anti-CarP antibody-purified polypeptide complex.

In some embodiments, the sample is negative for ACPAs.

In some embodiments, detecting the presence or absence of the anti-CarP antibody-purified polypeptide complex includes determining a level of anti-CarP antibody in the sample.

In some embodiments, a higher level of the anti-CarP antibody in the sample indicates a higher risk that an asymptomatic subject will develop RA than a lower level of the anti-CarP antibody.

In some embodiments, a higher level of the anti-CarP antibody in the sample predicts a more severe course of future disease progression in a RA patient than a lower level of the anti-CarP antibody.

In another aspect, this disclosure provides a method of monitoring the efficacy of an RA treatment in a RA patient, including a) contacting two or more samples obtained from the patient at a first and a subsequent time point throughout the course of the RA treatment with a purified polypeptide including an in vitro carbamylated hA1AT, or fragment thereof, to form a complex between an anti-CarP antibody from the two or more samples and the purified polypeptide; b) determining a level of the anti-CarP antibody for each of the two or more samples, and c) comparing the level of the anti-CarP antibody between the two or more samples, where a decreased level of the anti-CarP antibody in one or more samples obtained at the subsequent time point relative to the level of anti-CarP antibody obtained at the first time point indicates that the RA treatment is efficacious.

In some embodiments, the level of the anti-CarP antibody in the samples obtained at the subsequent time point are decreased by more than 10%, more than 20%, more than 30%, more than 40%, more than 50%, more than 60%, more than 70%, more than 80%, more than 90%, more than 95%, or more than 99%.

BRIEF DESCRIPTION OF THE DRAWINGS

FIG. 2A compares HPLC fractions with respect to their relative protein content (clear circles), their reactivity with an anti-CarP human IgG antibody (solid squares) and their reactivity with normal serum (PMDx, clear diamonds). FIG. 2B compares selected HPLC fractions with respect to their reactivity with serum samples from CarP$^+$/ACPA$^-$ RA patients (BVx0038: clear circle; BVx0077: clear triangle), CarP$^-$/ACPA$^+$ RA patients (BVx0032: clear diamonds; BVx0008: double cross) and normal controls (Neg (PMDx 1193); Neg (PMDx 1196); crosses).

FIG. 3A illustrates the analysis of samples from the 1G4 HPLC-fraction on a SDS-PAGE gel. Protein bands 3 and 4 were excised and subjected to chymotrypsin digests. FIGS. 3B and 3C illustrate the results of the mass-spectrometry (MS) analysis of protein bands 3 and 4. A1AT fragments were identified with probability scores of >95%. FIG. 3B shows a listing of proteins identified in protein bands 3 and 4, regardless of the presence of carbamylated lysine residues in the proteins. FIG. 3C shows a listing of proteins in protein bands 3 and 4 that contained carbamylated lysine residues.

FIG. 4 illustrates that antigen-recognition of anti-CarP antibodies in serum samples from human RA patients is carbamylation-specific.

FIG. 5 illustrates that the anti-Ca-FCS immunoreactivity of anti-CarP antibodies correlated with their activity against Ca-A1AT.

FIG. 6A shows the results of a comparative receiver operating characteristic (ROC) analysis (x-axis: true negative rate; y-axis: true positive rate; Ca-FCS: closed squares; CA-A1AT: open diamonds). FIG. 6B shows a comparison of Ca-FCS and Ca-A1AT assay sensitivities at a fixed specificity of 98.8% (TP: true positive; TN: true negative). FIG. 6C shows a comparison of positive and negative likelihood ratios (LR (+), LR(−)) and odds ratios (OR) for Ca-FCS and CA-A1AT assays, respectively.

DETAILED DESCRIPTION

Figure 1:
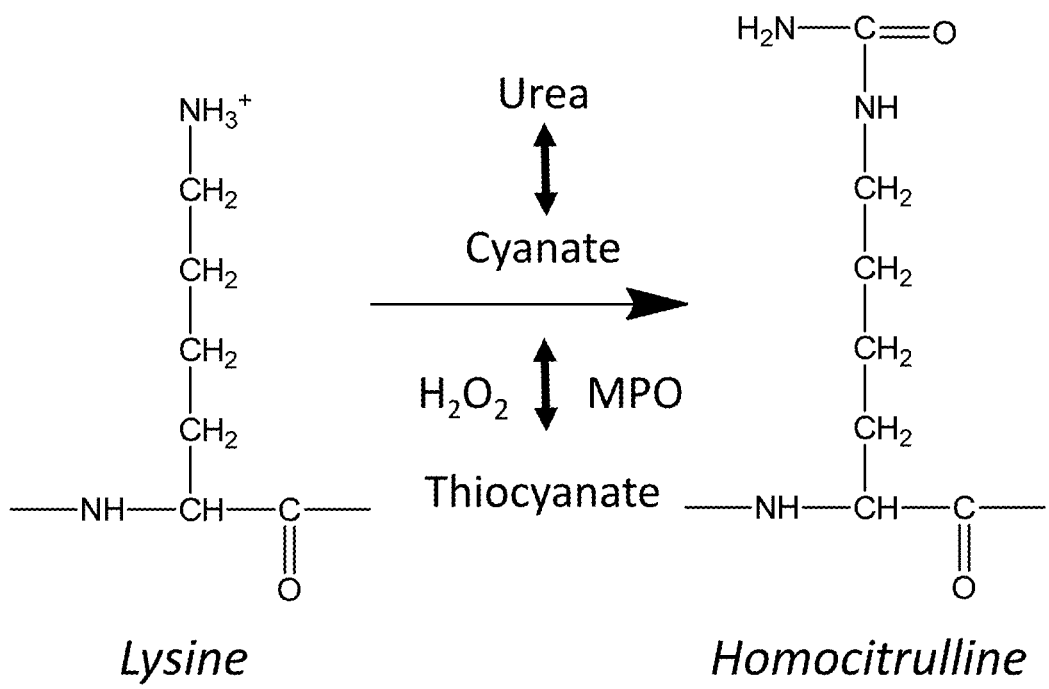
FIG. 1 shows a schematic illustrating carbamylation as a post-translational protein modification.

Autoantibodies directed against carbamylated proteins (anti-CarP antibodies) are diagnostic and prognostic biomarkers in RA. Sensitive and robust anti-CarP antibody detection assays are needed to facilitate the further investigation and development of anti-CarP antibody biomarkers. Ultimately, anti-CarP antibody assays are needed that can meet the stringent regulatory requirements for clinical diagnostic and prognostic assays in order to develop the full clinical utility of anti-CarP antibodies. To develop such high-performance assays, assay components are needed that can be reproducibly produced and analytically characterized and defined.

Current assays for the detection of anti-CarP antibodies in serum samples of human RA patients involve the use of carbamylated fetal calf serum (Car-FCS) as a capture reagent. Fetal calf serum (FCS) and Car-FCS are complex biological reagents that are difficult to manufacture in a reproducible manner and that contain a multitude of protein and non-protein components that can non-specifically interact with anti-CarP antibodies and other immunoglobulins in human serum samples. Non-specific background signals observed in Car-FCS-based anti-CarP antibody assays are relatively high and can be variable, depending on the batch of FCS used.

The present disclosure is based, in part, on the realization that, to improve the sensitivity, accuracy, reproducibility and robustness of anti-CarP antibody assays and to facilitate stringent quality control and high degrees of batch-to-batch reproducibility in the production of assay reagents and clinical test kits, new composition and methods are needed that are based on purified anti-CarP antibody capture reagents.

The present disclosure is further based, in part, on the discovery that carbamylated bovine (α)1-antitrypsin is a prominent antigen in FCS recognized by anti-CarP antibodies found in serum samples of human RA patients. See, e.g., Examples 1 and 2, FIGS. 1-4.

The present disclosure benefits RA patients by providing new tools for the diagnostic and prognostic assessment of their disease. Especially ACPA-negative RA patients will benefit from the compositions and methods of this disclosure. The detection of anti-CarP antibodies in ACPA-negative RA patients was shown to predict the onset of clinically manifested RA and a more severe disease progression. The compositions and methods of this disclosure can facilitate the early detection of RA and thereby enable at-risk RA candidates or early-stage-RA patients to take preventative measures to prevent, delay or ameliorate the further progression of RA.

It must be noted that, as used in this specification and the appended claims, the singular forms "a", "an" and "the" include plural referents unless the content clearly dictates otherwise. Thus, for example, reference to "a purified polypeptide" includes a mixture of two or more purified polypeptides, and the like.

The term "about," particularly in reference to a given quantity, is meant to encompass deviations of plus or minus five percent.

As used herein, the terms "includes," "including," "comprises," "comprising," "contains," "containing," and any variations thereof, are intended to cover a non-exclusive inclusion, such that a process, method, product-by-process, or composition of matter that includes, comprises, or contains an element or list of elements does not include only those elements but can include other elements not expressly listed or inherent to such process, method, product-by-process, or composition of matter.

As used herein, the term "carbamylation" is intended to mean the conversion of an amine into a carbamide (urea). Carbamylation can occur, e.g., as a chemical reaction or an enzymatic reaction. Chemical carbamylation includes, without limitation, reactions of amines with isocyanic acid (HNCO), cyanate ([NCO]$^-$), thiocyanate, or isocyanate groups of organic compounds. In some embodiments, carbamylation includes the reaction of an amine with cyanate. In some embodiments, carbamylation includes the reaction of an amine with potassium-cyanate. Enzymatic carbamylation can be catalyzed, e.g., by a peroxidase or a carbamoyl-transferase. In some embodiments, the carbamylation is catalyzed by a myeloperoxidase (MPO). In some embodiments, carbamylation is catalyzed by a lysine-carbamoyl-transferase.

Carbamylation includes the carbamylation of biomolecules (e.g., polypeptides, peptides, lipids, carbohydrates, or nucleic acids) and of artificial molecules, such as plastics or polymers.

In some embodiments, carbamylation includes the conversion of a lysine residue into a homocitrulline residue, e.g., in a peptide or polypeptide. The lysine residue can be converted into homocitrulline, e.g., by chemically or enzymatically modifying the ε-amino-group of the lysine sidechain to form homocitrulline (also referred to as K(Car)). See, e.g., FIG. 1. In some embodiments, carbamylation includes the replacement of a lysine residue by a homocitrulline residue in a peptide or polypeptide, e.g., by incorporating a homocitrulline residue in the place of a lysine residue during peptide or polypeptide synthesis.

Carbamylation can be performed in vitro or in vivo. For example, in vitro carbamylation can include the chemical or enzymatic modification or the chemical or biochemical synthesis (e.g., peptide synthesis, in vitro translation) of purified biomolecules (e.g., peptides or polypeptides) or the chemical or enzymatic modification of complex biological samples, such as fetal calf serum (FCS), human serum, and the like. In vivo carbamylation can include, e.g., the enzymatic modification of biomolecules in recombinant cells (e.g., HEK, CHO, or Sf9 cells; E. coli cells; yeast cells or others) that contain cDNAs encoding a lysine-carbamoyl-transferase or other enzymes catalyzing carbamylation reactions.

Carbamylated biomolecules, such as peptides or polypeptides, can be carbamylated at a single position, e.g., at a single lysine residue, or at a plurality of positions, e.g., at a plurality of lysine residues. In some embodiments, more than 1%, more than 3%, more than 5%, more than 10%, more than 15%, more than 20%, more than 25%, more than 30%, more than 40%, more than 50%, more than 60%, more than 70%, more than 80%, more than 90%, more than 95%, or more than 99% of all lysine residues in a peptide or polypeptide are carbamylated.

As used herein, the term "plurality" refers to a population of two or more members, such as polypeptide members or other referenced molecules. In some embodiments, the two or more members of a plurality of members are the same members. For example, a plurality of polypeptides can include two or more polypeptide members having the same amino acid sequence and having the same lysine residues carbamylated. In some embodiments, the two or more members of a plurality of members are different members. For example, a plurality of polypeptides can include two or more polypeptide members having different amino acid sequences. In another example, a plurality of polypeptides can include two or more polypeptide members having the same amino acid sequences but having lysine residues carbamylated in different positions or to a different degree. A plurality includes 2, 3, 4, 5, 6, 7, 8, 9, 10, 20, 30, 40, 50, 60, 70, 80, 90 or a 100 or more different members. A plurality can also include 200, 300, 400, 500, 1000, 5000, 10000, 50000, $1 \times 10^5$, $2 \times 10^5$, $3 \times 10^5$, $4 \times 10^5$, $5 \times 10^5$, $6 \times 10^5$, $7 \times 10^5$, $8 \times 10^5$, $9 \times 10^5$, $1 \times 10^6$, $2 \times 10^6$, $3 \times 10^6$, $4 \times 10^6$, $5 \times 10^6$, $6 \times 10^6$, $7 \times 10^6$, $8 \times 10^6$, $9 \times 10^6$ or $1 \times 10^7$ or more different members. A plurality includes all integer numbers in between the above exemplary plurality numbers.

As used herein, the term "at risk" refers to an increased likelihood that a subject will develop a certain disease condition or clinical symptoms of disease in the future. For example, a subject who is "at risk of developing RA" or "at risk of developing clinical symptoms of RA" is more likely in the future to develop RA or clinical symptoms of RA than the median or average subject in a given population. A subject who is "at risk" of developing a disease condition in the future does not already suffer from this condition. A subject who is "at risk" of developing a disease condition can display certain biomarkers, such as elevated levels of anti-CarP antibodies, that indicate an increased likelihood that the subject will develop a certain disease condition (e.g., RA) or clinical symptoms of a certain disease condition (e.g., joint pain, inflammation of synovial joints).

The term "polypeptide," as used herein, includes a short oligopeptide having between 2 and 30 amino acids (e.g., 2, 3, 4, 5, 6, 7, 8, 9, 10, 12, 14, 16, 18, 20, 25 or 30 amino acids) as well as longer amino acid chains, e.g., more than 30 amino acids, more than 50 amino acids, more than 100 amino acids, more than 150 amino acids, more than 200 amino acids, more than 300 amino acids, more than 400 amino acids, more than 500 amino acids, or more than 600 amino acids. The polypeptides of this disclosure include, e.g., recombinant polypeptides, polypeptides purified from tissues or bodily fluids, and any fragments thereof. Polypeptide fragments can be produced, e.g., through protease digests of full length proteins, recombinant expression of polypeptide fragments, or by chemical oligopeptide synthesis. The polypeptides of this disclosure can be posttranslationally or chemically modified (e.g., carbamylation, phosphorylation, biotinylation, attachment of fluorescent dyes, and the like). Polypeptides can include unnatural amino acids that are not encoded by the natural genetic code. For example, polypeptides can include methylated backbone structures, peptoid backbone structures (poly-N-substituted glycines), L-amino acids, R-amino acids, and the like. Polypeptides can have wild-type sequences, naturally occurring variant sequences, mutant sequences (e.g., point mutants, deletion mutants), and the like.

The term "anti-CarP antibody," as used herein, refers to an autoantibody raised by an organism against a carbamylated autoantigen. The anti-CarP antibody specifically recognizes antigens in their carbamylated form, but not in their uncarbamylated form. Antigens recognized by the anti-CarP antibody can include a carbamylated autoantigen or fragment thereof, or carbamylated proteins unrelated to the carbamylated autoantigen. The presence of an anti-CarP antibody is of diagnostic and prognostic value for the assessment of diseases involving autoimmune responses against carbamylated proteins (CarP), such as rheumatoid arthritis (RA). According to this disclosure, in vitro carbamylated alpha 1 antitrypsin (Car-A1AT) is one of the carbamylated protein recognized by an anti-CarP antibody found, e.g., in the serum of human RA patients. The anti-CarP antibody can be of any antibody class or subclass. For example, the anti-CarP antibody can be a IgM, IgA (e.g., $IgA_1$, $IgA_2$), IgD, IgG (e.g., $IgG_1$, $IgG_2$, $IgG_3$, or $IgG_4$), or IgE antibodies. In some embodiments, the anti-CarP antibody of this disclosure interacts via the Fab (fragment antigen-binding) region with an anti-CarP antibody binding site in in vitro carbamylated A1AT. The anti-CarP antibody can be a full-length antibody, e.g., as found in blood, plasma or serum samples. In some embodiments, the anti-CarP antibody of this disclosure can be a processed antibody. For example, in some embodiments, the anti-CarP antibody is deglycosylated or fragmented (e.g., into Fab fragments). The anti-CarP antibody can be a plurality of anti-CarP antibodies, including one or more monoclonal anti-CarP antibodies or one or more polyclonal anti-CarP antibodies. Different anti-CarP antibodies in the plurality of anti-CarP antibodies can bind to the same carbamylated proteins or to different carbamylated proteins. Different anti-CarP antibodies in the plurality of anti-CarP antibodies can recognize either the same or different carbamylated antibody binding sites in carbamylated proteins.

In the methods and compositions provided herein, purified proteins of this disclosure can be immobilized on solid support. In some embodiments, the purified proteins are immobilized via a linke molecule coupling the purified protein to the solid support. When referring to immobilization of molecules (e.g., purified proteins) to a solid support, the terms "immobilized" and "attached" are used interchangeably herein and both terms are intended to encompass direct or indirect, covalent or non-covalent attachment, unless indicated otherwise, either explicitly or by context. In some embodiments, covalent attachment is preferred, but generally all that is required is that the molecules (e.g., purified proteins) remain immobilized or attached to the support under the conditions in which it is intended to use the support, e.g., in applications requiring antibody-binding or detection.

The terms "solid surface," "solid support" and other grammatical equivalents herein refer to any material that is appropriate for or can be modified to be appropriate for the attachment of the purified proteins of this disclosure. As will be appreciated by those in the art, the number of possible substrates is very large. Possible substrates include, but are not limited to, glass and modified or functionalized glass, plastics (including acrylics, polystyrene, polyurethanes, Teflon™, etc.), polysaccharides, nylon or nitrocellulose, ceramics, resins, silica or silica-based materials including silicon and modified silicon, carbon metals, inorganic glasses, optical fiber bundles, and a variety of other polymers. In some embodiments, the solid supports are located in microtiter well plates (e.g., a 96-well, 384-well or 1536-well plate). In some embodiments, the solid supports are located within a flow cell or flow cell apparatus (e.g., a flow cell on a Biacore™ chip or a protein chip).

In some embodiments, the solid support includes a patterned surface suitable for immobilization of purified proteins in an ordered pattern (e.g., a protein chip). A "patterned surface" refers to an arrangement of different regions in or on an exposed layer of a solid support. For example, one or more of the regions can be features where one or more purified proteins are present. The features can be separated by interstitial regions where purified proteins are not present. In some embodiments, the pattern can be an x-y format of features that are in rows and columns. In some embodiments, the pattern can be a repeating arrangement of features and/or interstitial regions. In some embodiments, the pattern can be a random arrangement of features and/or inteststitial regions. Exemplary patterned surfaces that can be used in the methods and compositions set forth herein are described in U.S. Pat. App. Publ. No. 2008/0280785 A1, U.S. Pat. App. Publ. No. 2004/0253640 A1, U.S. Pat. App. Publ. No. 2003/0153013 A1 and International Publication No. WO 2009/039170 A2.

In some embodiments, the solid support includes an array of wells or depressions in a surface. This can be fabricated as is generally known in the art using a variety of techniques, including, but not limited to photolithography, stamping techniques, molding techniques and microetching techniques. As will be appreciated by those skilled in the art, the technique used will depend on the composition and shape of the array substrate.

In some embodiments, the solid support or its surface is non-planar, such as the inner or outer surface of a tube or vessel. In some embodiments, the solid support includes microspheres or beads. By "microspheres" or "beads" or "particles" or grammatical equivalents herein is meant small discrete particles. Suitable bead compositions include, but are not limited to, plastics, ceramics, glass, polystyrene, methylstyrene, acrylic polymers, paramagnetic materials, thoria sol, carbon graphite, titanium oxide, latex or cross linked dextrans such as Sephadose, cellulose, nylon, cross-linked micelles and Teflon™, as well as any other materials outlined herein for solid supports can all be used. "Bangs Beads Technical Product Guide" from Bangs Laboratories (Fishers, Ind.) is a helpful guide. In some embodiments, the microspheres are magnetic microspheres or beads.

The beads need not be spherical; irregular particles can be used. Alternatively or additionally, the beads can be porous. The bead sizes range from nanometers, e.g., 100 nm, to millimeters, e.g., 1 mm, with beads from about 0.2 to about 200 microns being preferred in some embodiments. In some embodiments, bead sizes range from about 0.5 to about 5 microns. In some embodiments beads smaller than about 0.2 microns or larger than about 200 microns can be used.

It is noted that, as used herein, the terms "organism," "individual," "subject," or "patient" are used as synonyms and interchangeably. The subjects of this disclosure include healthy subjects, asymptomatic subjects, and diseased subjects. Diseased subjects can suffer from any disease associated with aberrant anti-carbamylated protein (anti-CarP) antibody levels. The term "aberrant anti-CarP antibody levels", as used herein, refers to anti-CarP antibody levels in a sample that significantly deviate from the median anti-CarP antibody levels found in a population of healthy subjects. In some embodiments, the aberrant anti-CarP antibody levels are higher than the median anti-CarP antibody levels. In some embodiments, the aberrant anti-CarP antibody levels are lower than the median anti-CarP antibody levels.

In some embodiments, the healthy subjects have never suffered from a certain disease. In some embodiments, the healthy subjects were previously diseased. In some embodiments, the healthy subjects are undergoing a routine medical checkup. In some embodiments, the healthy subjects are members of a control group in a clinical trial. In some embodiments, the healthy subjects are at risk of contracting a disease, as determined by the presence of certain risk factors that are well known in the art. Such risk factors include, without limitation, a genetic predisposition, a personal disease history, a familial disease history, a lifestyle factor, an environmental factor, a diagnostic indicator, and the like.

In some embodiments, the subject is asymptomatic. Asymptomatic subjects include healthy subjects who have essentially no risk or only a low risk of developing RA (e.g., there is a less than 10%, less than 5%, less than 3%, or less than 1% probability that the asymptomatic patient will develop RA over the following five year period). Asymptomatic subjects further include healthy subjects who have a high risk of developing RA (e.g., there is a greater than 50%, greater than 70%, greater than 90%, or greater than 95% probability that the asymptomatic patient will develop RA over the following five year period). Asymptomatic subjects further include diseased subjects, who may display mild early diagnostic indicators of RA, but who are otherwise disease or complaint free (e.g., no synovial joint pain, no systemic inflammatory disorder). In some embodiments, the asymptomatic patient is an arthralgia patient.

In some embodiments, the subject has RA. In some embodiments, the subject is suspected of having RA. In some embodiments, the subject has RA with joint pain. In some embodiments, the subject has RA with a systematic inflammatory disorder. In some embodiments, the subject has juvenile idiopathic arthritis (JIA). In some embodiments, the subject has a pre-RA syndrome. In some embodiments, the pre-RA syndrome is arthralgia.

In some embodiments, the subject is at risk of developing RA. In some embodiments, the subject has a genetic predisposition for developing RA or a family history of RA. In some embodiments, the subject is exposed to certain lifestyle factors (e.g., smoking cigarettes) promoting the development of RA or the subject shows clinical disease manifestations of RA. In some embodiments, the subject is a patient who is receiving a clinical workup to diagnose RA or to assess the risk of developing RA.

In some embodiments, the subjects have anti-citrullinated protein antibodies (ACPAs) present, e.g., in their blood or another bodily tissue or fluid, (ACPA-positive subjects). In some embodiments, the subjects have elevated ACPA levels, e.g., in their blood or another bodily tissue or fluid, relative to normal control subjects. In some embodiments, the subjects have no anti-citrullinated protein antibodies (ACPAs) present, e.g., in their blood or another bodily tissue or fluid, (ACPA-negative subjects).

In some embodiments, the subjects have anti-carbamylated protein antibodies (anti-CarP antibodies) present, e.g., in their blood or another tissue or bodily fluid, (anti-CarP antibody-positive subjects) or the subjects have elevated anti-CarP antibody levels, e.g., in their blood or another tissue or bodily fluid, relative to normal control subjects. In some embodiments, the subjects are negative for anti-CarP antibodies.

In some embodiments, the subject is treatment naïve. In some embodiments, the subject is undergoing treatments for RA (e.g., drug treatments). In some embodiments, the subject is in remission. In some embodiments, the remission is drug-induced. In some embodiments, the remission is drug-free.

In some embodiments, the subject is an animal model for RA. In some embodiments, the animal model is a mouse or rabbit model of RA. In some embodiments, the animal model involves inducing anti-CarP antibody responses by vaccinating an animal with carbamylated proteins (CarPs).

In one aspect the present disclosure provides a purified polypeptide including an in vitro carbamylated alpha-1-antitrypsin (A1AT), or fragment thereof. In some embodiments, the in vitro carbamylated A1AT is a mammalian A1AT. In some embodiments, the in vitro carbamylated A1AT is a human A1AT (hA1AT). In some embodiments, the in vitro carbamylated A1AT is a bovine A1AT (bA1AT).

In some embodiments, the present disclosure provides a purified polypeptide including an in vitro carbamylated hA1AT, or fragment thereof.

In some embodiments, the present disclosure provides a purified polypeptide including an in vitro carbamylated bA1AT, or fragment thereof.

In some embodiments, the purified polypeptide is a purified recombinant polypeptide encoded by cDNA.

Methods for expressing and purifying recombinant polypeptides are well known in the art. For example, recombinant polypeptides can be expressed in and purified from bacterial cells (e.g., *E. coli*), yeast cells (e.g., *S. cerevisiae*), in mammalian cells (e.g., CHO) and others. Recombinant polypeptides can be expressed and purified as fusion proteins including tags for protein detection or affinity purification tags (e.g., His-tag, GST-tag, Myc-tag), including cleavable tags (e.g., tags including a TEV-cleavage site).

In some embodiments, the polypeptide is purified from a tissue or bodily fluid obtained from an organism. Tissues or bodily fluids can include any tissue or bodily fluids obtained from the organism. In some embodiments, the tissues or bodily fluids include blood, serum, plasma, urine or milk (e.g., from goats, cows, sheep). A skilled artisan will recognize that methods for the purification of polypeptides from tissues or bodily fluids are well known in the art.

Exemplary methods for expressing and purifying recombinant proteins, for purifying proteins from tissues or bodily fluids, and for chemically synthesizing peptides can be found, e.g., in Scopes R. K., *Protein Purification—Principles and Practice, Springer Advanced Texts in Chemistry*, $3^{rd}$ Edition (1994); Simpson R. J. et al., *Basic Methods in Protein Purification and Analysis: A Laboratory Manual*, Cold Spring Harbor Laboratory Press, $1^{st}$ Edition (2008); Green M. R. and Sambrook J., *Molecular Cloning: A Laboratory Manual*, Cold Spring Harbor Laboratory Press, $4^{st}$ Edition (2012); Jensen K. J. et al., Peptide Synthesis and Applications (Methods in Molecular Biology), Humana Press, $2^{nd}$ Edition (2013).

In some embodiments, the purified polypeptide is a hA1AT purified from blood, serum, plasma, urine, or synovial fluids.

In some embodiments, the purified polypeptide is a bA1AT purified from blood, serum, plasma, urine, or milk.

In some embodiments, the purified polypeptide is a native A1AT. In some embodiments, the purified polypeptide is a denatured or unfolded A1AT. In some embodiments, the purified polypeptide includes unnatural amino acids. In some embodiments, the unnatural amino acids are methylated at the α-amino-group to produce polypeptides with methylated backbones. In some embodiments, the unnatural amino acids are R-amino acids. In some embodiments, the unnatural amino acids include dyes (e.g., fluorescent dyes)

or affinity tags. In some embodiments, the purified polypeptide includes chemical modifications. Chemical modifications include, e.g., chemical modifications with biotin, fluorescent dyes. A skilled artisan will recognize that methods for introducing unnatural amino acids into polypeptides and for chemically modifying polypeptides are well known in the art.

In some embodiments, the purified polypeptide is a plurality of purified polypeptides.

The purified polypeptides of this disclosure include an in vitro carbamylated A1AT. The A1AT can be any mammalian A1AT. In some embodiments, the A1AT is a human, primate (e.g., monkey, chimpanzee, orangutan, or gorilla), cat, dog, rabbit, farm animal (e.g., cow, horse, goat, sheep, or pig), or rodent (e.g., mouse, rat, hamster, or guinea pig) A1AT. In some embodiments, the A1AT is a human A1AT (hA1AT). In some embodiments, the A1AT is a bovine A1AT (bA1AT).

In some embodiments, the A1AT, or fragment thereof, includes the amino acid sequence SEQ ID NO:1 of a mature human A1AT (amino acids 25-418 of NCBI Reference Sequence NP_001002235.1; GI:50363221), or naturally occurring variants thereof:

```
                                        SEQ ID NO: 1
EDPQGDAAQKTDTSHHDQDHPTFNKITPNLAEFAFSLYRQLAHQSNSTNI

FFSPVSIATAFAMLSLGTKADTHDEILEGLNFNLTEIPEAQIHEGFQELL

RTLNQPDSQLQLTTGNGLFLSEGLKLVDKFLEDVKKLYHSEAFTVNFGDT

EEAKKQINDYVEKGTQGKIVDLVKELDRDTVFALVNYIFFKGKWERPFEV

KDTEEEDFHVDQVTTVKVPMMKRLGMFNIQHCKKLSSWVLLMKYLGNAT

AIFFLPDEGKLQHLENELTHDIITKFLENEDRRSASLHLPKLSITGTYDL

KSVLGQLGITKVFSNGADLSGVTEEAPLKLSKAVHKAVLTIDEKGTEAA

GAMFLEAIPMSIPPEVKFNKPFVFLMIEQNTKSPLFMGKVVNPTQK
```

In some embodiments, the A1AT, or fragment thereof, includes the amino acid sequence SEQ ID NO:2 of a mature bovine A1AT (amino acids 25-416 of NCBI Reference Sequence NP_776307.1; GI:27806941), or naturally occurring variants thereof.

```
                                        SEQ ID NO: 2
GVLQGHAVQETDDTSHQEAACHKIAPNLANFAFSIYHHLAHQSNTSNIFF

SPVSIASAFAMLSLGAKGNTHTEILKGLGFNLTELAEAEIHKGFQHLLHT

LNQPNHQLQLTTGNGLFINESAKLVDTFLEDVKNLYHSEAFSINFRDAEE

AKKKINDYVEKGSHGKIVELVKVLDPNTVFALVNYISFKGKWEKPFEMKH

TTERDFHVDEQTTVKVPMMNRLGMFDLHYCDKLASWVLLLDYVGNVT

ACFILPDLGKLQQLEDKLNNELLAKFLEKKYASSANLHLPKLSISETYDL

KSVLGDVGITEVFSDRADLSGITKEQPLKVSKALHKAALTIDEKGTEAVG

STFLEAIPMSLPPDVEFNRPFLCILYDRNTKSPLFVGKVVNPTQA
```

In some embodiments, the purified polypeptide includes a full-length A1AT. In some embodiments, the full-length A1AT contains the N-terminal signal sequence. In some embodiments, the full-length A1AT is a mature A1AT lacking the N-terminal signal sequence. In some embodiments, the purified polypeptide is a full-length A1AT.

In some embodiments, the purified polypeptide includes an A1AT fragment. In some embodiments, the A1AT fragment includes more than 3, more than 5, more than 10, more than 15, more than 20, more than 25, more than 50, more than 75, more than 100, more than 125, more than 150, more than 200, more than 250, more than 300, more than 350, or more than 400 consecutive amino acids of a full-length A1AT polypeptide. In some embodiments, the A1AT fragment includes less than 100%, less than 95%, less than 90%, less than 80%, less than 75%, less than 70%, less than 65%, less than 60%, less than 55%, less than 50%, less than 45%, less than 40%, less than 35%, less than 30%, less than 25%, less than 20%, less than 15%, less than 10%, or less than 5% of consecutive amino acids of full-length A1AT. In some embodiments, the A1AT fragment is an A1AT peptide fragment.

In some embodiments, the A1AT fragment is chemically synthesized. In some embodiments, the A1AT fragment is chemically synthesized using any peptide synthesis method known in the art. In some embodiments, the A1AT fragment is produced as a recombinant polypeptide. In some embodiments, the A1AT fragment is produced by enzymatically digesting full-length A1AT or a fragment thereof. In some embodiments, the enzymatic digest is carried out with a protease or peptidase. In some embodiments, the protease or peptidase is an exoprotease or an exopeptidase. In some embodiments, the protease or peptidase is an endoprotease or endopeptidase. In some embodiments, the protease or peptidase includes a serine protease, threonine protease, cystein protease, aspartate protease, glutamic acid protease, or metalloprotease. In some embodiments, the protease or peptidase includes, trypsin, chymotrypsin, pepsin, papain any cathepsin (e.g., cathepsin B, L, D, K, or G). A skilled artisan will recognize that methods for the chemical synthesis, recombinant production, or enzymatic digestion of full-length A1AT or fragments thereof are well known in the art.

The A1AT fragment can include any partial lysine-containing amino acid sequence of a full-length A1AT polypeptide. The partial amino acid sequence can include, e.g., 5 or more, 6 or more, 7 or more, 8 or more, 9 or more, 10 or more, 12 or more, 14 or more, 16 or more, 18 or more, 20 or more, 24 or more, 28 or more, or 32 or more consecutive amino acids of the full-length A1AT polypeptide. Two or more A1AT peptide fragments can have partially overlapping A1AT amino acid sequences. The overlapping A1AT amino acid sequences can overlap with respect to 1 or more, 2 or more, 3 or more, 4 or more, 5 or more, 6 or more, 7 or more, 8 or more, 9 or more, 10 or more, 12 or more, 14 or more, 16 or more, 18 or more, 20 or more, 24 or more, 28 or more or 32 or more consecutive amino acids of the full-length A1AT polypeptide.

Exemplary A1AT fragments can have the following partial amino acid sequences of human A1AT, SEQ ID NOs: 3-32:

```
SEQ ID NO: 3:
AEDPQGDAAQKTDTSHHDQDH

SEQ ID NO: 4:
HHDQDHPTFNKITPNLAEFAF

SEQ ID NO: 5:
TAFAMLSLGTKADTHDEILEG

SEQ ID NO: 6:
GNGLFLSEGLKLVDKFLEDV

SEQ ID NO: 7:
FLSEGLKLVDKFLEDVKKLYH
```

-continued

SEQ ID NO: 8:
KLVDKFLEDVKKLYHSEAFTV

SEQ ID NO: 9:
TVNFGDTEEAKKQINDYVEKG

SEQ ID NO: 10:
AKKQINDYVEKGTQGKIVDLV

SEQ ID NO: 11:
NDYVEKGTQGKIVDLVKELDR

SEQ ID NO: 12:
GTQGKIVDLVKELDRDTVFAL

SEQ ID NO: 13:
VFALVNYIFFKGKWERPFEVK

SEQ ID NO: 14:
KGKWERPFEVKDTEEEDFHVD

SEQ ID NO: 15:
DFHVDQVTTVKVPMMKRLGMF

SEQ ID NO: 16:
QVTTVKVPMMKRLGMFNIQHC

SEQ ID NO: 17:
RLGMFNIQHCKKLSSWVLLMK

SEQ ID NO: 18:
KKLSSWVLLMKYLGNATAIFF

SEQ ID NO: 19:
TAIFFLPDEGKLQHLENELTH

SEQ ID NO: 20:
ENELTHDIITKFLENEDRRSA

SEQ ID NO: 21:
DRRSASLHLPKLSITGTYDLK

SEQ ID NO: 22:
KLSITGTYDLKSVLGQLGITK

SEQ ID NO: 23:
KSVLGQLGITKVFSNGADLSG

SEQ ID NO: 24:
LSGVTEEAPLKLSKAVHKAVL

SEQ ID NO: 25:
VTEEAPLKLSKAVHKAVLTID

SEQ ID NO: 26:
APLKLSKAVHKAVLTIDEKGT

SEQ ID NO: 27:
VHKAVLTIDEKGTEAAGAMFL

SEQ ID NO: 28:
AIPMSIPPEVKFNKPFVFLMI

SEQ ID NO; 29:
MSIPPEVKFNKPFVFLMIEQN

SEQ ID NO: 30:
FVFLMIEQNTKSPLFMGKVVN

SEQ ID NO: 31:
EQNTKSPLFMGKVVNPTQKAA

SEQ ID NO: 32:
ALVNYIFFKGKWERPFEVKDT

The A1AT fragments of this disclosure include one or more lysine residues. The A1AT fragments can be carbamylated or non-carbamylated at one or more lysine residues. In some embodiments, the A1AT fragments are carbamylated at all lysine residues. Carbamylated A1AT fragments have homocitrulline at the position of one or more lysine residue. In some embodiments, the A1AT fragments have homocitrulline at the position of all lysine residues. In some embodiments, A1AT fragments having amino acid sequences of SEQ ID NOs:3-32 are carbamylated at one or more lysine residues.

In some embodiments, the A1AT is a wild-type polypeptide or naturally occurring variant thereof.

In some embodiments, the A1AT is a mutant polypeptide. Mutant polypeptides include, without limitation, point mutations, deletions, insertions, duplications, and the like.

In some embodiments, the A1AT is a homolog of a wild-type full-length A1AT polypeptide. In some embodiments, the A1AT is a homolog of full-length human A1AT (hA1AT). In some embodiments, the A1AT is a homolog of full-length bovine A1AT (bA1AT). In some embodiments, the A1AT homolog has greater than 60%, greater than 65%, greater than 70%, greater than 75%, greater than 80%, greater than 85%, greater than 90%, greater than 95%, greater than 96%, greater than 97%, greater than 98%, or greater than 99% sequence identity to a wild-type A1AT.

In some embodiments, the A1AT includes an amino acid sequence homologous to SEQ ID NO:1. In some embodiments, the amino acid sequence homologous to SEQ ID NO:1 has greater than 60%, greater than 65%, greater than 70%, greater than 75%, greater than 80%, greater than 85%, greater than 90%, greater than 95%, greater than 96%, greater than 97%, greater than 98%, or greater than 99% sequence identity to SEQ ID NO:1.

In some embodiments, the A1AT includes an amino acid sequence homologous to SEQ. ID. NO. 2. In some embodiments, the amino acid sequence homologous to SEQ ID NO:2 has greater than 60%, greater than 65%, greater than 70%, greater than 75%, greater than 80%, greater than 85%, greater than 90%, greater than 95%, greater than 96%, greater than 97%, greater than 98%, or greater than 99% sequence identity to SEQ ID NO:2.

The A1ATs in the purified proteins of this disclosure are in vitro carbamylated. See, e.g., FIG. 1.

In some embodiments, in vitro carbamylation includes a chemical reaction. In some embodiments, the chemical reaction includes a reaction of amines with isocyanic acid (HNCO), cyanate ($[NCO]^-$), an organic compound containing an isocyanate group, or a reaction of amines with thiocyanate. In some embodiments, the chemical reaction includes a reaction of an amine with cyanate. In some embodiments, the chemical reaction includes a reaction of an amine with potassium-cyanate.

In some embodiments, in vitro carbamylation is catalyzed by an enzyme. In some embodiments, the enzyme catalyzes the reaction:

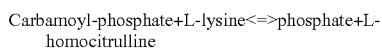
Carbamoyl-phosphate+L-lysine<=>phosphate+L-homocitrulline

In some embodiments, the enzyme is a transferase. In some embodiments, the enzyme is a lysine-carbamoyltransferase. In some embodiments, the enzyme is a peroxidase. In some embodiments, the peroxidase is a myeloperoxidase (MPO).

In some embodiments, in vitro carbamylation includes the incorporation of a homocitrulline residue into A1AT. In some embodiments, the homocitrulline residue replaces one or more lysine residues in A1AT. In some embodiments, all lysine residues in A1AT are replaced by homocitrulline residues. In some embodiments, the homocitrulline residue replaces one or more amino acid residues other than lysine residues in A1AT. In some embodiments homocitrulline residues replace a combination of lysine and non-lysine residues in A1AT. In some embodiments, the homocitrulline residue is incorporated into A1AT in vitro. In some embodiments, the homocitrulline residue is incorporated into A1AT by peptide synthesis. In some embodiments, the homocitrulline residue is a plurality of homocitrulline residues.

Any lysine residue in A1AT, or fragment thereof, can be in vitro carbamylated (replaced by homocitrulline) alone or in combination with any other lysine residue in A1AT or in combination with any other combination of lysine residues in A1AT. Any number of lysine residues in A1AT can be in vitro carbamylated. Any combination of lysine residues in A1AT can be carbamylated. In some embodiments, all lysine residues of A1AT are carbamylated.

The following examples illustrate that any individual lysine residue in an exemplary A1AT, or fragment thereof, can be in vitro carbamylated alone or in combination with any number of lysine residues in A1AT, or fragment thereof. In some embodiments, the in vitro carbamylated A1AT, or fragment thereof, includes an amino acid sequence of any one of SEQ ID NOs: 33-203, where carbamylated lysine residues (homocitrulline residues) are indicated as K(Car):

SEQ ID NO: 33:
AEDPQGDAAQK(Car)TDTSHHDQDH

SEQ ID NO: 34:
HHDQDHPTFNK(Car)ITPNLAEFAF

SEQ ID NO: 35:
TAFAIVILSLGTK(Car)ADTHDEILEG

SEQ ID NO: 36:
GNGLFLSEGLK(Car)LVDKFLEDV

SEQ ID NO: 37:
GNGLFLSEGLKLVDK(Car)FLEDV

SEQ ID NO: 38:
GNGLFLSEGLK(Car)LVDK(Car)FLEDV

SEQ ID NO: 39:
FLSEGLK(Car)LVDKFLEDVKKLYH

SEQ ID NO: 40:
FLSEGLKLVDK(Car)FLEDVKKLYH

SEQ ID NO: 41:
FLSEGLKLVDKFLEDVK(Car)KLYH

SEQ ID NO: 42:
FLSEGLKLVDKFLEDVKK(Car)LYH

SEQ ID NO: 43:
FLSEGLK(Car)LVDK(Car)FLEDVKKLYH

SEQ ID NO: 44:
FLSEGLK(Car)LVDKFLEDVK(Car)KLYH

SEQ ID NO: 45:
FLSEGLK(Car)LVDKFLEDVKK(Car)LYH

SEQ ID NO; 46:
FLSEGLKLVDK(Car)FLEDVK(Car)KLYH

SEQ ID NO: 47:
FLSEGLKLVDK(Car)FLEDVKK(Car)LYH

SEQ ID NO: 48:
FLSEGLKLVDKFLEDVK(Car)K(Car)LYH

SEQ ID NO: 49:
FLSEGLK(Car)LVDK(Car)FLEDVK(Car)KLYH

SEQ ID NO: 50:
FLSEGLK(Car)LVDK(Car)FLEDVKK(Car)LYH

SEQ ID NO: 51:
FLSEGLK(Car)LVDKFLEDVK(Car)K(Car)LYH

SEQ ID NO: 52:
FLSEGLKLVDK(Car)FLEDVK(Car)K(Car)LYH

SEQ ID NO: 53:
FLSEGLK(Car)LVDK(Car)FLEDVK(Car)K(Car)LYH

SEQ ID NO: 54:
K(Car)LVDKFLEDVKKLYHSEAFTV

SEQ ID NO: 55:
KLVDK(Car)FLEDVKKLYHSEAFTV

SEQ ID NO: 56:
KLVDKFLEDVK(Car)KLYHSEAFTV

SEQ ID NO: 57:
KLVDKFLEDVKK(Car)LYHSEAFTV

SEQ ID NO: 58:
K(Car)LVDK(Car)FLEDVKKLYHSEAFTV

SEQ ID NO: 59:
K(Car)LVDKFLEDVK(Car)KLYHSEAFTV

SEQ ID NO: 60:
K(Car)LVDKFLEDVKK(Car)LYHSEAFTV

SEQ ID NO: 61:
KLVDK(Car)FLEDVK(Car)KLYHSEAFTV

SEQ ID NO: 62:
KLVDK(Car)FLEDVKK(Car)LYHSEAFTV

SEQ ID NO: 63:
KLVDKFLEDVK(Car)K(Car)LYHSEAFTV

SEQ ID NO: 64:
K(Car)LVDK(Car)FLEDVK(Car)KLYHSEAFTV

SEQ ID NO: 65:
K(Car)LVDK(Car)FLEDVKK(Car)LYHSEAFTV

SEQ ID NO: 66:
K(Car)LVDKFLEDVK(Car)K(Car)LYHSEAFTV

SEQ ID NO: 67:
KLVDK(Car)FLEDVK(Car)K(Car)LYHSEAFTV

SEQ ID NO: 68:
K(Car)LVDK(Car)FLEDVK(Car)K(Car)LYHSEAFTV

SEQ ID NO: 69:
TVNFGDTEEAK(Car)KQINDYVEKG

SEQ ID NO: 70:
TVNFGDTEEAKK(Car)QINDYVEKG

SEQ ID No: 71:
TVNFGDTEEAKKQINDYVEK(Car)G

SEQ ID NO: 72:
TVNFGDTEEAK(Car)K(Car)QINDYVEKG

SEQ ID NO: 73:
TVNFGDTEEAK(Car)KQINDYVEK(Car)G

SEQ ID NO: 74:
TVNFGDTEEAKK(Car)QINDYVEK(Car)G

SEQ ID NO: 75:
TVNFGDTEEAK(Car)K(Car)QINDYVEK(Car)G

SEQ ID NO: 76:
AK(Car)KQINDYVEKGTQGKIVDLV

SEQ ID NO: 77:
AKK(Car)QINDYVEKGTQGKIVDLV

-continued

SEQ ID NO: 78:
AKKQINDYVEK(Car)GTQGKIVDLV

SEQ ID NO: 79:
AKKQINDYVEKGTQGK(Car)IVDLV

SEQ ID NO: 80:
AK(Car)K(Car)QINDYVEKGTQGKIVDLV

SEQ ID NO: 81:
AK(Car)KQINDYVEK(Car)GTQGKIVDLV

SEQ ID NO: 82:
AK(Car)KQINDYVEKGTQGK(Car)IVDLV

SEQ ID NO: 83:
AKK(Car)QINDYVEKGTQGKIVDLV

SEQ ID NO: 84:
AKKQINDYVEK(Car)GTQGKIVDLV

SEQ ID NO: 85:
AKK(Car)QINDYVEKGTQGK(Car)IVDLV

SEQ ID NO: 86:
AKKQINDYVEK(Car)GTQGK(Car)IVDLV

SEQ ID NO: 87:
AK(Car)K(Car)QINDYVEK(Car)GTQGKIVDLV

SEQ ID NO: 88:
AK(Car)K(Car)QINDYVEKGTQGK(Car)IVDLV

SEQ ID NO: 89:
AK(Car)KQINDYVEK(Car)GTQGK(Car)IVDLV

SEQ ID NO: 90:
AKK(Car)QINDYVEK(Car)GTQGK(Car)IVDLV

SEQ ID NO: 91:
AK(Car)K(Car)QINDYVEK(Car)GTQGK(Car)IVDLV

SEQ ID NO: 92:
NDYVEK(Car)GTQGKIVDLVKELDR

SEQ ID NO: 93:
NDYVEKGTQGK(Car)IVDLVKELDR

SEQ ID NO: 94:
NDYVEKGTQGKIVDLVK(Car)ELDR

SEQ ID NO: 95:
NDYVEK(Car)GTQGK(Car)IVDLVKELDR

SEQ ID NO: 96:
NDYVEK(Car)GTQGKIVDLVK(Car)ELDR

SEQ ID NO: 97:
NDYVEKGTQGK(Car)IVDLVK(Car)ELDR

SEQ ID NO: 98:
NDYVEK(Car)GTQGK(Car)IVDLVK(Car)ELDR

SEQ ID NO: 99:
GTQGK(Car)IVDLVKELDRDTVFAL

SEQ ID NO: 100:
GTQGKIVDLVK(Car)ELDRDTVFAL

SEQ ID NO: 101:
GTQGK(Car)IVDLVK(Car)ELDRDTVFAL

SEQ ID NO: 102:
VFALVNYIFFK(Car)GKWERPFEVK

SEQ ID NO: 103:
VFALVNYIFFKGK(Car)WERPFEVK

SEQ ID NO: 104:
VFALVNYIFFKGKWERPFEVK(Car)

SEQ ID NO: 105:
VFALVNYIFFK(Car)GK(Car)WERPFEVK

SEQ ID NO: 106:
VFALVNYIFFK(Car)GKWERPFEVK(Car)

SEQ ID NO: 107:
VFALVNYIFFKGK(Car)WERPFEVK(Car)

SEQ ID NO: 108:
VFALVNYIFFK(Car)GK(Car)WERPFEVK(Car)

SEQ ID NO: 109:
K(Car)GKWERPFEVKDTEEEDFHVD

SEQ ID NO: 110:
KGK(Car)WERPFEVKDTEEEDFHVD

SEQ ID NO: 111:
KGKWERPFEVK(Car)DTEEEDFHVD

SEQ ID NO: 112:
K(Car)GK(Car)WERPFEVKDTEEEDFHVD

SEQ ID NO: 113:
K(Car)GKWERPFEVK(Car)DTEEEDFHVD

SEQ ID NO: 114:
K(Car)GK(Car)WERPFEVK(Car)DTEEEDFHVD

SEQ ID NO: 115:
DFHVDQVTTVK(Car)VPMMKRLGMF

SEQ ID NO: 116:
DFHVDQVTTVKVPMMK(Car)RLGMF

SEQ ID NO: 117:
DFHVDQVTTVK(Car)VPMMK(Car)RLGMF

SEQ ID NO: 118:
QVTTVK(Car)VPMMKRLGMFNIQHC

SEQ ID NO: 119:
QVTTVKVPMMK(Car)RLGMFNIQHC

SEQ ID NO: 120:
QVTTVK(Car)VPMMK(Car)RLGMFNIQHC

SEQ ID NO: 121:
RLGMFNIQHCK(Car)KLSSWVLLMK

SEQ ID NO: 122:
RLGMFNIQHCKK(Car)LSSWVLLMK

SEQ ID NO: 123:
RLGMFNIQHCKKLSSWVLLMK(Car)

SEQ ID NO: 124:
RLGMFNIQHCK(Car)K(Car)LSSWVLLMK

SEQ ID NO: 125:
RLGMFNIQHCK(Car)KLSSWVLLMK(Car)

SEQ ID NO: 126:
RLGMFNIQHCKK(Car)LSSWVLLMK(Car)

SEQ ID NO: 127:
RLGMFNIQHCK(Car)K(Car)LSSWVLLMK(Car)

SEQ ID NO: 128:
K(Car)KLSSWVLLMKYLGNATAIFF

SEQ ID NO: 129:
KK(Car)LSSWVLLMKYLGNATAIFF

SEQ ID NO: 130:
KKLSSWVLLMK(Car)YLGNATAIFF

-continued

SEQ ID NO: 131:
K(Car)K(Car)LS SWVLLMKYLGNATAIFF

SEQ ID NO: 132:
K(Car)KLSSWVLLMK(Car)YLGNATAIFF

SEQ ID NO: 133:
KK(Car)LSSWVLLMK(Car)YLGNATAIFF

SEQ ID NO: 134:
K(Car)K(Car)LSSWVLLMK(Car)YLGNATAIFF

SEQ ID NO: 135:
TAIFFLPDEGK(Car)LQHLENELTH

SEQ ID NO: 136:
ENELTHDIITK(Car)FLENEDRRSA

SEQ ID NO: 137:
DRRSASLHLPK(Car)LSITGTYDLK

SEQ ID NO: 138:
DRRSASLHLPKLSITGTYDLK(Car)

SEQ ID NO: 139:
DRRSASLHLPK(Car)LSITGTYDLK(Car)

SEQ ID NO: 140:
K(Car)LSITGTYDLKSVLGQLGITK

SEQ ID NO: 141:
KLSITGTYDLK(Car)SVLGQLGITK

SEQ ID NO: 142:
KLSITGTYDLKSVLGQLGITK(Car)

SEQ ID NO: 143:
K(Car)LSITGTYDLK(Car)SVLGQLGITK

SEQ ID NO: 144:
K(Car)LSITGTYDLKSVLGQLGITK(Car)

SEQ ID NO: 145:
KLSITGTYDLK(Car)SVLGQLGITK(Car)

SEQ ID NO: 146:
K(Car)LSITGTYDLK(Car)SVLGQLGITK(Car)

SEQ ID NO: 147:
K(Car)SVLGQLGITKVFSNGADLSG

SEQ ID NO: 148:
KSVLGQLGITK(Car)VFSNGADLSG

SEQ ID NO: 149:
K(Car)SVLGQLGITK(Car)VFSNGADLSG

SEQ ID NO: 150:
LSGVTEEAPLK(Car)L SKAVHKAVL

SEQ ID NO: 151:
LSGVTEEAPLKLSK(Car)AVHKAVL

SEQ ID NO: 152:
LSGVTEEAPLKLSAVHK(Car)AVL

SEQ ID NO: 153:
LSGVTEEAPLK(Car)LSK(Car)AVHKAVL

SEQ ID NO: 154:
LSGVTEEAPLK(Car)LSAVHK(Car)AVL

SEQ ID NO: 155:
LSGVTEEAPLKLSK(Car)AVHK(Car)AVL

SEQ ID NO: 156:
LSGVTEEAPLK(Car)LSK(Car)AVHK(Car)AVL

SEQ ID NO: 157:
VTEEAPLK(Car)LSKAVHKAVLTID

SEQ ID NO: 158:
VTEEAPLKLSK(Car)AVHKAVLTID

SEQ ID NO: 159:
VTEEAPLKLSKAVHK(Car)AVLTID

SEQ ID NO: 160:
VTEEAPLK(Car)LSK(Car)AVHKAVLTID

SEQ ID NO: 161:
VTEEAPLK(Car)LSKAVHK(Car)AVLTID

SEQ ID NO: 162:
VTEEAPLKLSK(Car)AVHK(Car)AVLTID

SEQ ID NO: 163:
VTEEAPLK(Car)LSK(Car)AVHK(Car)AVLTID

SEQ ID NO: 164:
APLK(Car)LSKAVHKAVLTIDEKGT

SEQ ID NO: 165:
APLKLSK(Car)AVHKAVLTIDEKGT

SEQ ID NO: 166:
APLKLSAVHK(Car)AVLTIDEKGT

SEQ ID NO: 167:
APLKLSAVHKAVLTIDEK(Car)GT

SEQ ID NO: 168:
APLK(Car)LSK(Car)AVHKAVLTIDEKGT

SEQ ID NO: 169:
APLK(Car)LSAVHK(Car)AVLTIDEKGT

SEQ ID NO: 170:
APLK(Car)LSK(Car)AVHKAVLTIDEKGT

SEQ ID NO: 171:
APLKLSK(Car)AVHKAVLTIDEK(Car)GT

SEQ ID NO: 172:
APLKLSAVHK(Car)AVLTIDEK(Car)GT

SEQ ID NO: 173:
APLK(Car)LSK(Car)AVHK(Car)AVLTIDEKGT

SEQ ID NO: 174:
APLK(Car)LSK(Car)AVHKAVLTIDEK(Car)GT

SEQ ID NO: 175:
APLK(Car)LSAVHK(Car)AVLTIDEK(Car)GT

SEQ ID NO: 176:
APLKLSK(Car)AVHK(Car)AVLTIDEK(Car)GT

SEQ ID NO: 177:
APLK(Car)LSK(Car)AVHK(Car)AVLTIDEK(Car)GT

SEQ ID NO: 178:
VHK(Car)AVLTIDEKGTEAAGAMFL

SEQ ID NO: 179:
VHKAVLTIDEK(Car)GTEAAGAMFL

SEQ ID NO: 180:
VHK(Car)AVLTIDEK(Car)GTEAAGAMFL

SEQ ID NO: 181:
AIPMSIPPEVK(Car)FNKPFVFLMI

SEQ ID NO: 182:
AIPMSIPPEVKFNK(Car)PFVFLMI

SEQ ID NO: 183:
AIPMSIPPEVK(Car)FNK(Car)PFVFLMI

SEQ ID NO: 184:
MSIPPEVK(Car)FNKPFVFLMIEQN

-continued

SEQ ID NO: 185:
MSIPPEVKFNK(Car)PFVFLMIEQN

SEQ ID NO: 186:
MSIPPEVK(Car)FNK(Car)PFVFLMIEQN

SEQ ID NO: 187:
FVFLMIEQNTK(Car)SPLFMGKVVN

SEQ ID NO: 188:
FVFLMIEQNTKSPLFMGK(Car)VVN

SEQ ID NO: 189:
FVFLMIEQNTK(Car)SPLFMGK(Ca r)VVN

SEQ ID NO: 190:
EQNTK(Car)SPLFMGKVVNPTQKAA

SEQ ID NO: 191:
EQNTKSPLFMGK(Car)VVNPTQKAA

SEQ ID NO: 192:
EQNTKSPLFMGKVVNPTQK(Car)AA

SEQ ID NO: 193:
EQNTK(Car)SPLFMGK(Car)VVNPTQKAA

SEQ ID NO: 194:
EQNTK(Car)SPLFMGKVVNPTQK(Car)AA

SEQ ID NO: 195:
EQNTKSPLFMGK(Car)VVNPTQK(Car)AA

SEQ ID NO: 196:
EQNTK(Car)SPLFMGK(Car)VVNPTQK(Car)AA

SEQ ID NO: 197:
ALVNYIFFK(Car)GKWERPFEVKDT

SEQ ID NO: 198:
ALVNYIFFKGK(Car)WERPFEVKDT

SEQ ID NO: 199:
ALVNYIFFKGKWERPFEVK(Car)DT

SEQ ID NO: 200:
ALVNYIFFK(Car)GK(Car)WERPFEVKDT

SEQ ID NO: 201:
ALVNYIFFK(Car)GKWERPFEVK(Car)DT

SEQ ID NO: 202:
ALVNYIFFKGK(Car)WERPFEVK(Car)DT

SEQ ID NO: 203:
ALVNYIFFK(Car)GK(Car)WERPFEVK(Car)DT

In some embodiments, more than 10%, more than 20%, more than 30%, more than 40%, more than 50%, more than 60%, more than 70%, more than 80%, more than 90%, or more than 95% of lysine residues in the A1AT, or fragment thereof, are carbamylated. In some embodiments, 100% of lysine residues in the A1AT, or fragment thereof, are carbamylated.

In some embodiments, more than 10%, more than 20%, more than 30%, more than 40%, more than 50%, more than 60%, more than 70%, more than 80%, more than 90%, or more than 95% of lysine residues in the hA1AT, or fragment thereof, are carbamylated. In some embodiments, 100% of lysine residues in the hA1AT, or fragment thereof, are carbamylated.

In some embodiments, more than 10%, more than 20%, more than 30%, more than 40%, more than 50%, more than 60%, more than 70%, more than 80%, more than 90%, or more than 95% of lysine residues in the bA1AT, or fragment thereof, are carbamylated. In some embodiments, 100% of lysine residues in the bA1AT, or fragment thereof, are carbamylated.

In some embodiments, the purified polypeptide is a plurality of purified polypeptides. In some embodiments, more than 10%, more than 20%, more than 30%, more than 40%, more than 50%, more than 60%, more than 70%, more than 80%, more than 90%, more than 95%, or more than 99% of lysine residues are carbamylated in the in vitro carbamylated hA1AT, or fragment thereof, of more than 10%, more than 20%, more than 30%, more than 40%, more than 50%, more than 60%, more than 70%, more than 80%, more than 90%, more than 95%, or more than 99% of purified polypeptides in the plurality of purified polypeptides.

In some embodiments, the plurality of purified polypeptides includes purified polypeptides, whereby one or more purified polypeptide includes an A1AT amino acid sequence of any one of SEQ ID NOs: 3-203.

In some embodiments, the hA1AT, or fragment thereof, includes a fragment of 8 or more contiguous amino acids with greater than 80%, greater than 85%, greater than 90%, greater than 95%, greater than 96%, greater than 97%, greater than 98%, or greater than 99% sequence identity to SEQ ID NO.1. In some embodiments, the hA1AT, or fragment thereof, includes a fragment of 16 or more contiguous amino acids with greater than 60%, greater than 65%, greater than 70%, greater than 75%, greater than 80%, greater than 85%, greater than 90%, greater than 95%, greater than 96%, greater than 97%, greater than 98%, or greater than 99% sequence identity to SEQ ID NO.1.

In some embodiments, the hA1AT, or fragment thereof, includes a fragment of 8 or more contiguous amino acids with greater than 60%, greater than 65%, greater than 70%, greater than 75%, greater than 80%, greater than 85%, greater than 90%, greater than 95%, greater than 96%, greater than 97%, greater than 98%, or greater than 99% sequence identity to SEQ ID NO.2. In some embodiments, the hA1AT, or fragment thereof, includes a fragment of 16 or more contiguous amino acids with greater than 60%, greater than 65%, greater than 70%, greater than 75%, greater than 80%, greater than 85%, greater than 90%, greater than 95%, greater than 96%, greater than 97%, greater than 98%, or greater than 99% sequence identity to SEQ ID NO.2.

RA patients can be very heterogeneous with respect to the biomarker profiles detectable in their blood. For example, some RA patients can be positive for anti-CarP antibodies and positive for ACPAs; some RA patients can be positive for anti-CarP antibodies and negative for ACPAs; some RA patients can be negative for anti-CarP antibodies and positive for ACPAs and some RA patients can be negative for both anti-CarP antibodies and ACPAs. The determination of comprehensive biomarker profiles for RA patients is expected to facilitate the identification of RA patient subpopulations (e.g., ACPA⁻/anti-CarP antibody⁺ RA patients), aid in the diagnosis of RA disease subtypes, and aid in the prognostication of disease progression and treatment outcomes for specific RA disease subtypes. Although some crossreactivity exists, anti-CarP antibodies, in general, preferentially recognize carbamylated proteins over citrullinated protein and ACPAs, in general, preferentially recognize citrullinated proteins over carbamylated proteins. The selective recognition of at least some carbamylated proteins by anti-CarP antibodies can therefore be used to distinguish anti-CarP and ACPA biomarkers in RA patient samples and to distinguish RA patients based on their anti-CarP antibody and ACPA profiles.

The A1ATs, or fragments thereof, of this disclosure each include one or more anti-CarP antibody binding sites, each of which anti-CarP antibody binding sites can independently be in a carbamylated state or an uncarbamylated state. Anti-CarP antibodies from human rheumatoid arthritis patients bind to the anti-CarP antibody binding sites in A1ATs, or fragments thereof, in their carbamylated states, but not their uncarbamylated states, to form Car-A1AT-anti-CarP antibody complexes.

In some embodiments, the anti-CarP antibody binding sites include one or more lysine residues. In some embodiments, one or more lysine residues in an anti-CarP antibody binding sites are carbamylated (to form homocitrulline residues) when the anti-CarP antibody binding site is in a carbamylated state. In some embodiments, one or more lysine residues in the anti-CarP antibody binding sites are uncarbamylated when the anti-CarP antibody binding site is in a carbamylated state. In some embodiments, all lysine residues in a anti-CarP antibody binding site are carbamylated when the anti-CarP antibody binding site in a carbamylated state.

In some embodiments, the hA1AT, or fragment thereof, includes one or more anti-CarP antibody binding sites, each of which can independently be in a carbamylated state or uncarbamylated state and where an anti-CarP antibodies from a human RA patient binds to the anti-CarP antibody binding sites in its carbamylated state, but not its uncarbamylated state, to form a Car-hA1AT-anti-CarP antibody complex.

In some embodiments, the bA1AT, or fragment thereof, includes one or more anti-CarP antibody binding sites, each of which can independently be in a carbamylated state or uncarbamylated state and where an anti-CarP antibody from a human RA patient binds to the anti-CarP antibody binding sites in their carbamylated states, but not their uncarbamylated states, to form Car-bA1AT-anti-CarP antibody complexes.

In some embodiments, more than 10%, more than 20%, more than 30%, more than 40%, more than 50%, more than 60%, more than 70%, more than 80%, or more than 90% of anti-CarP antibody binding sites are in their carbamylated states.

In some embodiments, the purified polypeptide including the in vitro carbamylated A1AT, or fragment thereof, is a plurality of purified polypeptides. In some embodiments, more than 10%, more than 20%, more than 30%, more than 40%, more than 50%, more than 60%, more than 70%, more than 80%, or more than 90% of anti-CarP antibody binding sites are in their carbamylated state in more than 10%, more than 20%, more than 30%, more than 40%, more than 50%, more than 60%, more than 70%, more than 80%, more than 90%, more than 95% or more than 99% of the purified polypeptides in the plurality of purified polypeptides.

In some embodiments, the anti-CarP antibody binding sites are recognized by an anti-CarP antibodies from samples of rheumatoid arthritis patients, but are not recognized by ACPAs from samples of rheumatoid arthritis patients. The ACPAs can be directed against any citrullinated polypeptide, including citrullinated proteins such as Mutated Citrullinated Vimentin (MCV; anti-Cit-MCV antibodies), and citrullinated peptides, such as cyclic citrullinated peptide (CCP), or fragments thereof.

In some embodiments, one or more anti-CarP antibody binding sites in a purified protein of this disclosure are recognized by an anti-CarP antibody and an ACPA from samples of human rheumatoid arthritis patients. In some embodiments, the anti-CarP antibody binding sites are recognized by more than 5%, more than 10%, more than 15%, more than 20%, more than 25%, more than 30%, more than 40%, more than 50%, more than 60%, more than 70%, more than 80%, more than 90%, more than 95%, or more than 99% of anti-CarP antibodies in a sample from a rheumatoid arthritis patient and by less than 100%, less than 95%, less than 90%, less than 80%, less than 70%, less than 60%, less than 50%, less than 40%, less than 30%, less than 20%, less than 10%, less than 5%, less than 3%, or less than 1% of APCAs in the sample of the rheumatoid arthritis patient. In some embodiments, the anti-CarP antibody binding sites are bound with greater affinity by an anti-CarP antibody from a sample of a rheumatoid arthritis patients than by an APCA from a sample of a rheumatoid arthritis patients. In some embodiments, the anti-CarP antibody binding sites are bound with more than 2-fold, more than 5-fold, more than 10-fold, more than 25-fold, more than 50-fold, more than 100-fold, more than 300-fold, more than 1,000-fold, more than 3,000-fold, more than 10,000-fold, more than 30,000-fold, or more than 100,000-fold greater affinity by an anti-CarP antibody from a samples of an RA patient than by an APCA from a sample of the RA patient.

In some embodiments, the anti-CarP antibody is a plurality of anti-CarP antibodies.

In another aspect, this disclosure provides a complex including a purified polypeptide of this disclosure and one or more anti-CarP antibodies. In some embodiments, the complex is in solution. In some embodiments, the complex is immobilized on a surface. In some embodiments, the complex is a purified complex. In some embodiments, the complex is contained in a biological fluid, e.g., blood, serum, plasma, urine, milk, and the like. In some embodiments, the complexed anti-CarP antibodies are purified antibodies. In some embodiments, the complexed anti-CarP antibodies are contained in a biological fluid, e.g., blood, serum, plasma, urine, milk, and the like.

In another aspect, this disclosure provides methods of preparing a purified polypeptide including an in vitro carbamylated A1AT (e.g., hA1AT or bA1AT), or fragment thereof. The methods include (a) purifying a polypeptide including an A1AT, or fragment thereof, and (b) in vitro carbamylating the A1AT, or fragment thereof.

In some embodiments, the polypeptide including the A1AT, or fragment thereof, is purified in an uncarbamylated form before the A1AT, or fragment thereof, is in vitro carbamylated. In some embodiments, the polypeptide is purified in an uncarbamylated form from a cellular lysate, such as a lysate obtained by lysing recombinant cells or liver cells that express A1AT, or fragment thereof, from a cell culture supernatant (e.g., a supernatant of a liver cell culture). In some embodiments the polypeptide is purified in an uncarbamylated form from blood, plasma, serum or other biological fluid, or from a tissue extract, such as a liver extract. In some embodiments, the A1AT, or fragment thereof, is in vitro carbamylated in the purified polypeptide in a chemical or enzymatic reaction, e.g., in a reaction buffer.

In some embodiments, the A1AT, or fragment thereof, is in vitro carbamylated to produce a polypeptide including an in vitro carbamylated A1AT, or fragment thereof, before the polypeptide is purified. In some embodiments, the A1AT, or fragment thereof, is in vitro carbamylated, e.g., using a chemical or enzymatic reaction, while in a cellular lysate, such as a lysate obtained by lysing recombinant cells or liver cells that express A1AT, or fragment thereof. In some embodiments the A1AT, or fragment thereof, is in vitro carbamylated in blood, plasma, serum or other biological fluid, or from a tissue extract, such as a liver extract. In some embodiment, the A1AT, or fragment thereof, is in vitro carbamylated in fetal calf serum (FCS), bovine serum, or human serum. In some embodiments, the polypeptide including the in vitro carbamylated A1AT, or fragment thereof, is purified using chromatography techniques (e.g., ion exchange chromatography, size exclusion chromatography, affinity chromatography) to produce the purified polypeptide including the in vitro carbamylated A1AT polypeptide, or fragment thereof.

In some embodiments, the in vitro carbamylated A1AT, or fragment thereof, is a human A1AT (hA1AT), or fragment thereof. In some embodiments, the in vitro carbamylated A1AT, or fragment thereof, is a bovine A1AT (bA1AT), or fragment thereof.

In some embodiments, the purified polypeptide including the in vitro carbamylated A1AT, or fragment thereof, is prepared by chemical synthesis, e.g., using solid phase peptide synthesis. In some embodiments, the A1AT, or fragment thereof, is in vitro carbamylated by replacing one or more lysine residues in the A1AT, or fragment thereof, with homocitrulline residues during the synthesis of the purified polypeptide. In some embodiments, the A1AT, or fragment thereof, is in vitro carbamylated by chemically or enzymatically modifying ε-amino-groups of one or more A1AT lysine residues.

In some embodiments, the A1AT, or fragment thereof, is in vitro carbamylated under conditions including a molar excess of a carbamylation reagent (e.g., isocyanic acid (HNCO), cyanate ([NCO]$^-$), organic compounds containing an isocyanate group, thiocyanate, or carbamoylphosphate) over the purified polypeptide including the A1AT, or fragment thereof. In some embodiments, the A1AT, or fragment thereof, is in vitro carbamylated under conditions including a molar excess of a carbamylation reagent over the lysine residues in the purified protein including the A1AT, or fragment thereof. In some embodiments, the molar excess of the carbamylation reagent is more than 3-fold, more than 5-fold, more than 10-fold, more than 30-fold, more than 100-fold, more than 300-fold, more than 1,000, more than 3,000-fold, or more than 10,000-fold over the purified polypeptide including the A1AT, or fragment thereof. In some embodiments, the molar excess of the carbamylation reagent is more than 3-fold, more than 5-fold, more than 10-fold, more than 30-fold, more than 100-fold, more than 300-fold, more than 1,000, more than 3,000-fold, or more than 10,000-fold over the lysine residues in the purified protein including the A1AT, or fragment thereof. In some embodiments, the purified polypeptide including the in vitro carbamylated A1AT, or fragment thereof, is cabamylated under conditions where the carbamylation reaction reaches a thermodynamic equilibrium.

In some embodiments, the purified polypeptide is a plurality of purified polypeptides, e.g., a library of purified polypeptides.

Methods for modifying proteins in vitro and in vivo are well known in the art. Exemplary methods can be found, e.g., in Lundblad R. L., *Chemical Reagents for Protein Modification*, CRC Press, 4$^{th}$ Edition (2014); Walker J. M., *The Protein Protocols Handbook* (Springer Handbooks), Humana Press, 3$^{rd}$ Edition (2009); Pollegioni L. and Servi S., *Unnatural Amino Acids: Methods and Protocols* (Methods in Molecular Biology, Vol. 794), Humana Press, 2012 Edition (2011).

Analytical methods for determining the degree of carbamylation in the purified polypeptide including the in vitro carbamylated A1AT, or fragment thereof, the position of carbamylated residues in the A1AT, or fragment thereof, and the homogeneity of carbamylated polypeptides in a population of purified polypeptides are well known in the art. Such methods include, e.g., liquid chromatography (LC), mass spectrometry (MS), high-pressure liquid chromatography (HPLC), capillary electrophoresis (CE), or combinations thereof (e.g., LC-MS).

Exemplary analytical methods for characterizing proteins and protein modifications can be found, e.g., in Whitelegge J., *Protein Mass Spectrometry*, Volume 52 (Comprehensive Analytical Chemistry), Elsevier Science, 1$^{st}$ Edition (2008); Wehr T. et al., *Basic HPLC and CE of Biomolecules*, Bay Bioanalytical Laboratory, 1$^{st}$ Edition (1998); Aguilar M-I, *HPLC of Peptides and Proteins: Methods and Protocols* (Methods in Molecular Biology), Humana Press, 2004 edition (2003).

In another aspect, the present disclosure relates to kits for detecting an anti-carbamylated protein (anti-CarP) antibody, for diagnosing, monitoring or prognosticating RA, or for determining the efficacy of an RA treatment in a subject, the kit including a purified polypeptide including an in vitro carbamylated A1AT, or fragment thereof, and one or more ancillary reagents. In some embodiments, the in vitro carbamylated A1AT, or fragment thereof, is a human polypeptide (hA1AT). In some embodiments, the in vitro carbamylated A1AT, or fragment thereof, is a bovine polypeptide (bA1AT).

Ancillary reagents can include, e.g., an immobilization buffer, an immobilization reagent, a dilution buffer, a secondary antibody, a detection reagent, a blocking buffer, a washing buffer, a detection buffer, a detection reagent, a stop solution, a system rinse buffer, and a system cleaning solution.

A skilled artisan will appreciate that numerous immobilization buffers are known in the art and that the selection of any specific coating buffer can be based, for example, on the nature of the coated surface (e.g., a Nunc Maxisorb microtiter plate) and the nature of the coated substrate (e.g., Car-A1AT). Coating buffers include, e.g., a sodium carbonate-sodium hydroxide buffers and phosphate buffers. In some embodiments, the coating buffer is 0.1M NaHCO$_3$ (e.g., about pH 9.6).

The kits of this disclosure can include any immobilization reagent known in the art, including covalent and non-covalent immobilization reagents. Covalent immobilization reagents can include any chemical or biological reagent that can be used to covalently immobilize a polypeptide of this disclosure on a surface. Covalent immobilization reagents can include, e.g., a carboxyl-to-amine reactive group (e.g., carbodiimides such as EDC or DCC), an amine reactive group (e.g., N-hydroxysuccinimide (NHS) esters, imidoesters), a sulfhydryl-reactive crosslinker (e.g., maleimides, haloacetyls, pyridyl disulfides), a carbonyl-reactive crosslinker groups (e.g., hydrazides, alkoxyamines), a photoreactive crosslinker (e.g., aryl azides, dizirines), or a chemoselective ligation group (e.g., a Staudinger reaction pair). Non-covalent immobiliazation reagents include any chemical or biological reagent that can be used to immobilize a polypeptide of this disclosure non-covalently on a surface, such as affinity tags (e.g., biotin) or capture reagents (e.g., streptavidin or anti-tag antibodies, such as anti-His$_6$ or anti-Myc antibodies).

The kits of this disclosure can include combinations of immobilization reagents. Such combinations include, e.g., EDC and NHS, which can be used, e.g., to immobilize a protein of this disclosure on a surface, such as a carboxylated dextrane matrix (e.g., on a BIAcore™ CM5 chip or a dextrane-based bead). Combinations of immobilization reagents can be stored as premixed reagent combinations or with one or more immobilization reagents of the combination being stored separately from other immobilization reagents.

A large selection of washing buffers are known in the art, such as tris(hydroxymethyl)aminomethane (Tris)-based buffers (e.g., Tris-buffered saline, TBS) or phosphate buffers (e.g., phosphate-buffered saline, PBS). Washing buffers typically include detergents, such as ionic or non-ionic detergents. In some embodiments, the washing buffer is a PBS buffer (e.g., about pH 7.4) including Tween 20 (e.g., about 0.05% Tween 20). In some embodiments, the washing buffer is the BIO-FLASH™ Special Wash Solution (INOVA Diagnostics, Inc., San Diego, Calif.).

Any dilution buffer known in the art can be included in a kit of this disclosure. Typical dilution buffers include a carrier protein (e.g., bovine serum albumin, BSA) and a detergent (e.g., Tween® 20). In some embodiments, the dilution buffer is PBS (e.g., about pH 7.4) including BSA (e.g., about 1% BSA) and Tween® 20 (e.g., about 0.05% Tween® 20).

Secondary antibodies can include, e.g., an anti-human IgA antibody, an anti-human IgD antibody, an anti-human IgE antibody, an anti-human IgG antibody, or an anti-human IgM antibody. In some embodiments, the secondary antibodies are anti-bovine antibodies. Secondary detection antibodies can be monoclonal or polyclonal antibodies. Secondary antibodies can be derived from any mammalian organism, including mice, rats, hamsters, goats, camels, chicken, rabbit, and others. Secondary antibodies can be conjugated to enzymes (e.g., horseradish peroxidase (HRP), alkaline phosphatase (AP), luciferase, and the like) or dyes (e.g., colorimetric dyes, fluorescent dyes, fluorescence resonance energy transfer (FRET)-dyes, time-resolved (TR)-FRET dyes, and the like). In some embodiments, the secondary antibody is a polyclonal rabbit-anti-human IgG antibody, which is HRP-conjugated.

In some embodiments, the detection reagent is a colorimetric detection reagent, a fluorescent detection reagent, or a chemiluminescent detection reagent. In some embodiments, the colorimetric detection reagent includes PNPP (p-nitrophenyl phosphate), ABTS (2,2'-azino-bis(3-ethylbenzothiazoline-6-sulphonic acid)) or OPD (o-phenylenediamine). In some embodiments, the fluorescent detection reagent includes QuantaBlu™ or QuantaRed™ (Thermo Scientific, Waltham, Mass.). In some embodiments, the luminescent detection reagent includes luminol or luciferin. In some embodiments, the detection reagent includes a trigger (e.g., $H_2O_2$) and a tracer (e.g., isoluminol-conjugate). In some embodiments, the detection reagent includes one or more BIO-FLASH™ Trigger solutions (INOVA Diagnostics, Inc., San Diego, Calif.).

Any detection buffer known in the art can be included in a kit of this disclosure. In some embodiments the detection buffer is a citrate-phosphate buffer (e.g., about pH 4.2).

Any stop solution known in the art can be included in a kit of this disclosure. The stop solutions of this disclosure terminate or delay the further development of the detection reagent and corresponding assay signals. Stop solutions can include, e.g., low-pH buffers (e.g., glycine-buffer, pH 2.0), chaotrophic agents (e.g., guanidinium chloride, sodium-dodecylsulfate (SDS)) or reducing agents (e.g., dithiothreitol, β-mecaptoethanol), or the like.

In some embodiments, the kits of this disclosure include cleaning reagents for automated assay systems. Automated assay systems can include systems by any manufacturer. In some embodiments, the automated assay systems include, e.g., the BIO-FLASH™, the BEST 2000™, the DS2™, the ELx50 WASHER, the ELx800 WASHER, the ELx800 READER, and the Autoblot S20™ (INOVA Diagnostics, Inc., San Diego, Calif.). Cleaning reagents can include any cleaning reagent known in the art. In some embodiments, the cleaning reagents are the cleaning reagents recommended by the manufacturers of the automated assay systems. In some embodiments, the cleaning reagents include the BIO-FLASH™ System Rinse or the BIO-FLASH™ System Cleaning solutions (INOVA Diagnostics, Inc., San Diego, Calif.).

In some embodiments, the kit further includes a solid support. The solid support can include any support known in the art on which a protein of this disclosure can be immobilized. In some embodiments, solid the solid substrates are microtiter well plates, slides (e.g., glass slides), chips (e.g., protein chips, biosensor chips, such as Biacore chips), microfluidic cartridges, cuvettes, beads (e.g., magnetic beads, xMAP® beads) or resins.

In some embodiments, the kits of this disclosure include a microtiter plate. In some embodiments, the microtiter plate is a 96-well plate, a 384-well plate, or a 1536-well plate. In some embodiments, the microtiter plate includes a protein of this disclosure immobilized in one or more wells of the microtiter plate. In some embodiments, the microtiter plate is a Nunc Maxisorp® plate (e.g., Fisher Scientific, Hampton, N.H., cat#430341).

In some embodiments, the kits of this disclosure include a cuvette. In some embodiments, the cuvette is a BIO-FLASH™ Cuvette (INOVA Diagnostics, Inc., San Diego, Calif.).

In some embodiments, the kits of this disclosure include beads or microspheres (e.g., xMAP® beads (Luminex; Austin, Tex.). In some embodiments, the beads are color-coded.

In some embodiments, the kits of this disclosure include one or more additional consumables. In some embodiments, the consumable is a sample cup (e.g., 1 ml, 5 ml, 10 ml, 25 ml, or 50 ml sample cup) or a screw cap. In some embodiments, the sample cup is a Falcon™ Tube (BD Biosciences, San Jose, Calif.) or the like. In some embodiments, the sample cup is a BIO-FLASH™ Sample Cup (INOVA Diagnostics, Inc., San Diego, Calif.). In some embodiments, the screw cap is a BIO-FLASH™ Screw Cap (INOVA Diagnostics, Inc., San Diego, Calif.).

In some embodiments, the kit further includes instructions for using the components of the kit for detecting anti-CarP antibodies in a sample from the subject.

The kits of this disclosure can be tailored to specific assay technologies. In some embodiments, the kits are ELISA kits, Dot Blot kits, chemiluminescence immunoassay (CIA) kits or multiplex kits. In some embodiments, the ELSA kits include a washing buffer, a sample diluents, a secondary antibody-enzyme conjugate, a detection reagent and a stop solution. In some embodiments, the Dot Blot kits include a washing buffer, a sample diluents, a secondary antibody-enzyme conjugate, a detection reagent, and a stop solution. In some embodiments, the CIA kit includes a washing buffer, a sample dilutent, a tracer (e.g., isoluminol-conjugate) and a trigger (e.g., $H_2O_2$). In some embodiments, the multiplex kit includes a washing buffer, a sample diluents and a secondary antibody-enzyme conjugate. In some embodiments, the kits are tailored to the Luminex platform and include, e.g., xMAP® beads.

In some embodiments, the kits of this disclosure are used to diagnose RA in a patient, to differentiate RA patient subpopulations (e.g., differentiate ACPA$^-$/anti-CarP$^+$ from ACPA$^-$/anti-CarP$^-$ patients), to prognosticate disease progression in RA patients (e.g., predict a more severe disease progression in ACPA⁻/anti-CarP⁺ relative to ACPA⁻/anti-CarP⁻ patients or predict the development of clinical symptoms in arthralgia patients), to monitor the efficacy of RA treatments or to predict treatment outcomes. In some embodiments, the RA treatments include drug treatments. In some embodiments, the drug treatments include treatments with prednisone, meloxicam, celebrex, mobic, naproxen, remicade IV, plaquenil, methotrexate, diclofenac, methylprednisolone, enbrel, indomethacin, ibuprofen, kenalog, etodolac, nabumetone, humira, aleve, minocycline, orencia, rituxan, or any FDA or EMA-approved RA drug, including experimental RA drugs in clinical development. In some embodiments, the kits are used as companion diagnostics for RA treatments. In some embodiments, the kits of this disclosure are used to select patients specific RA drug treatments.

In some embodiments, the kits include a packaging having a label indicating the kit is used for diagnosis, prognosis or monitoring of RA or a RA subtype. The RA subtypes can be defined, e.g., according to clinical disease symptoms, or the presence or absence of genomic or proteomic biomarkers known in the art (e.g., ACPAs). In some embodiments, the label is approved by a governmental regulatory agency. In some embodiments, the label is approved by the United States Food and Drug Administration (FDA), the European Medicines Agency (EMA), the China Food and Drug Administration (CFDA) or the Japanese Ministery of Health Labor and Welfare (MHLW). FDA approved labels can include notification of an FDA-approved use and instructions therefore. In some embodiments, the kits are labeled for Research Use Only (RUO) or for Investigational Use Only (IUO). In some embodiments, the kits are labeled for In Vitro Diagnostic Use (IVD). In some embodiments, the kits are labeled in accordance with Title 21, Code of Federal Regulations, Section 809, Subpart B (21 CFR 809, Subpart B). In some embodiments, the RUO, IUO, or IVD labels of the kits describe the use of the kits for the diagnosis of RA. In some embodiments, the RUO, IUO, or IVD labels of the kits describe the use of the kits for the diagnosis of an RA subtype. In some embodiments, the RUO, IUO, or IVD labels of the kits describe the use of the kits for the prognostication of RA. In some embodiments, the kits are labeled as IVD companion diagnostic devices. In some embodiments, the kits are labeled as IVD companion diagnostic devices for uses with a RA drug such as prednisone, meloxicam, celebrex, mobic, naproxen, remicade IV, plaquenil, methotrexate, diclofenac, methylprednisolone, enbrel, indomethacin, ibuprofen, kenalog, etodolac, nabumetone, humira, aleve, minocycline, orencia, rituxan, or any FDA-approved RA drug, including experimental RA drugs in clinical development.

In another aspect, this disclosure provides methods for detecting anti-carbamylated protein (anti-CarP) antibodies in a subject including: a) contacting a sample from the subject with a purified polypeptide including an in vitro carbamylated human alpha 1 antitrypsin (hA1AT), or fragment thereof, to form a complex between an anti-CarP antibody and the purified polypeptide; and b) detecting the presence or absence of an anti-CarP antibody-purified polypeptide complex in the sample.

In some embodiments, the presence or absence of the anti-CarP antibody-polypeptide complex is detected by an enzyme-linked immunosorbent assay (ELISA), a fluorescent immunosorbent assay (FIA), a chemiluminescence immuno assay (CIA), a radioimmunoassay (MA), an enzyme multiplied immunoassay, a solid phase radioimmunoassay (SPROA), a fluorescence polarization (FP) assay, a fluorescence resonance energy transfer (FRET) assay, a time-resolved fluorescence resonance energy transfer (TR-FRET) assay, a surface plasmon resonance (SPR) assay, or a Dot-Blot assay.

In some embodiments, the ELISA is a sandwich ELISA. In some embodiments, the sandwich ELISA includes the initial step of immobilizing a purified polypeptide of this disclosure on a solid support (e.g., on the wall of a microtiter plate well or of a cuvette). In some embodiments, contacting the sample from the subject with the purified polypeptide of this disclosure includes exposing the sample to the immobilized purified polypeptide.

In some embodiments, the ELISA is a direct ELISA. In some embodiments, the direct ELISA includes the initial step of immobilizing the anti-CarP antibodies in the sample on a solid support (e.g., on the wall of a microtiter plate well or of a cuvette). In some embodiments, contacting the sample from the subject with the purified polypeptide of this disclosure includes exposing a purified polypeptide of this disclosure to the immobilized the anti-CarP antibodies.

In some embodiments, the presence or absence of the anti-CarP antibody-polypeptide complex is detected concurrently with the presence or absence of another analyte (e.g., another biomarker or disease marker) in a multiplex assay. In some embodiments, the presence of absence of the anti-CarP antibody-polypeptide complex is detected concurrently with the presence or absence of an ACPA-ACP complex in a multiplex assay.

Methods and protocols for conducting immunoassays and biophysical protein-interaction assays are well known in the art. See, e.g., Wild D., *The Immunoassay Handbook*, Elsevier Science, 4ᵗʰ Edition (2013); Fu H., Protein-Protein Interactions, Humana Press, 4ᵗʰ Edition (2004).

In some embodiments, the methods for detecting anti-CarP antibodies are performed according to the following protocol. First, a purified in vitro carbamylated polypeptide of this disclosure (Car-A1AT) and an uncarbamylated A1AT negative control are diluted in coating buffer to prepare 10 µg/ml Car-A1AT and A1AT solutions. 50 µl of the Car-A1AT solution is dispensed into positive control wells and test wells of a 96-well microtiter plate. 50 µl of the A1AT solution is dispensed into the negative control wells on the same 96-well microtiter plate. The microtiter plate and polypeptide solutions are incubated overnight at 4° C. Next, 100 µl blocking buffer are added to the positive control, negative control and test wells of the microtiter plate and the plate is incubated for an additional 6 hours at 4° C. At the end of the incubation period, the plate is washed three times with washing buffer. Serum test samples (having unknown anti-CarP antibody contents) are diluted 50-fold in dilution buffer; positive control standards are prepared using serum samples known to contain anti-CarP antibodies (e.g., as single concentration standards or dilution series) and negative control samples are prepared using dilution buffer alone or serum samples known not to contain anti-CarP antibodies. After removing the washing buffer from the microtiter plate, 50 µl of the test samples, positive control samples, and negative control samples are added to the test, negative control and positive control wells on the microtiter plate, respectively. Next, the microtiter plate is incubated overnight at 4° C. on ice. On the next day, the microtiter plate is washed three times with washing buffer. Rabbit anti-human-IgG-HRP is diluted 1:5,000 in dilution buffer and 50 µl of the antibody-conjugate is added to each microtiter plate well after removing the washing buffer. After 3.5 hours incubation at 4° C. on ice the microtiter plate is wash another three times with washing buffer. A detection substrate solution is prepared by adding 5 μl H$_2$O$_2$ to per 10 ml ABTS solution (concentration according to manufacturer's instructions). 50 μl of the detection substrate solution is added to each microtiter plate well after removing the washing buffer. The microtiter plate is then incubated in the dark at room temperature for 0.5-5 min and read on an ELISA reader. The relative absorbance signals for the negative control wells (e.g., average or median signals) are subtracted from the signals obtained for the test well and positive control wells. Test serum samples resulting in significant absorbance signals above background (e.g., 2 standard deviations (STDs) above the negative control well signals) are considered anti-CarP antibody positive. Anti-CarP antibodies can be quantified in anti-CarP antibody positive samples by comparing the relative absorbance signals of the test wells with the absorbance signals observed for the positive control cells.

In some embodiments, the methods of this disclosure are performed, at least in part, using one or more automated assay systems. In some embodiments, the automated assay system include, e.g., a BIO-FLASH™, a BEST 2000™, a DS2™, an ELx50 WASHER, an ELx800 WASHER, an ELx800 READER, and an Autoblot S20™ (INOVA Diagnostics, Inc., San Diego, Calif.).

In some embodiments, the methods for detecting an anti-CarP antibody further include the initial step of preparing a purified polypeptide of this disclosure. In some embodiments, the purified polypeptide is a recombinant protein prepared from cDNA. In some embodiments, the purified polypeptide is an A1AT, or fragment thereof, prepared from blood, plasma, serum, synovial fluid, or other tissue or bodily fluid.

In some embodiments, the purified polypeptide including the in vitro carbamylated A1AT, or fragment thereof, is prepared by (a) purifying a polypeptide including an A1AT, or fragment thereof, and (b) in vitro carbamylating the A1AT, or fragment thereof. In some embodiments, the purified polypeptide is prepared by first purifying the polypeptide, while the A1AT is in an uncarbamylated state, and then in vitro carbamylating the A1AT, or fragment thereof in the purified polypeptide. In some embodiments, the purified polypeptide is prepared by first in vitro carbamylating the A1AT, or fragment thereof, while the polypeptide is in an unpurified state, e.g., in a biological mixture (e.g., a cell lysate or a blood, serum or plasma sample), and then purifying the polypeptide including the in vitro carbamylated A1AT, or fragment thereof.

In some embodiments, the A1AT (e.g., hA1AT or bA1AT), or fragment thereof, includes one or more anti-CarP antibody binding sites, each of which can independently be in a carbamylated state or an uncarbamylated state, and where anti-CarP antibodies from human subjects bind to the anti-CarP antibody binding sites in their carbamylated states, but not their uncarbamylated states, to form purified polypeptide-antiCarP antibody complexes.

In some embodiments, anti-CarP antibody binding sites are recognized by an anti-CarP antibody in an amino acid sequence-independent manner. Anti-CarP antibody binding sites recognized in a sequence-independent manner include a cabamylated lysine (K(Car); homocitrulline) residue, and no additional residues. In some embodiments, anti-CarP antibody binding sites are recognized by an anti-CarP antibodies in a sequence-specific manner. Anti-CarP antibody binding sites recognized in a sequence-specific manner include a cabamylated lysine (K(Car); homocitrulline) residue, and one or more additional residues of the A1AT, or fragment thereof. The one or more additional residues of the A1AT, or fragment thereof, can form part of a linear epitope or a non-linear epitope. The one or more additional residues of A1AT, or fragment thereof, can include, e.g., one additional residue, two additional residues, two or more additional residues, three or more additional residues, four or more additional residues, five or more additional residues, six or more additional residues, seven or more additional residues, eight or more additional residues, nine or more additional residues, 10 or more additional residues, 12 or more additional residues, 14 or more additional residues, 16 or more additional residues, 18 or more additional residues, or 20 or more additional residues.

In some embodiments, anti-CarP antibody binding sites are bound by anti-CarP antibodies in their carbamylated state, but not in their uncarbamylated state. In some embodiments, anti-CarP antibody binding sites are bound by anti-CarP antibodies with higher affinity in their carbamylated state than in their uncarbamylated state. In some embodiments, anti-CarP antibody binding sites are bound by anti-CarP antibodies with more than 2-fold, more than 3-fold, more than 4-fold, more than 5-fold, more than 8-fold, more than 10-fold, more than 15-fold, more than 20-fold, more than 25-fold, more than 50-fold, more than 100-fold, more than 300-fold, more than 1,000-fold, more than 3,000-fold, more than 10,000-fold, more than 30,000-fold, or more than 100,000-fold greater binding affinity in their carbamylated state than in their uncarbamylated state. Greater binding affinities are evidenced, e.g., by lower dissociation constants (KDs) for the anti-CarP antibody-Car-A1AT complex or by higher association constants (KAs) for the respective anti-CarP antibody and Car-A1AT. In some embodiments, the dissociation constants for (KDs) for the anti-CarP antibody-Car-A1AT complexes are less than 1 mM, less than 300 nM, less than 100 nM, less than 30 nM, less than 10 nM, less than 3 nM, less than 1 nM, less than 300 pM, less than 100 pM, less than 30 pM, less than 10 pM, less than 3 pM, or less than 1 pM. Methods for measuring binding affinities of antibodies (e.g., anti-CarP antibodies) to antigens (e.g., Car-A1AT) are well known in the art and include, e.g., ELISA, isothermal titration calorimetry (ITC) and surface plasmon resonance (SPR).

Complexes of anti-CarP antibodies and a purified polypeptide with in vitro-carbamylated A1AT, or fragment thereof, can have a stoichiometry of one to one or more anti-CarP antibodies. In some embodiments, the complexes have one anti-CarP antibody per purified polypeptide. In some embodiments, the complexes have two anti-CarP antibodies per purified polypeptide. In some embodiments, the complexes have more than two anti-CarP antibodies per purified polypeptide. Methods for measuring binding stoichiometries of antibodies (e.g., anti-CarP antibodies) to antigens (e.g., Car-A1AT) are well known in the art and include, e.g., isothermal titration calorimetry (ITC) and ultracentrifugation.

In some embodiments, the complexes of anti-CarP antibodies and purified polypeptides with in vitro-carbamylated A1AT, or fragment thereof, are a plurality of complexes with identical stoichiometry. For example, all complexes in the plurality of complexes have one anti-CarP antibody per purified polypeptide. In some embodiments, the complexes of anti-CarP antibodies and purified polypeptides with in vitro-carbamylated A1AT, or fragment thereof, are a plurality of complexes with different stoichiometries. For example, some complexes in the plurality of complexes can have one anti-CarP antibody per purified polypeptide and some other complexes in the plurality of complexes can have more than one anti-CarP antibody per purified polypeptide.

In some embodiments, the purified polypeptide-anti-CarP antibody complexes are formed in solution. In some embodiments, the purified polypeptide-anti-CarP antibody complexes are formed on a solid surface. In some embodiments the purified polypeptide-anti-CarP antibody complexes are formed by first immobilizing the purified polypeptide on the surface and then contacting the anti-CarP antibodies in solution with the immobilized purified polypeptide. In some embodiments the purified polypeptide-anti-CarP antibody complexes are formed by first immobilizing the anti-CarP antibodies on the surface and then contacting the purified polypeptide in solution with the immobilized anti-CarP antibodies.

In some embodiments, the methods for detecting anti-CarP antibodies further include coating the purified polypeptide on a surface or solid support.

In some embodiments, the subject is suspected of having RA.

In some embodiments, the methods for detecting anti-CarP antibodies further include obtaining a sample from the subject. In some embodiments, the sample is a plurality of samples. In some embodiments, the sample is a blood sample, a plasma sample, a serum sample, a synovial fluid sample or another tissue or bodily fluid sample.

In some embodiments, a plurality of samples were obtained over a period of time. In some embodiments, the period of time is more than 12 hours, more than 1 day, more than 2 days, more than 3 days, more than 4 days, more than 5 days, more than 6 days, more than 7 days, more than 10 days, more than 14 days, more than 3 weeks, more than 1 month, more than 2 months, more than 3 months, more than 4 months, more than 5 months, more than 6 months, more than 9 months, more than 12 months, more than 18 months, more than 24 months, more than 30 months, more than 3 years months, more than 4 years, or more than 5 years.

In some embodiment one or more samples were obtained before the subject received a RA treatment (e.g., a drug regimen to treat or prevent RA). In some embodiments, one or more samples were obtained after the subject received a RA treatment or during the course of an ongoing RA treatment period.

In some embodiments, a purified polypeptide of this disclosure is immobilized on a surface. In some embodiments, the purified polypeptide is coated on a surface of a microtiter plate (e.g., a 96-well plate, 384-well plate, or 1536-well plate), a slide (e.g., a glass slide) or a cuvette. In some embodiments the purified protein is coated on the surface as an unfolded polypeptide. In some embodiments, the purified protein is coated on the surface in its native form. In some embodiments, coating the purified polypeptide to the surface includes physical adsorption of the polypeptide to the surface. In some embodiments, coating the purified polypeptide to the surface includes covalent linkage of the polypeptide to the surface.

In another aspect, the present disclosure relates to methods of diagnosing RA in a subject suspected of having RA, including: a) contacting a sample from the subject with a purified polypeptide including an in vitro carbamylated A1AT, or fragment thereof, to form a complex between an anti-CarP antibody of the sample and the purified polypeptide; and b) detecting the presence or absence of an anti-CarP antibody-purified polypeptide complex, where the presence of the anti-CarP antibody-purified polypeptide complex in the sample indicates that the subject has RA.

In some embodiments, detecting the presence or absence of the anti-CarP antibody-purified polypeptide complex includes determining the levels of an anti-CarP antibody in the sample. Methods for determining anti-CarP antibody levels in a sample (e.g., in mg/ml or nM/ml) can be determined by any method known in the art (e.g., ELISA).

In some embodiments, higher levels of an anti-CarP antibody in the sample indicate a more severe course of future disease progression in a RA patient than lower levels of the anti-CarP antibody. In some embodiments, higher levels of an anti-CarP antibody in the sample indicate more severe joint erosion than lower levels of the anti-CarP antibody.

The severity of disease progression, e.g., with respect to the severity of clinical symptoms such as joint pain or joint erosion, can be determined by a skilled artisan, such as a physician (e.g., a general practitioner or a rheumatologist).

In another aspect, the present disclosure relates to methods of determining the prognosis of rheumatoid arthritis (RA) in a human subject, including a) contacting a sample from the subject with a purified polypeptide including an in vitro carbamylated hA1AT, or fragment thereof, to form a complex between an anti-CarP antibody and the purified polypeptide, and b) detecting the presence or absence of the anti-CarP antibody-purified polypeptide complex, wherein the presence or absence of the anti-CarP antibody-purified polypeptide complex indicates the course of RA progression in the human subject.

In some embodiments, the human subject is an asymptomatic subject suspected to be at risk of developing RA. In some embodiments, the presence of the anti-CarP antibody-purified polypeptide complex in the sample indicates that the patient is at a greater risk of developing RA than the absence of the anti-CarP antibody-purified polypeptide complex.

In some embodiments, the human subject is a RA patient having a clinical symptom of RA. In some embodiments, the presence of the anti-CarP antibody-purified polypeptide complex in the sample predicts a more severe clinical course of RA disease progression than the absence of the anti-CarP antibody-purified polypeptide complex.

In some embodiments, detecting the presence or absence of the anti-CarP antibody-purified polypeptide complex in the sample includes determining the levels of an anti-CarP antibody in the sample. In some embodiments, higher levels of the anti-CarP antibody indicate a higher risk that an asymptomatic subject will develop RA than lower levels of the anti-CarP antibody. In some embodiments, higher levels of the anti-CarP antibody indicate a more severe course of future disease progression in a RA patient than lower levels of the anti-CarP antibody. In some embodiments, higher levels of the anti-CarP antibody indicate a more rapid onset of RA than lower levels of the anti-CarP antibody.

In some embodiments, the presence of an anti-CarP antibody in a sample from a subject suspected to be at risk of developing RA indicates that the subject is an arthralgia patient. In some embodiments, the presence of the anti-CarP antibody indicates that an arthralgia patient has an about 10%-20% greater chance of developing RA over the next 1 year, 2, years, 3 years, 4 years, or 5 years after detecting the presence of an anti-CarP antibodies than an arthralgia patient not having anti-CarP antibodies. In some embodiments, the presence of an anti-CarP antibody indicates that the arthralgia patient has a ≥50% chance of developing RA over the next 1 year, 2 years, 3 years, 4 years, or 5 years after detecting the presence of the anti-CarP antibody than an arthralgia patient not having the anti-CarP antibody.

In some embodiments, the human subject is an arthralgia patient. In some embodiments, the presence of the anti-CarP antibody-purified polypeptide complex in the arthralgia patient indicates an about 10-20% greater risk that the arthralgia patient will develop RA within five years from determining the presence of the anti-CarP antibody-purified polypeptide complex than the absence of the anti-CarP antibody-purified polypeptide complex.

In some embodiments, the methods of this disclosure further include detecting the presence or absence of an ACPA-antibody in the sample from the subject. In some embodiments, the sample is negative for the anti-citrullinated protein antibody (ACPA).

In some embodiment, the presence of anti-CarP antibodies in the absence of ACPA-antibodies predicts a more severe clinical course of disease progression (e.g., associated with more severe joint damage or more severe radiological damage) than the absence of anti-CarP antibodies and ACPA-antibodies. Assays for detecting and quantifying ACPA-antibodies are known in the art (e.g., ACPA-ELISA).

In some embodiments, detecting the presence or absence of the anti-CarP antibody-purified polypeptide complex includes establishing a level of the anti-CarP antibody in the sample. Anti-CarP antibody levels can be expressed, e.g., as anti-CarP antibody concentrations in the sample (e.g., in [mg/ml] or [nM]).

In some embodiments, detecting the presence or absence of the anti-CarP antibody-polypeptide complex includes comparing the level of anti-CarP antibody in a sample from a subject to a control level of anti-CarP antibody in a sample from a healthy control individual, where if the level of CarP-antibody in the sample from the subject is greater than the control level, this indicates that the subject has rheumatoid arthritis (RA).

In some embodiments, detecting the presence or absence of the anti-CarP antibody-polypeptide complex includes comparing the level of anti-CarP antibody in a sample from a subject to a control level of anti-CarP antibody in a sample from a healthy control individual, where if the level of CarP-antibody in the sample from the subject is greater than the control level, this indicates that the subject is at risk of developing RA in the future.

In some embodiments, detection of an increased level of anti-CarP antibody (e.g., relative to an average or median anti-CarP antibody level observed in a population of healthy control subjects) indicates that the subject is at risk of developing clinical symptoms of RA (e.g., joint pain, systemic inflammation of synovial joints) within less than 3 months, less than 6 months, less than 9 months, less than 12 months, less than 18 months, less than 2 years, less than 3 years, less than 4 years, less than 5 years, less than 6 years, less than 7 years, less than 8 years, less than 9 years, less than 10 years, less than 12 years, less than 14 years, or less than 16 years from the determination of the increased anti-CarP antibody level.

In some embodiments, detection of an increased level of anti-CarP antibody indicates that the subject is more than 5%, more than 10%, more than 15%, more than 20%, more than 25%, more than 30%, more than 35%, more than 40%, more than 45%, more than 50%, more than 60%, more than 70%, or more than 80%, or more than 90% more likely to develop clinical symptoms of RA within 5 years following the determination of the increased anti-CarP antibody level than a control group of subjects who do not have the increased levels of anti-CarP antibody. In some embodiments, detection of an increased level of anti-CarP antibody indicates that the subject is more than 2-fold, more than 3-fold, more than 4-fold, more than 5-fold, more than 6-fold, more than 7-fold, more than 8-fold, more than 9-fold, or more than 10-fold more likely to develop clinical symptoms of RA within 5 years following the determination of the increased anti-CarP antibody level than a control group of subjects who do not have the increased level of anti-CarP antibody.

In some embodiments, the anti-CarP antibody in the control individuals is absent. In some embodiments, the anti-CarP antibody is considered absent in a sample if an anti-CarP antibody level cannot be detected above the noise of the respective assay used to determine the anti-CarP antibody level. In some embodiments, the anti-CarP antibody is considered present in a sample if the anti-CarP antibody level can be detected above the noise of the respective assay used to determine the anti-CarP antibody level. In some embodiments, the anti-CarP antibody is considered present in a test sample if the test sample signal in the anti-CarP antibody detection assay is at least two standard deviations (2×STD) above the background noise (e.g., the average or mean signal for negative control samples). In some embodiments, the anti-CarP antibody is considered present in the sample if the level of anti-CarP antibody exceeds a predetermined threshold level. The anti-CarP threshold level can be determined by a skilled artisan, e.g., a clinical physician, based on a variety of factors, such as the specific objectives of a clinical trial or the medical (e.g., diagnostic, prognostic) significance of a certain anti-CarP antibody level or the results of another diagnostic test for RA that does not involve the detection of the anti-CarP antibody level.

In another aspect, the present disclosure relates to methods of determining or monitoring the efficacy of an RA treatment in a RA patient, including: a) contacting two or more samples obtained from the patient at a first and a subsequent time point throughout the course of the RA treatment with a purified polypeptide including an in vitro carbamylated A1AT (e.g., hA1AT or bA1AT), or fragment thereof, to form a complex between an anti-CarP antibody of the two or more samples and the purified polypeptide; b) determining a level of the anti-CarP antibody for each of the two or more samples, and c) comparing the level of the anti-CarP antibody between the two or more samples, where a decreased level of the anti-CarP antibody in one or more samples obtained at the subsequent time point relative to the level of the anti-CarP antibody obtained at the first time point indicates that the RA treatment is efficacious and a stable or increased level of the anti-CarP antibody indicates that the RA treatment is not efficacious.

In some embodiments, one or more samples were obtained at the beginning of the course of the RA treatment and one or more samples were obtained at later time points throughout the course of the RA treatment.

In some embodiments, the subsequent time points are 2 or more, 3 or more, 4 or more, 5 or more, 6 or more, 7 or more, 8 or more, 9 or more, 10 or more, 15 or more, 20 or more, 25 or more or 30 or more time points.

In some embodiments, the RA treatments include drug treatments. In some embodiments, the drug treatments include a treatment with prednisone, meloxicam, celebrex, mobic, naproxen, remicade IV, plaquenil, methotrexate, diclofenac, methylprednisolone, enbrel, indomethacin, ibuprofen, kenalog, etodolac, nabumetone, humira, aleve, minocycline, orencia, rituxan, or other FDA or EMA-approved RA drugs, including experimental RA drugs in clinical development. In some embodiments, the RA treatments include treatments with a combination of two or more RA drugs.

In some embodiments, the methods further include adjusting the RA treatment if the treatment was determined to be not efficacious. Adjusting the RA treatment can include, e.g., adjusting the dose of a drug treatment, increasing the frequency of a drug treatment, treating with a different drug or combination of drugs, ending the RA treatment.

In some embodiments, the methods further include repeating the RA treatment if the treatment was determined to be efficacious.

In some embodiments, the methods of this disclosure further include administering an RA treatment to a RA patient or a subject at risk of developing RA. The RA treatment can be administered one or more times (e.g., 1 or more times, 2 or more times, 3 or more times, 4 or more times, 5 or more times, 6 or more times, 7 or more times, 8 or more times, 9 or more times, 10 or more times, 15 or more times, 20 or more times, 25 or more times, 50 or more times, 100 or more times, 150 or more times, 200 or more times, 300 or more times, 400 or more times, or 500 or more times). In some embodiments, the RA treatment is administered over a period of time (e.g., 1 day or more, 1 week or more, 2 weeks or more, 1 month or more, 2 months or more, 3 months or more, 6 months or more, 9 months or more, 12 months or more, 18 months or more, 2 years or more, or 3 years or more). In some embodiments, the RA treatment is administered, once daily, twice daily or three-times daily. In some embodiments, the RA treatment is administered once per week, once every two weeks, or once per month.

In another aspect, the present disclosure relates to methods of selecting a subject for a RA treatment, including: a) detecting the presence or absence of an anti-CarP antibody in a sample from the subject according to a method of this disclosure; b) optionally detecting the presence or absence of one or more additional RA biomarkers in the sample, and c) selecting the subject for the RA treatment based on the presence or absence of the anti-CarP antibody and, optionally, based on the presence or absence of the one or more additional RA biomarkers.

Additional RA biomarkers can include any RA biomarker known in the art. In some embodiments, the additional RA biomarkers include RA-specific autoantigens. In some embodiments, the additional RA biomarkers include ACPAs, Ra33 (hnRNP A2), fibrinogen, fibronectin, alpha-enolase, type II collagen, immunoglobulin binding protein (BiP), annexin, viral citrullinated peptide (VCP) derived from Epstein Barr Virus-encoded protein (EBNA-2), and antibodies directed to peptidyl arginine deiminase type 4 (PAD4) and to B-RAF. Methods for detecting the presence or absence of additional RA biomarkers are known in the art (e.g., ELISA, western blot, and the like).

From the foregoing description, it will be apparent that variations and modifications can be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

The following examples are provided by way of illustration, not limitation.

Example I

Identification of Bovine Car-A1AT as a Major Car-FCS Antigen Recognized by Anti-CarP Antibodies of Rheumatoid Arthritis Patients This example illustrates the identification of carbamylated bovine α(1)-antitrypsin (Car-A1AT or Ca-A1AT) as an immunological target in carbamylated fetal calf serum (Car-FCS or Ca-FCS) of anti-carbamylated protein (anti-CarP) antibodies found in the serum of human rheumatoid arthritis (RA) patients.

Car-FCS was produced by reacting FCS with potassium cyanate. In brief, A 2M solution of potassium cyanate (KOCN, Sigma-Aldrich, St. Louis, Mo.; cat no. 215074-500G) was prepared in PBS. The 2M KOCN solution was then mixed with FCS (Bodinco, Alkmaar, The Netherlands) in a 1:1 volume-by-volume proportion. The mixed FCS-KOCN solution was incubated overnight at 37° C. to produce Car-FCS. Following the incubation period, the Car-FCS solution was dialyzed against PBS (2 L) for 48 hrs, during which the PBS was refreshed 5 times.

Car-FCS was then subjected to HPLC-fractionation over an ion exchange column. The protein content of HPLC fractions was analyzed on SDS-PAGE gels and the immunoreactivity of Car-FCS HPLC fractions was tested by ELISA. See, e.g., FIGS. 2A and 3A.

ELISAs were performed as follows. In brief, unmodified FCS and Car-FCS were coated overnight on NUNC MAXISORP® plates (Thermo Scientific, Waltham, Mass.). Following washing and blocking, the wells were incubated with serum samples obtained from human RA patients and healthy volunteers. Bound human IgG was detected using rabbit anti-human IgG antibodies (Dako, Glostrup, Denmark), followed by HPR-labeled goat anti-rabbit IgG antibody (Dako, Glostrup, Denmark). Following additional wash steps, HPR enzyme activity was measured using ABTS substrate (Pierce, Rockford, Ill.). The cut-off for a positive response was chosen as the mean plus two times the standard deviation (SD) of the specific anti-CarP reactivity of healthy controls.

Figure 2A:
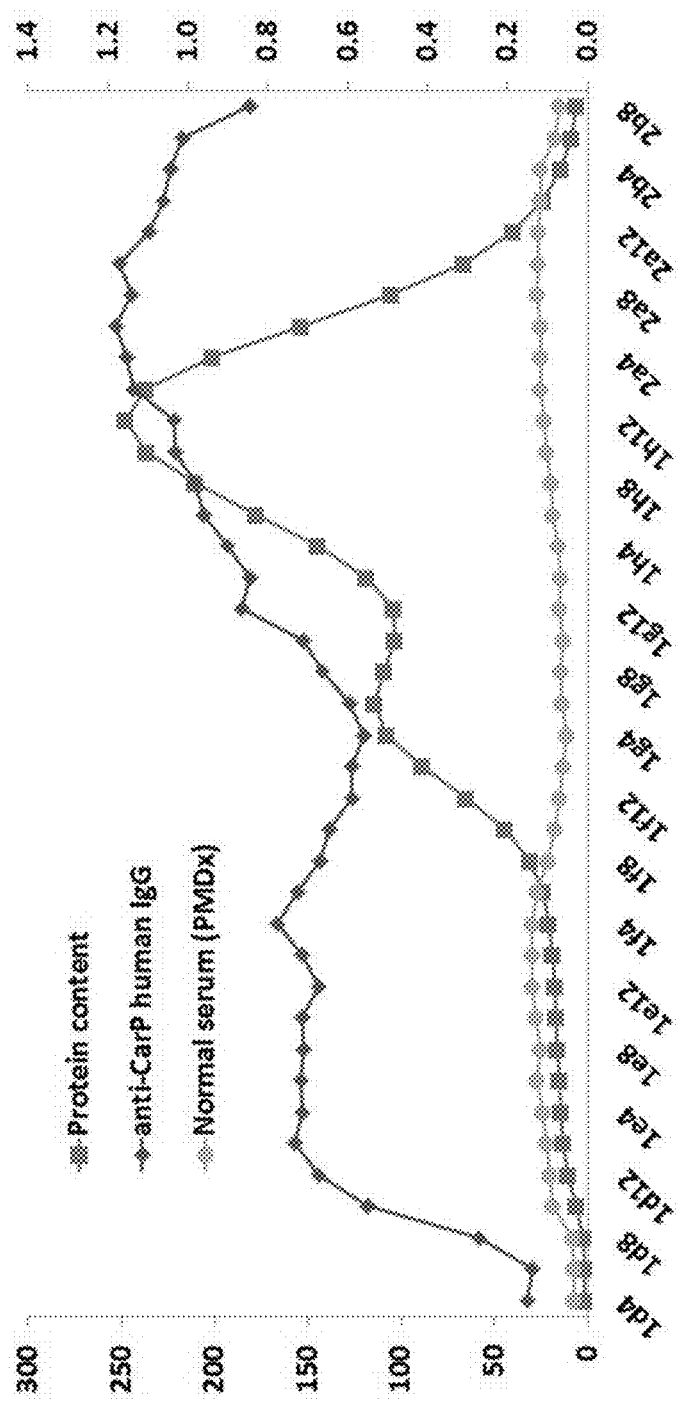
FIGS. 2A-B show graphs illustrating the fractional ELISA analysis of carbamylated fetal calf serum (Car-FCS), separated by ion-exchange HPLC (MonoQ).
Figure 2B:
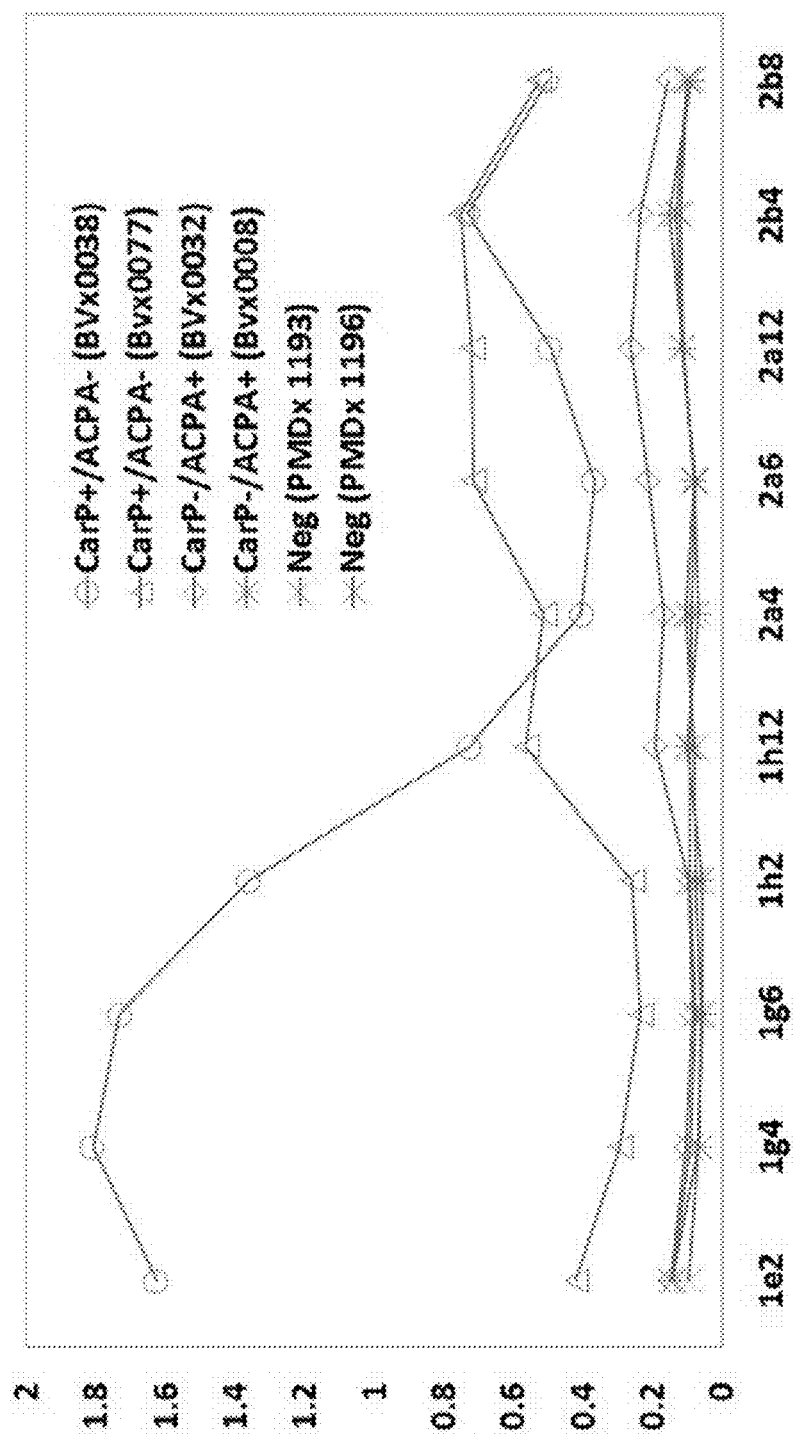
Figure 3A:
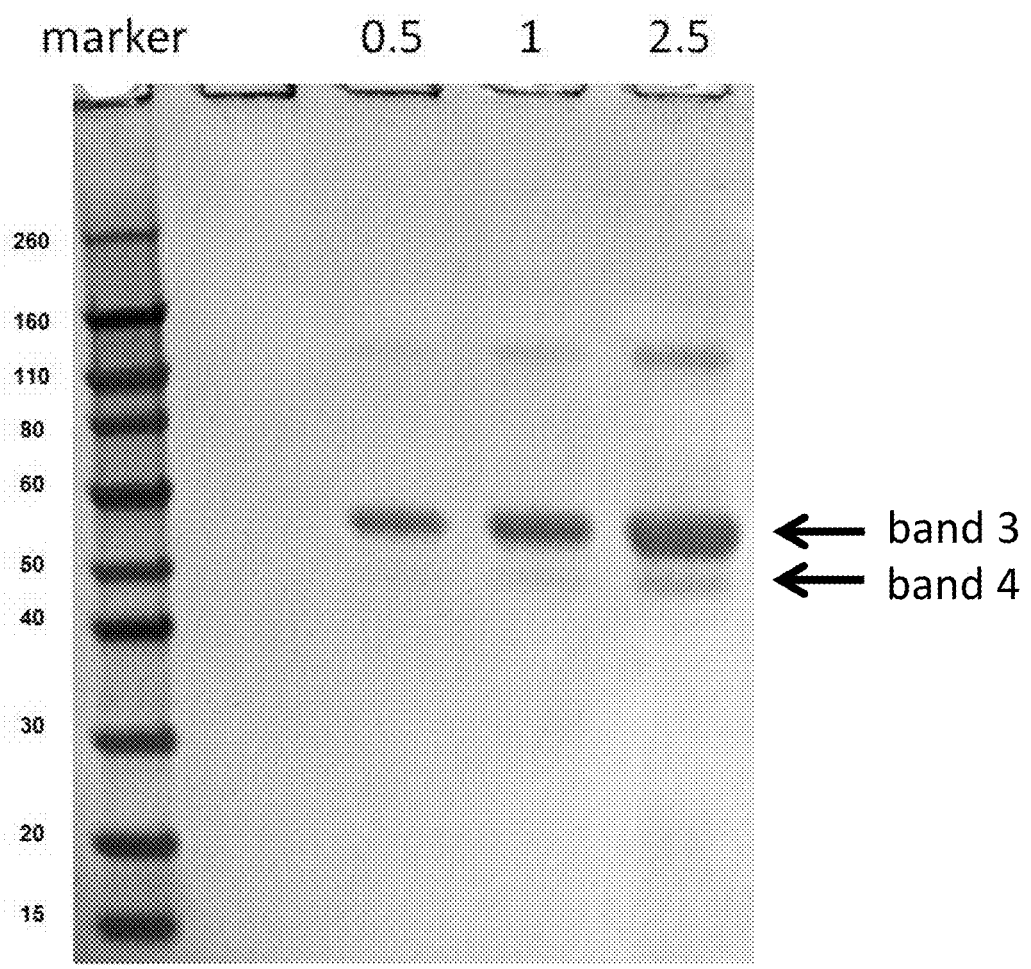
FIGS. 3A-C illustrate the identification of A1AT as the major carbamylated protein in HPLC-fraction 1G4.
Figure 3B:
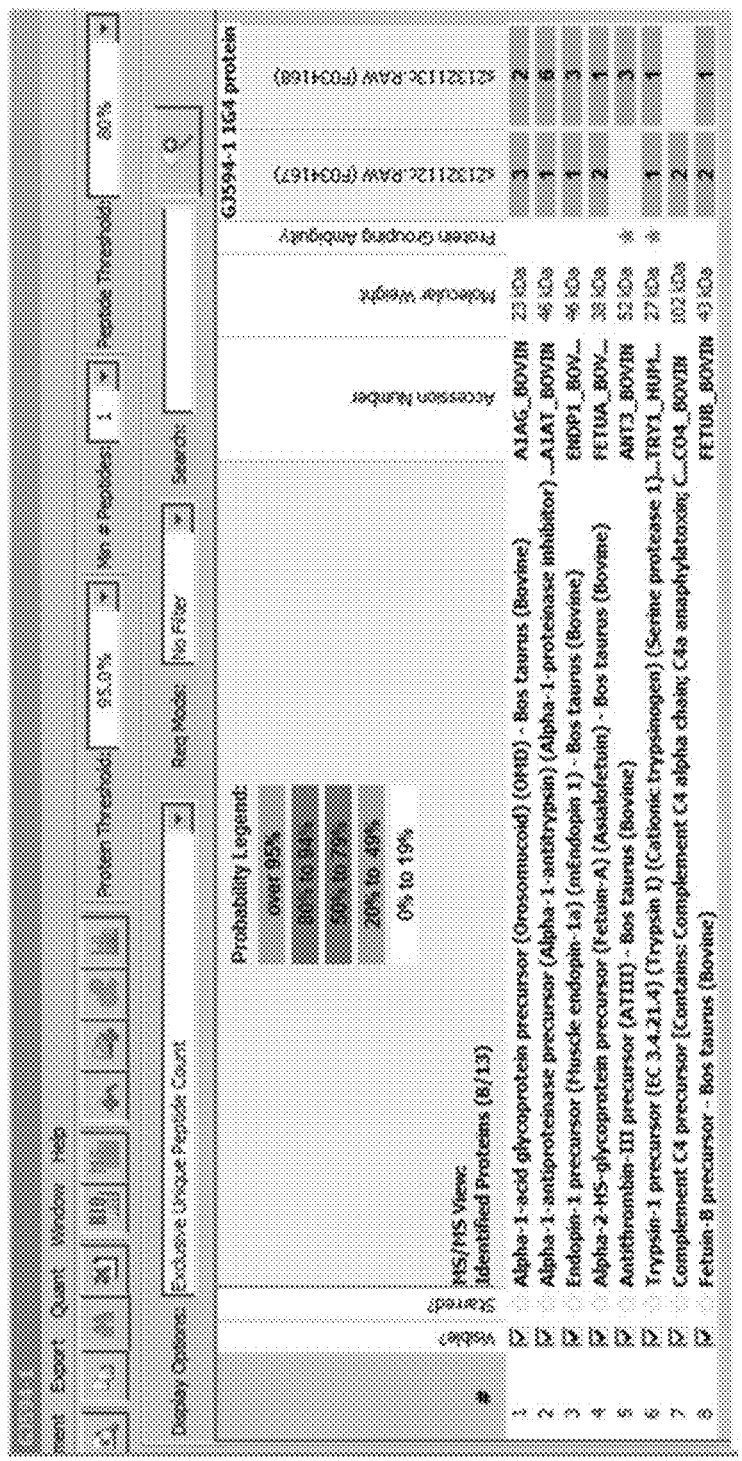
Figure 3C:
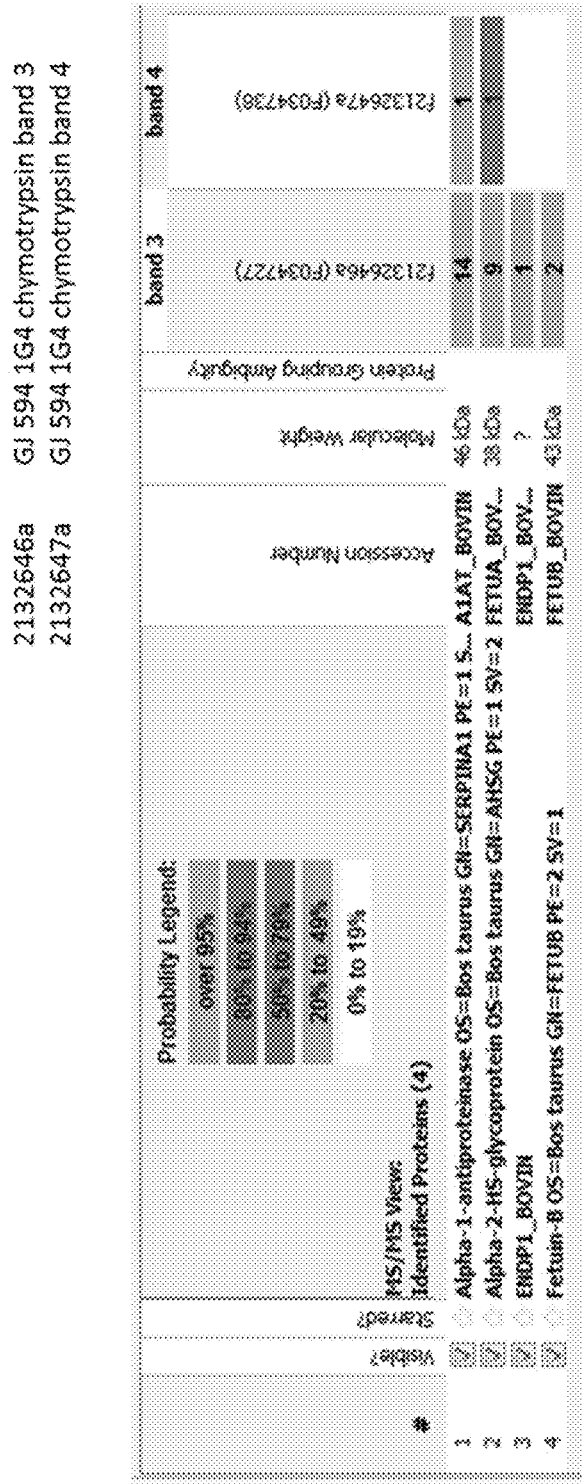

Car-FCS was fractionated by ion-exchange HPLC using a MonoQ column. HPLC fractions were analyzed by SDS-PAGE (4-12%) for their overall protein content and by ELISA for their content of carbamylated proteins. FIGS. 2A and B show exemplary results of a Car-FCS fractionation run and the subsequent SDS-PAGE and ELISA analysis of the fractions. The graph plots ELISA signals against HPLC-fraction numbers and overlays the HPLC-chromatogram. HPLC fractions were probed for carbamylated proteins using two negative control serum samples from healthy volunteers (Neg PMDx 1193 and PMDx1196) and four serum samples from RA patients, including two serum samples having anti-CarP antibodies and no anti-citrullinated protein antibodies (CarP$^+$/ACPA$^-$; BVx0038, BVx0077) and two serum samples having ACPA antibodies and no anti-CarP antibodies (CarP$^-$/ACPA$^+$; BVx0032, BVx0008).

In general, strong ELISA signals were observed with sera containing anti-CarP antibodies (BVx0038, BVx0077), but not with ACPA$^+$ sera lacking anti-CarP antibodies. Sera lacking anti-CarP antibodies showed ELISA signals close to background across all HPLC fractions. These results demonstrate the selectivity of ACPAs for citrullinated proteins versus carbamylated proteins. Conversely, these results demonstrate the specific interaction of certain carbamylated FCS proteins with a subset of autoantibodies from human RA patients that recognize carbamylated proteins and not citrullinated proteins.

SDS-PAGE analysis of fractionated Car-FCS revealed two relatively weak protein bands in fractions 1G4 and 1G6 (band 3 and 4) and stronger protein bands in the subsequent fractions. However, ELISA signals were found to be much stronger in HPLC fractions no. 1G4 and 1G6 than in subsequent fractions, especially with the BVx0038 (CarP+/ACPA−) serum. The protein bands were subjected to chymotryptic digestion and mass spectrometry (MS). See, FIGS. 3A-C. MS analysis identified bands 3 as bovine α(1)-antitrypsin (A1AT). See, FIGS. 3B and 3C.

In summary, this example shows that carbamylated bovine A1AT is a major carbamylated protein in carbamylated FCS recognized by anti-CarP antibodies from human RA patients.

Example II

The Reactivity of Anti-CarP Antibodies Against Human Car-A1AT Correlates with their Reactivity Against Car-FCS This example demonstrates that the reactivity of anti-CarP antibodies from human RA patients against in vitro carbamylated human A1AT (Car-hA1AT) correlates with the antibodies' reactivity against Car-FCS. These results suggest that Car-hA1AT can be used instead of Car-FCS in the development of assays for the detection of anti-CarP antibodies in the serum of human RA patients and for the diagnostic and prognostic assessment of a RA patient's disease and disease progression.

In vitro carbamylated human A1AT (Car-hA1AT) was produced by reacting purified hA1AT (Lee Biosolutions, St. Louis, Mo.; cat. no. 106-11) with potassium cyanate. In brief, A 2M solution of potassium cyanate (KOCN, Sigma-Aldrich, St. Louis, Mo.; cat no. 215074-500G) was prepared in PBS. The purified hA1AT was diluted to 2 mg/ml in PBS. The 2M KOCN solution was then mixed with the hA1AT in a 1:1 volume-by-volume proportion resulting in a solution with 1M of KOCN and 1 mg/ml of hA1AT. An unmodified hA1AT aliquot was retained as a reference protein. The mixed hA1AT-KOCN solution was incubated overnight at 37° C. to produce Car-hA1AT. Following the incubation period, the Car-hA1AT solution was dialyzed against PBS (2 L) for 48 hrs, during which the PBS was refreshed 5 times.

Figure 4:
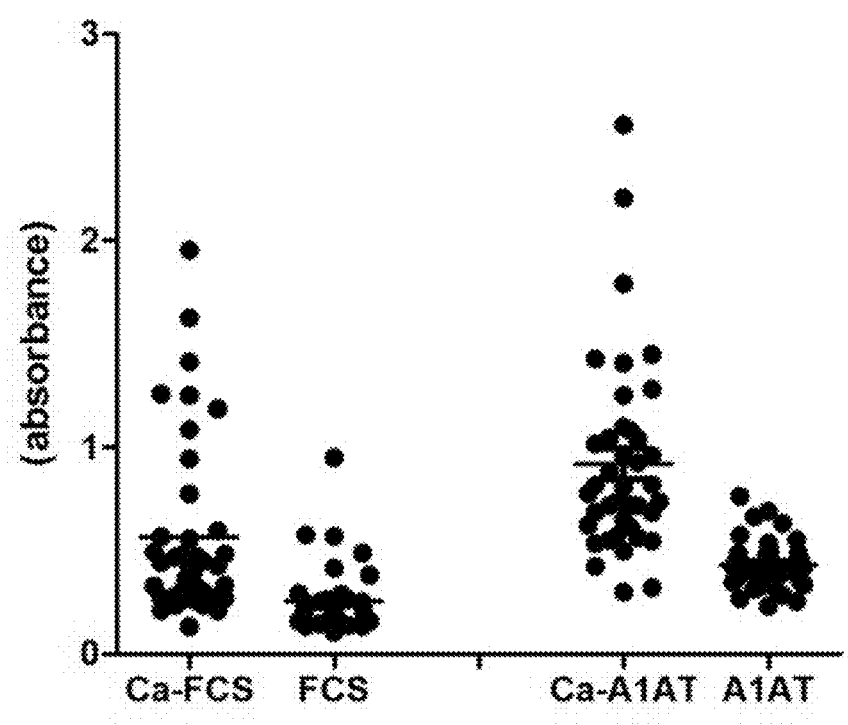
FIG. 4 illustrates the detection of anti-CarP antibodies in serum samples from human RA patients using in vitro carbamylated or uncarbamylated fetal calf serum (Ca-FCS) and in vitro carbamylated or uncarbamylated human A1AT (Ca-A1AT). Relative absorbance signals of colorimetric ELISAs are plotted for each patient sample and each carbamylated or uncarbamylated antigen.
Figure 5:
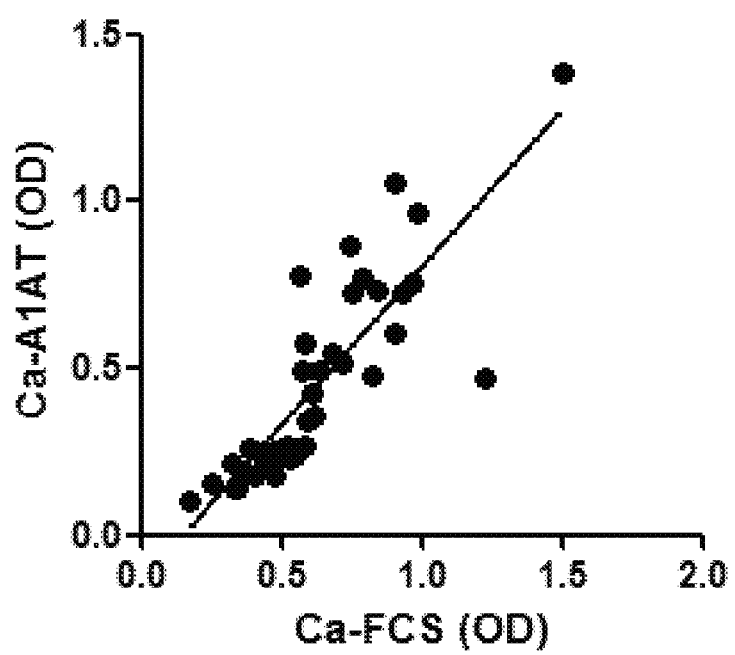
FIG. 5 illustrates the detection of anti-CarP antibodies in serum samples from human RA patients using in vitro carbamylated fetal calf serum (Ca-FCS) or in vitro carbamylated human A1AT (Ca-A1AT). Results of exemplary Ca-FCS ELISA assays were plotted against the results of corresponding exemplary A1AT assays.

An ELISA-based analysis was performed, essentially as described in Example 1, to compare the reactivity of human anti-CarP antibodies against Car-FCS and Car-hA1AT. Serum samples from about 30 RA patients were tested that contained a range of anti-CarP antibody amounts. The results of this comparative ELISA analysis are illustrated in FIGS. 4 and 5. FIG. 4 demonstrates that anti-CarP antibodies from RA patients form complexes with Car-A1AT in a carbamylation-dependent manner (third and fourth column). FIG. 4 further shows that anti-CarP antibody recognition of Car-A1AT is of the same or greater specificity (relative to A1AT, see third and fourth column) as anti-CarP antibody recognition of Car-FCS (relative to FCS, see first and second column). FIG. 5 shows that the reactivity of anti-CarP antibodies against human Car-A1AT was found to correlate with their reactivity against Car-FCS.

Figure 6A:
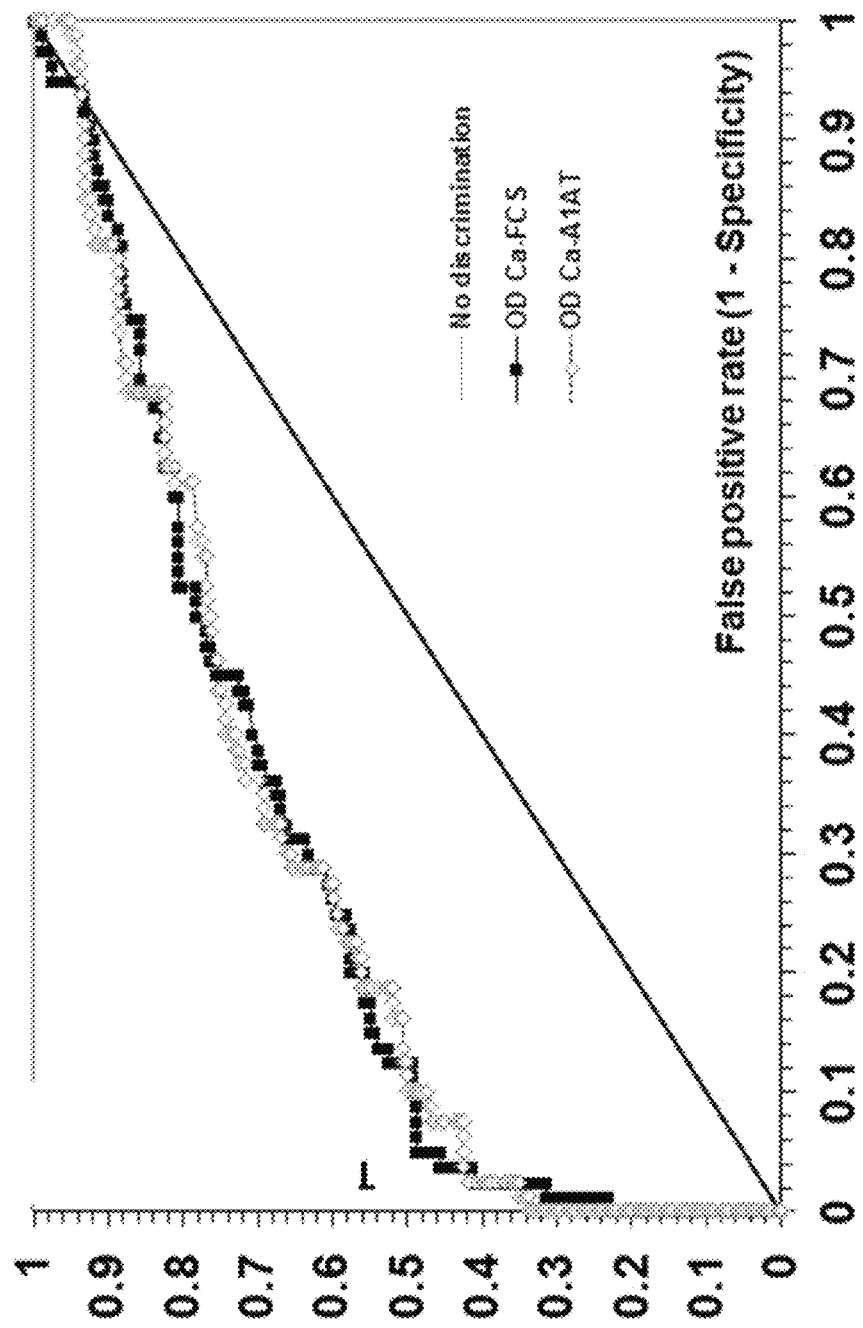
FIGS. 6A-C illustrate an exemplary comparison of in vitro carbamylated fetal calf serum (Ca-FCS) and in vitro carbamylated human A1AT (Ca-A1AT) in the discrimination of RA patients and healthy controls.
Figure 6B:
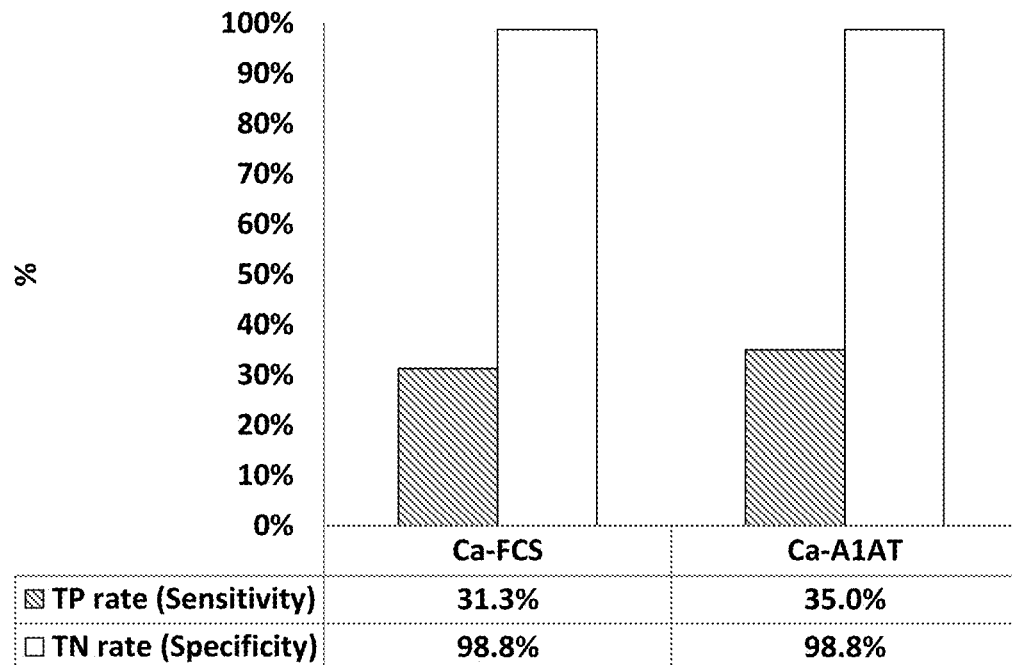
Figure 6C:
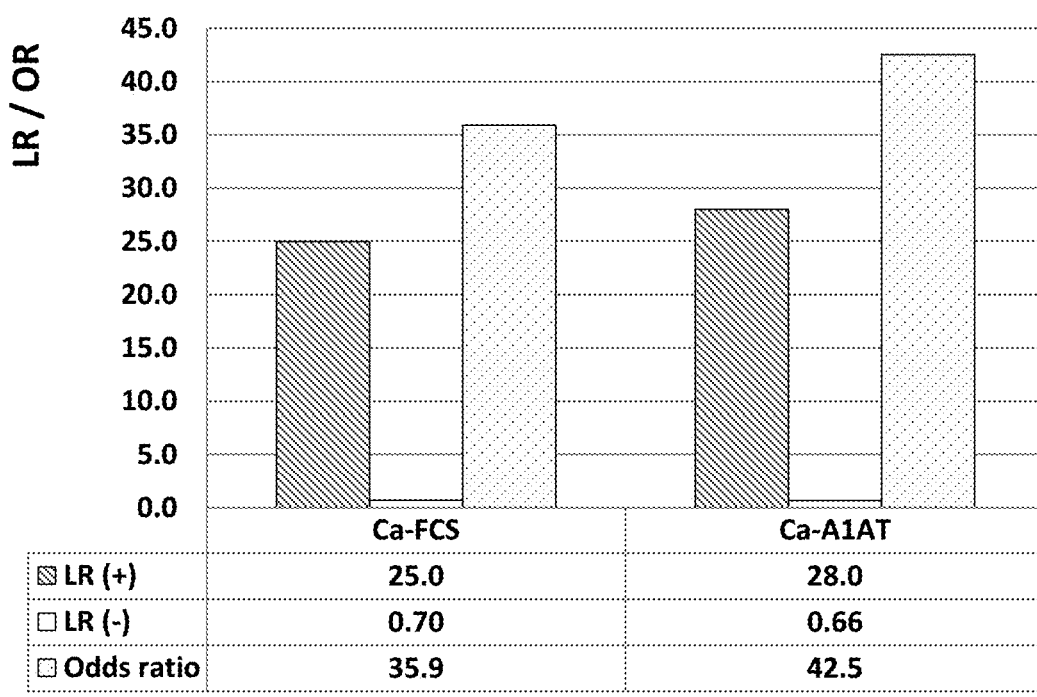

A receiver operating characteristic (ROC) analysis was conducted to compare the performance of an ELISA assay based on in vitro carbamylated fetal calf serum (Ca-FCS) and an ELISA assay based on in vitro carbamylated human A1AT (Ca-A1AT) with respect to the discrimination of RA patients and healthy controls. See FIGS. 6A-C. The obtained ROC curves and area under the curves (AUC) were found to be similar for the Ca-FCS and Ca-A1AT based assays. However, in the clinically relevant high-specificity area, the ROC curve of the Ca-A1AT based assay was found to be superior to the curve of the Ca-FCS based assay. See FIG. 6A. At a fixed specificity of 98.8%, the sensitivity of the Ca-A1AT based assay was found to be higher than the sensitivity of the Ca-FCS based assay area. See FIG. 6B. Likelihood and odds ratios were found to be higher for the Ca-A1AT based assay than for the Ca-FCS based assay. See FIG. 6C.

In summary, these results indicate that A1AT is a dominant carbamylated protein antigen present in FCS. Moreover, in vitro carbamylated hA1AT (Car-hA1AT) was shown to act as an effective purified protein antigen for the development of assays for the detection of anti-CarP antibodies and the diagnostic and prognostic assessment of RA patients' disease.

Although the disclosure has been described with reference to the disclosed embodiments, those skilled in the art will readily appreciate that the specific examples and studies detailed above are only illustrative of the disclosure. It should be understood that various modifications can be made without departing from the spirit of the disclosure. Accordingly, the disclosure is limited only by the following claims.

What is claimed:

1. A purified polypeptide comprising an in vitro carbamylated human alpha 1 antitrypsin (hA1AT), or an in vitro carbamylated fragment thereof, wherein the purified polypeptide is immobilized on a solid support.

2. The purified polypeptide of claim 1, wherein the purified polypeptide is a purified recombinant polypeptide encoded by cDNA, or the purified polypeptide is hA1AT, or an in vitro carbamylated fragment thereof, purified from blood, serum, plasma, urine, or synovial fluid, or wherein the hA1AT, or the in vitro carbamylated fragment thereof, comprises the amino acid sequence of SEQ ID NO:1, or wherein the hA1AT, or the in vitro carbamylated fragment thereof, has greater than 70%, greater than 75%, greater than 80%, greater than 85%, greater than 90%, greater than 95%, greater than 96%, greater than 97%, greater than 98%, or greater than 99% sequence identity to SEQ ID NO:1, or wherein the hA1AT, or the in vitro carbamylated fragment thereof, comprises a fragment of 8 or more contiguous amino acids of SEQ ID NO:1, or wherein the hA1AT, or the in vitro carbamylated fragment thereof, comprises a fragment of 8 or more contiguous amino acids with greater than 80%, greater than 85%, greater than 90%, greater than 95%, greater than 96%, greater than 97%, greater than 98%, or greater than 99% sequence identity to SEQ ID NO:1, or wherein the hA1AT, or the in vitro carbamylated fragment thereof, comprises the amino acid sequence of any one of SEQ ID NOS:3-32, or wherein the in vitro carbamylated hA1AT, or the in vitro carbamylated fragment thereof, comprises the amino acid sequence of any one of SEQ ID NOS:33-203.

3. A complex comprising a purified polypeptide, wherein the purified polypeptide comprises an in vitro carbamylated human alpha 1 antitrypsin (hA1AT) or an in vitro carbamylated fragment thereof, and one or more anti-carbamylated protein (anti-CarP) antibodies.

4. A method for detecting an anti-CarP antibody in a subject comprising:
a) contacting a sample from the subject with a purified polypeptide comprising an in vitro carbamylated hA1AT, or an in vitro carbamylated fragment thereof, to form a complex between an anti-CarP antibody of the sample and the purified polypeptide, wherein the purified polypeptide is immobilized on a solid support; and
b) detecting the presence or absence of the anti-CarP antibody-purified polypeptide complex.

5. The method of claim 4, wherein the presence or absence of the anti-CarP antibody-purified polypeptide complex is detected by an assay selected from the group consisting of an enzyme-linked immunosorbent assay (ELISA), a fluorescent immunosorbent assay (FIA), a chemiluminescence immuno assay (CIA), a radioimmunoassay (RIA), an enzyme multiplied immunoassay, a solid phase radioimmunoassay (SPROA), a fluorescence polarization (FP) assay, a fluorescence resonance energy transfer (FRET) assay, a time-resolved fluorescence resonance energy transfer (TR-FRET) assay, a surface plasmon resonance (SPR) assay, and a Dot-Blot assay.

6. The method of claim 4, wherein the subject is suspected of having rheumatoid arthritis (RA), or wherein the subject is negative for anti-citrullinated protein antibodies (ACPA⁻).

7. The method of claim 4, wherein detecting the presence or absence of the anti-CarP antibody-polypeptide complex comprises comparing the level of the anti-CarP antibody in the sample from the subject to a control level of anti-CarP antibody in a sample from a healthy control individual, wherein an increase in anti-CarP-antibody level in the sample compared to the control level indicates that the subject has RA.

8. A kit for detecting an anti-CarP antibody in a subject, comprising a purified polypeptide comprising an in vitro carbamylated hA1AT, or an in vitro carbamylated fragment thereof, an ancillary reagent and a solid support, wherein the purified polypeptide is immobilized on the surface of the solid support.

9. The kit of claim 8, wherein the ancillary reagent is selected from the group consisting of a secondary antibody, a detection reagent, an immobilization buffer, a blocking buffer, a washing buffer, and a detection buffer.

10. The kit of claim 9, wherein the secondary antibody is selected from an anti-human IgA antibody, anti-human IgD antibody, anti-human IgE antibody, anti-human IgG antibody, and anti-human IgM antibody.

11. The kit of claim 9, wherein the detection reagent comprises a fluorescent detection reagent or a luminescent detection reagent.

12. The kit of claim 9, wherein the luminescent detection reagent comprises luminol or luciferin.

13. The kit of claim 8, wherein the kit includes a packaging having a label indicating the kit is used for diagnosis, prognosis or monitoring of RA or a RA subtype in the subject, or for detecting anti-CarP antibodies in the sample from the subject.

14. The kit of claim 13, wherein the label is approved by the United States Food and Drug Administration (FDA), the European Medicines Agency (EMA), the China Food and Drug Administration (CFDA) or the Japanese Ministery of Health Labor and Welfare (MHLW), or wherein the kit is labeled for use as an In Vitro Diagnostic (IVD) companion diagnostic device.

15. The kit of claim 8, wherein the solid support comprises a microtiter well plate, a slide, a chip, a microfluidic cartridge, a cuvette, a bead, a resin, or a flow cell.

16. The kit of claim 15, wherein the microtiter plate is a 96-well plate, a 384-well plate, or a 1536-well plate, or wherein the purified polypeptide is immobilized in one or more wells of the microtiter plate.

17. The kit of claim 8, wherein the in vitro carbamylated hA1AT, or the in vitro carbamylated fragment thereof, comprises a purified recombinant polypeptide encoded by cDNA or a synthetic peptide with an amino acid sequence of any one of SEQ ID NOS:33-203.

18. A purified polypeptide consisting of an in vitro carbamylated hA1AT fragment.

19. A kit for detecting an anti-CarP antibody in a subject, comprising a purified polypeptide comprising an in vitro carbamylated hA1AT, or an in vitro carbamylated fragment thereof, and an ancillary reagent.

* * * * *